US011155073B2

(12) United States Patent
O'Neill et al.

(10) Patent No.: US 11,155,073 B2
(45) Date of Patent: *Oct. 26, 2021

(54) LASER-PRODUCED POROUS SURFACE

(71) Applicant: Howmedica Osteonics Corp., Mahwah, NJ (US)

(72) Inventors: William O'Neill, Cambridge (GB); Christopher J. Sutcliffe, Liverpool (GB); Eric Jones, Limerick (IE); Robin Stamp, Montclair, NJ (US)

(73) Assignees: Howmedica Osteonics Corp., Mahwah, NJ (US); The University Of Liverpool

( * ) Notice: Subject to any disclaimer, the term of this patent is extended or adjusted under 35 U.S.C. 154(b) by 0 days.

This patent is subject to a terminal disclaimer.

(21) Appl. No.: 16/690,307

(22) Filed: Nov. 21, 2019

(65) Prior Publication Data

US 2020/0086625 A1    Mar. 19, 2020

Related U.S. Application Data

(63) Continuation of application No. 14/671,545, filed on Mar. 27, 2015, now Pat. No. 10,525,688, which is a
(Continued)

(51) Int. Cl.
*B33Y 10/00* (2015.01)
*B33Y 80/00* (2015.01)
(Continued)

(52) U.S. Cl.
CPC .......... *B33Y 10/00* (2014.12); *A61F 2/30771* (2013.01); *A61F 2/30907* (2013.01);
(Continued)

(58) Field of Classification Search
CPC ......... B33Y 10/00; B33Y 70/00; B33Y 80/00; B22F 10/20; B22F 7/004; B22F 2999/00;
(Continued)

(56) References Cited

U.S. PATENT DOCUMENTS

| 14,403 A | 3/1856 | Brown et al. |
| 222,687 A | 12/1879 | Fresco |
| (Continued) | | |

FOREIGN PATENT DOCUMENTS

| CA | 2295896 A1 | 7/2000 |
| CA | 2448592 A1 | 5/2004 |
| (Continued) | | |

OTHER PUBLICATIONS

Chua, C.K., et al., "Development of a Tissue Engineering Scaffold Structure Library for Rapid Prototyping Part 1: Investigation and Classification", 2003, Int J Adv Manuf Technology, Springer-Verlag. (Year: 2003).*

(Continued)

*Primary Examiner* — Cedric Johnson
(74) *Attorney, Agent, or Firm* — Lerner, David, Littenberg, Krumholz & Mentlik, LLP

(57) ABSTRACT

The present invention disclosed a method of producing a three-dimensional porous tissue in-growth structure. The method includes the steps of depositing a first layer of metal powder and scanning the first layer of metal powder with a laser beam to form a portion of a plurality of predetermined unit cells. Depositing at least one additional layer of metal powder onto a previous layer and repeating the step of scanning a laser beam for at least one of the additional layers in order to continuing forming the predetermined unit cells. The method further includes continuing the depositing and scanning steps to form a medical implant.

16 Claims, 60 Drawing Sheets

Related U.S. Application Data continuation of application No. 13/605,354, filed on Sep. 6, 2012, now Pat. No. 8,992,703, which is a continuation of application No. 12/846,327, filed on Jul. 29, 2010, now Pat. No. 9,456,901, which is a continuation of application No. 11/027,421, filed on Dec. 30, 2004, now abandoned, said application No. 13/605,354 is a continuation-in-part of application No. 12/843,376, filed on Jul. 26, 2010, now Pat. No. 8,268,100, which is a continuation of application No. 12/386,679, filed on Apr. 22, 2009, now Pat. No. 8,268,099, which is a continuation of application No. 10/704,270, filed on Nov. 7, 2003, now Pat. No. 7,537,664.

(60) Provisional application No. 60/425,657, filed on Nov. 12, 2002, provisional application No. 60/424,923, filed on Nov. 8, 2002.

(51) Int. Cl.

| | | |
|---|---|---|
| *B33Y 70/00* | (2020.01) | |
| *A61F 2/30* | (2006.01) | |
| *B22F 7/00* | (2006.01) | |
| *C23C 4/02* | (2006.01) | |
| *C23C 4/12* | (2016.01) | |
| *C23C 4/18* | (2006.01) | |
| *C23C 24/04* | (2006.01) | |
| *C23C 24/10* | (2006.01) | |
| *B23K 26/382* | (2014.01) | |
| *B23K 26/40* | (2014.01) | |
| *B29C 64/153* | (2017.01) | |
| *B22F 10/20* | (2021.01) | |
| *B22F 10/38* | (2021.01) | |
| *B22F 10/28* | (2021.01) | |
| *B22F 10/366* | (2021.01) | |
| *B22F 3/11* | (2006.01) | |
| *C23C 26/02* | (2006.01) | |
| *B23K 103/14* | (2006.01) | |
| *A61F 2/34* | (2006.01) | |
| *A61F 2/36* | (2006.01) | |
| *A61F 2/38* | (2006.01) | |
| *B23K 103/00* | (2006.01) | |
| *B23K 103/04* | (2006.01) | |
| *B23K 101/34* | (2006.01) | |
| *B23K 103/08* | (2006.01) | |
| *B23K 103/18* | (2006.01) | |

(52) U.S. Cl.
CPC ........ *A61F 2/30965* (2013.01); *B22F 3/1103* (2013.01); *B22F 3/1115* (2013.01); *B22F 7/004* (2013.01); *B22F 10/20* (2021.01); *B22F 10/28* (2021.01); *B22F 10/366* (2021.01); *B22F 10/38* (2021.01); *B23K 26/382* (2015.10); *B23K 26/40* (2013.01); *B29C 64/153* (2017.08); *B33Y 70/00* (2014.12); *B33Y 80/00* (2014.12); *C23C 4/02* (2013.01); *C23C 4/12* (2013.01); *C23C 4/18* (2013.01); *C23C 24/04* (2013.01); *C23C 24/10* (2013.01); *C23C 26/02* (2013.01); *A61F 2/3094* (2013.01); *A61F 2/30767* (2013.01); *A61F 2/34* (2013.01); *A61F 2/3662* (2013.01); *A61F 2/389* (2013.01); *A61F 2/3859* (2013.01); *A61F 2002/30006* (2013.01); *A61F 2002/30011* (2013.01); *A61F 2002/3092* (2013.01); *A61F 2002/3097* (2013.01); *A61F 2002/30153* (2013.01); *A61F 2002/30199* (2013.01); *A61F 2002/30261* (2013.01); *A61F 2002/30915* (2013.01); *A61F 2002/30929* (2013.01); *A61F 2002/30968* (2013.01); *A61F 2002/30971* (2013.01); *A61F 2230/0019* (2013.01); *A61F 2230/0063* (2013.01); *A61F 2230/0082* (2013.01); *A61F 2250/0015* (2013.01); *A61F 2250/0023* (2013.01); *A61F 2310/00017* (2013.01); *A61F 2310/00023* (2013.01); *A61F 2310/00029* (2013.01); *A61F 2310/00095* (2013.01); *A61F 2310/00131* (2013.01); *A61F 2310/00401* (2013.01); *A61F 2310/00407* (2013.01); *A61F 2310/00413* (2013.01); *A61F 2310/00491* (2013.01); *A61F 2310/00544* (2013.01); *B22F 2301/15* (2013.01); *B22F 2301/20* (2013.01); *B22F 2301/205* (2013.01); *B22F 2301/35* (2013.01); *B22F 2999/00* (2013.01); *B23K 2101/35* (2018.08); *B23K 2103/05* (2018.08); *B23K 2103/08* (2018.08); *B23K 2103/14* (2018.08); *B23K 2103/26* (2018.08); *B23K 2103/50* (2018.08); *Y02P 10/25* (2015.11)

(58) Field of Classification Search
CPC .. B23K 26/382; B23K 26/40; B23K 2103/50; B23K 2101/35; B23K 2103/08; B23K 2103/26; B23K 2103/14; B29C 64/153; A61F 2/30771; A61F 2/30907; A61F 2/30965; A61F 2/30767; A61F 2/3094; A61F 2/34; A61F 2/3662; A61F 2/3859; A61F 2/389; A61F 2002/30006; A61F 2002/30011; A61F 2002/30153; A61F 2002/30199; A61F 2002/30261; A61F 2002/30915; A61F 2002/3092; A61F 2002/30929; A61F 2002/30968; A61F 2002/3097; A61F 2002/30971; A61F 2230/0019; A61F 2230/0063; A61F 2230/0082; A61F 2250/0015; A61F 2250/0023; A61F 2310/00017; A61F 2310/00023; A61F 2310/00029; A61F 2310/00131; A61F 2310/00401; A61F 2310/00407; A61F 2310/00413; A61F 2310/00491; A61F 2310/00544; C23C 4/02; C23C 4/12; C23C 4/18; C23C 24/04; C23C 24/10; C23C 26/02; Y02P 10/25
USPC .......................................................... 703/1
See application file for complete search history.

(56) References Cited

U.S. PATENT DOCUMENTS

| | | |
|---|---|---|
| 2,373,769 A | 4/1945 | Macy |
| 3,520,099 A | 7/1970 | Mattes |
| 3,556,918 A | 1/1971 | Lemelson |
| 3,605,123 A | 9/1971 | Pratt et al. |
| 3,806,961 A | 4/1974 | Muller |
| 3,816,855 A | 6/1974 | Saleh |
| 3,826,054 A | 7/1974 | Culpepper, Jr. |
| 3,906,550 A | 9/1975 | Rostoker et al. |
| 4,047,349 A | 9/1977 | Aguilar, Jr. |
| 4,073,999 A | 2/1978 | Bryan et al. |
| 4,085,466 A | 4/1978 | Goodfellow et al. |
| 4,117,302 A | 9/1978 | Earle et al. |
| 4,154,040 A | 5/1979 | Pace |
| 4,164,794 A | 8/1979 | Spector et al. |
| 4,179,485 A | 12/1979 | Tritten |
| 4,202,055 A | 5/1980 | Reiner et al. |
| 4,218,494 A | 8/1980 | Belmondo et al. |
| 4,247,508 A | 1/1981 | Housholder |

(56) References Cited

U.S. PATENT DOCUMENTS

| | | |
|---|---|---|
| 4,259,072 A | 3/1981 | Hirabayashi et al. |
| 4,305,340 A | 12/1981 | Iwaki et al. |
| 4,344,193 A | 8/1982 | Kenny |
| 4,385,404 A | 5/1983 | Sully et al. |
| 4,444,818 A | 4/1984 | Tominaga et al. |
| 4,474,861 A | 10/1984 | Ecer |
| 4,479,271 A | 10/1984 | Bolesky et al. |
| 4,502,161 A | 3/1985 | Wall |
| 4,513,045 A | 4/1985 | Bondoc et al. |
| 4,542,539 A | 9/1985 | Rowe, Jr. et al. |
| 4,543,158 A | 9/1985 | Bondoc et al. |
| 4,550,448 A | 11/1985 | Kenna |
| 4,636,219 A | 1/1987 | Pratt et al. |
| 4,644,942 A | 2/1987 | Sump |
| 4,659,331 A | 4/1987 | Matthews et al. |
| 4,673,408 A | 6/1987 | Grobbelaar |
| 4,673,409 A | 6/1987 | Van Kampen |
| 4,714,473 A | 12/1987 | Bloebaum |
| 4,714,474 A | 12/1987 | Brooks, Jr. et al. |
| 4,719,908 A | 1/1988 | Averill et al. |
| 4,766,029 A | 8/1988 | Brock et al. |
| 4,863,538 A | 9/1989 | Deckard |
| 4,944,756 A | 7/1990 | Kenna |
| 4,944,817 A | 7/1990 | Bourell et al. |
| 4,957,819 A | 9/1990 | Kawahara et al. |
| 4,961,154 A | 10/1990 | Pomerantz et al. |
| 4,969,302 A | 11/1990 | Coggan et al. |
| 4,969,907 A | 11/1990 | Koch |
| 4,969,910 A | 11/1990 | Frey et al. |
| 4,976,738 A | 12/1990 | Frey et al. |
| 4,978,355 A | 12/1990 | Frey et al. |
| 4,990,163 A | 2/1991 | Ducheyne et al. |
| 4,997,445 A | 3/1991 | Hodorek |
| 5,002,572 A | 3/1991 | Picha |
| 5,004,476 A | 4/1991 | Cook |
| 5,017,753 A | 5/1991 | Deckard |
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,090,174 A | 2/1992 | Fragale |
| 5,108,432 A | 4/1992 | Gustayson |
| 5,108,441 A | 4/1992 | McDowell |
| 5,147,402 A | 9/1992 | Bohler et al. |
| 5,150,304 A | 9/1992 | Berchem et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,192,328 A | 3/1993 | Winters |
| 5,219,362 A | 6/1993 | Tuke et al. |
| 5,274,565 A | 12/1993 | Reuben |
| 5,282,861 A | 2/1994 | Kaplan |
| 5,282,870 A | 2/1994 | Moser et al. |
| 5,287,435 A | 2/1994 | Cohen et al. |
| 5,298,115 A | 3/1994 | Leonard |
| 5,314,478 A | 5/1994 | Oka et al. |
| 5,323,954 A | 6/1994 | Shetty et al. |
| 5,336,518 A | 8/1994 | Narayanan et al. |
| 5,352,405 A | 10/1994 | Beaman et al. |
| 5,356,433 A | 10/1994 | Rowland et al. |
| 5,358,529 A | 10/1994 | Davidson |
| 5,368,602 A | 11/1994 | de la Torre |
| 5,370,692 A | 12/1994 | Fink et al. |
| 5,386,500 A | 1/1995 | Pomerantz et al. |
| 5,398,193 A | 3/1995 | deAngelis |
| 5,425,210 A | 6/1995 | Zafir |
| 5,443,510 A | 8/1995 | Shetty et al. |
| 5,443,518 A | 8/1995 | Insall |
| 5,461,839 A | 10/1995 | Beck |
| 5,486,599 A | 1/1996 | Saunders et al. |
| 5,489,306 A | 2/1996 | Gorski |
| 5,490,962 A | 2/1996 | Cima et al. |
| 5,496,372 A | 3/1996 | Hamamoto et al. |
| 5,504,300 A | 4/1996 | Devanathan et al. |
| 5,507,815 A | 4/1996 | Wagner et al. |
| 5,510,066 A | 4/1996 | Fink et al. |
| 5,514,183 A | 5/1996 | Epstein et al. |
| 5,518,680 A | 5/1996 | Cima et al. |
| 5,526,627 A | 6/1996 | Beck |
| 5,549,700 A | 8/1996 | Graham et al. |
| 5,571,185 A | 11/1996 | Schug |
| 5,571,196 A | 11/1996 | Stein |
| 5,580,353 A | 12/1996 | Mendes et al. |
| 5,609,646 A | 3/1997 | Field et al. |
| 5,616,294 A | 4/1997 | Deckard |
| 5,624,463 A | 4/1997 | Stone et al. |
| 5,632,745 A | 5/1997 | Schwartz |
| 5,640,667 A | 6/1997 | Freitag et al. |
| 5,648,450 A | 7/1997 | Dickens, Jr. et al. |
| 5,665,118 A | 9/1997 | LaSalle et al. |
| 5,681,354 A | 10/1997 | Eckhoff |
| 5,702,448 A | 12/1997 | Buechel et al. |
| 5,714,103 A | 2/1998 | Bauer et al. |
| 5,716,358 A | 2/1998 | Ochoa et al. |
| 5,728,162 A | 3/1998 | Eckhoff |
| 5,729,946 A | 3/1998 | Beck |
| 5,735,903 A | 4/1998 | Li et al. |
| 5,749,874 A | 5/1998 | Schwartz |
| 5,768,134 A | 6/1998 | Swaelens et al. |
| 5,769,092 A | 6/1998 | Williamson, Jr. |
| 5,769,899 A | 6/1998 | Schwartz et al. |
| 5,773,789 A | 6/1998 | Devanathan et al. |
| 5,776,201 A | 7/1998 | Colleran et al. |
| 5,782,908 A | 7/1998 | Cahalan et al. |
| 5,795,353 A | 8/1998 | Felt |
| 5,798,924 A | 8/1998 | Eufinger et al. |
| 5,824,098 A | 10/1998 | Stein |
| 5,824,102 A | 10/1998 | Buscayret |
| 5,839,247 A | 11/1998 | Beck |
| 5,857,303 A | 1/1999 | Beck et al. |
| 5,866,113 A | 2/1999 | Hendriks et al. |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,987,838 A | 11/1999 | Beck |
| 5,989,472 A | 11/1999 | Ashby et al. |
| 6,013,855 A | 1/2000 | McPherson et al. |
| 6,042,774 A | 3/2000 | Wilkening et al. |
| 6,045,581 A | 4/2000 | Burkinshaw |
| 6,046,426 A | 4/2000 | Jeantette et al. |
| 6,049,054 A | 4/2000 | Panchison et al. |
| 6,077,989 A | 6/2000 | Kandel et al. |
| 6,087,553 A | 7/2000 | Cohen et al. |
| 6,096,043 A | 8/2000 | Techiera et al. |
| 6,112,109 A | 8/2000 | D'Urso |
| 6,128,866 A | 10/2000 | Wearne |
| 6,132,468 A | 10/2000 | Mansmann |
| 6,139,585 A | 10/2000 | Li |
| 6,149,688 A | 11/2000 | Brosnahan et al. |
| 6,149,689 A | 11/2000 | Grundei |
| 6,164,032 A | 12/2000 | Beck |
| 6,171,340 B1 | 1/2001 | McDowell |
| 6,190,407 B1 | 2/2001 | Ogle et al. |
| 6,206,924 B1 | 3/2001 | Timm |
| 6,206,927 B1 | 3/2001 | Fell et al. |
| 6,209,621 B1 | 4/2001 | Treacy |
| 6,215,093 B1 | 4/2001 | Meiners et al. |
| 6,217,615 B1 | 4/2001 | Sioshansi et al. |
| 6,248,131 B1 | 6/2001 | Felt et al. |
| 6,251,143 B1 | 6/2001 | Schwartz et al. |
| 6,254,639 B1 | 7/2001 | Peckitt |
| 6,261,322 B1 | 7/2001 | Despres, III et al. |
| 6,261,493 B1 | 7/2001 | Gaylo et al. |
| 6,280,478 B1 | 8/2001 | Richter et al. |
| 6,283,997 B1 | 9/2001 | Garg et al. |
| 6,290,726 B1 | 9/2001 | Pope et al. |
| 6,299,645 B1 | 10/2001 | Ogden |
| 6,344,061 B1 | 2/2002 | Leitao et al. |
| 6,350,284 B1 | 2/2002 | Tormala et al. |

(56) References Cited

U.S. PATENT DOCUMENTS

| | | |
|---|---|---|
| 6,355,086 B2 | 3/2002 | Brown et al. |
| 6,368,354 B2 | 4/2002 | Burstein et al. |
| 6,370,382 B1 | 4/2002 | Kang et al. |
| 6,371,958 B1 | 4/2002 | Overaker |
| 6,379,816 B1 | 4/2002 | De Loose et al. |
| 6,385,585 B1 | 5/2002 | Jonsson et al. |
| 6,395,327 B1 | 5/2002 | Shetty |
| 6,406,497 B2 | 6/2002 | Takei |
| 6,415,574 B2 | 7/2002 | Beck |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,494,914 B2 | 12/2002 | Brown et al. |
| 6,497,728 B2 | 12/2002 | Yong |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,582,715 B1 | 6/2003 | Barry et al. |
| 6,589,283 B1 | 7/2003 | Metzger et al. |
| 6,592,598 B2 | 7/2003 | Vibe-Hansen et al. |
| 6,599,301 B2 | 7/2003 | Vibe-Hansen et al. |
| 6,599,322 B1 | 7/2003 | Amrich et al. |
| 6,599,323 B2 | 7/2003 | Melican et al. |
| 6,610,067 B2 | 8/2003 | Tallarida et al. |
| 6,626,945 B2 | 9/2003 | Simon et al. |
| 6,632,246 B1 | 10/2003 | Simon et al. |
| 6,652,246 B1 | 11/2003 | Lin et al. |
| 6,652,587 B2 | 11/2003 | Felt et al. |
| 6,676,892 B2 | 1/2004 | Das et al. |
| 6,679,917 B2 | 1/2004 | Ek |
| 6,682,567 B1 | 1/2004 | Schroeder |
| 6,686,437 B2 | 2/2004 | Buchman et al. |
| 6,699,252 B2 | 3/2004 | Farr, II et al. |
| 6,702,848 B1 | 3/2004 | Zilla et al. |
| 6,709,462 B2 | 3/2004 | Hanssen |
| 6,712,822 B2 | 3/2004 | Re et al. |
| 6,712,856 B1 | 3/2004 | Carignan et al. |
| 6,716,957 B2 | 4/2004 | Tunc |
| 6,743,232 B2 | 6/2004 | Overaker et al. |
| 6,770,099 B2 | 8/2004 | Andriacchi et al. |
| 6,772,026 B2 | 8/2004 | Bradbury et al. |
| 6,802,864 B2 | 10/2004 | Tornier |
| 6,811,569 B1 | 11/2004 | Afriat et al. |
| 6,846,329 B2 | 1/2005 | McMinn |
| 6,850,125 B2 | 2/2005 | Norman et al. |
| 6,852,125 B2 | 2/2005 | Simon et al. |
| 6,855,165 B2 | 2/2005 | Fell et al. |
| 6,863,689 B2 | 3/2005 | Ralph et al. |
| 6,866,684 B2 | 3/2005 | Fell et al. |
| 6,893,463 B2 | 5/2005 | Fell et al. |
| 6,911,044 B2 | 6/2005 | Fell et al. |
| 6,916,341 B2 | 7/2005 | Rolston |
| 6,921,264 B2 | 7/2005 | Mayer et al. |
| 6,923,831 B2 | 8/2005 | Fell et al. |
| 6,932,610 B2 | 8/2005 | Ono et al. |
| 6,966,932 B1 | 11/2005 | Schroeder |
| 6,993,406 B1 | 1/2006 | Cesarano, III et al. |
| 7,051,417 B2 | 5/2006 | Michelson |
| 7,168,283 B2 | 1/2007 | Van Note et al. |
| 7,294,149 B2 | 11/2007 | Hozack et al. |
| 7,332,537 B2 | 2/2008 | Bredt et al. |
| 7,388,972 B2 | 6/2008 | Kitson |
| 7,494,507 B2 | 2/2009 | Dixon et al. |
| 7,497,876 B2 | 3/2009 | Tuke et al. |
| 7,521,017 B2 | 4/2009 | Kunze et al. |
| 7,563,284 B2 | 7/2009 | Coppes et al. |
| 7,597,715 B2 | 10/2009 | Brown et al. |
| 7,632,575 B2 | 12/2009 | Justin et al. |
| 7,637,942 B2 | 12/2009 | Mangiardi et al. |
| 7,655,047 B2 | 2/2010 | Swords |
| 7,674,517 B2 | 3/2010 | Ramsey et al. |
| 7,718,109 B2 | 5/2010 | Robb et al. |
| 7,747,305 B2 | 6/2010 | Dean et al. |
| 7,779,890 B2 | 8/2010 | Frasier et al. |
| 7,875,083 B2 | 1/2011 | Sudmann |
| 7,879,275 B2 | 2/2011 | Smith et al. |
| 7,931,931 B2 | 4/2011 | Yon |
| 8,029,575 B2 | 10/2011 | Borden |
| 8,066,770 B2 | 11/2011 | Rivard et al. |
| 8,090,540 B2 | 1/2012 | Leo et al. |
| 8,247,333 B2 | 8/2012 | Sypeck et al. |
| 8,292,967 B2 | 10/2012 | Brown et al. |
| 8,308,807 B2 | 11/2012 | Seebeck et al. |
| 8,350,186 B2 | 1/2013 | Jones et al. |
| 8,430,930 B2 | 4/2013 | Hunt |
| 8,454,705 B2 | 6/2013 | Pressacco et al. |
| 8,551,173 B2 | 10/2013 | Lechmann et al. |
| 8,796,015 B2 | 8/2014 | Gingras |
| 8,843,229 B2 | 9/2014 | Vanasse et al. |
| 8,864,826 B2 | 10/2014 | Pressacco |
| 8,888,862 B2 | 11/2014 | McDonnell et al. |
| 8,979,938 B2 | 3/2015 | Linares |
| 8,983,646 B1 | 3/2015 | Hanna |
| 8,985,430 B2 | 3/2015 | Charlebois et al. |
| 9,370,426 B2 | 6/2016 | Gabbrielli et al. |
| 9,801,974 B2 | 10/2017 | Landon |
| 2001/0014403 A1 | 8/2001 | Brown et al. |
| 2002/0007294 A1* | 1/2002 | Bradbury ............ G06F 19/3418 705/2 |
| 2002/0010512 A1 | 1/2002 | Takei |
| 2002/0015654 A1 | 2/2002 | Das et al. |
| 2002/0016635 A1 | 2/2002 | Despres et al. |
| 2002/0062154 A1 | 5/2002 | Ayers |
| 2002/0102674 A1 | 8/2002 | Anderson |
| 2002/0127328 A1 | 9/2002 | Shetty |
| 2002/0130112 A1 | 9/2002 | Manasas et al. |
| 2002/0151983 A1 | 10/2002 | Shetty |
| 2002/0173855 A1 | 11/2002 | Mansmann |
| 2002/0187458 A1 | 12/2002 | Dolabdjian et al. |
| 2002/0198528 A1 | 12/2002 | Engh et al. |
| 2003/0012805 A1 | 1/2003 | Chen et al. |
| 2003/0032351 A1 | 2/2003 | Horner et al. |
| 2003/0033018 A1 | 2/2003 | Merchant |
| 2003/0045941 A1 | 3/2003 | Lewallen |
| 2003/0055500 A1 | 3/2003 | Fell et al. |
| 2003/0055501 A1 | 3/2003 | Fell et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0060888 A1 | 3/2003 | Fell et al. |
| 2003/0065400 A1 | 4/2003 | Beam et al. |
| 2003/0069638 A1 | 4/2003 | Barlow et al. |
| 2003/0069718 A1 | 4/2003 | Hollister et al. |
| 2003/0153977 A1 | 8/2003 | Suguro et al. |
| 2003/0153981 A1 | 8/2003 | Wang et al. |
| 2003/0155686 A1 | 8/2003 | Hawkins et al. |
| 2003/0158606 A1 | 8/2003 | Coon et al. |
| 2003/0206820 A1* | 11/2003 | Keicher ................. B33Y 10/00 419/9 |
| 2003/0209305 A1 | 11/2003 | Smith et al. |
| 2003/0220696 A1 | 11/2003 | Levine et al. |
| 2004/0006393 A1 | 1/2004 | Burkinshaw |
| 2004/0009228 A1 | 1/2004 | Tormala et al. |
| 2004/0015170 A1 | 1/2004 | Tallarida et al. |
| 2004/0023586 A1 | 2/2004 | Tilton |
| 2004/0044414 A1 | 3/2004 | Nowakowski |
| 2004/0054416 A1 | 3/2004 | Wyss et al. |
| 2004/0059356 A1 | 3/2004 | Gingras |
| 2004/0098132 A1 | 5/2004 | Andriacchi et al. |
| 2004/0121110 A1 | 6/2004 | Schmidt et al. |
| 2004/0143339 A1 | 7/2004 | Axelson et al. |
| 2004/0143341 A1 | 7/2004 | McLean |
| 2004/0148030 A1 | 7/2004 | Ek |
| 2004/0153163 A1 | 8/2004 | Posner |
| 2004/0162622 A1 | 8/2004 | Simon et al. |
| 2004/0167633 A1 | 8/2004 | Wen et al. |
| 2004/0191106 A1 | 9/2004 | O'Neill et al. |
| 2004/0199249 A1 | 10/2004 | Fell |
| 2004/0199250 A1 | 10/2004 | Fell |
| 2004/0204766 A1 | 10/2004 | Siebel |
| 2004/0230315 A1 | 11/2004 | Ek |
| 2004/0243237 A1 | 12/2004 | Unwin et al. |

(56) References Cited

U.S. PATENT DOCUMENTS

| | | |
|---|---|---|
| 2004/0267363 A1 | 12/2004 | Fell et al. |
| 2005/0033424 A1 | 2/2005 | Fell |
| 2005/0043816 A1 | 2/2005 | Datta et al. |
| 2005/0048193 A1 | 3/2005 | Li et al. |
| 2005/0070989 A1 | 3/2005 | Lye et al. |
| 2005/0079200 A1 | 4/2005 | Rathenow et al. |
| 2005/0085918 A1 | 4/2005 | Soffiati et al. |
| 2005/0085922 A1 | 4/2005 | Shappley et al. |
| 2005/0100578 A1 | 5/2005 | Schmid et al. |
| 2005/0103765 A1* | 5/2005 | Kawasaki ............ B29C 64/153 219/121.85 |
| 2005/0112397 A1 | 5/2005 | Rolfe et al. |
| 2005/0123672 A1 | 6/2005 | Justin et al. |
| 2005/0154471 A1 | 7/2005 | Aram et al. |
| 2005/0169893 A1 | 8/2005 | Koblish et al. |
| 2005/0170159 A1 | 8/2005 | Ramsey et al. |
| 2005/0171604 A1 | 8/2005 | Michalow |
| 2005/0177169 A1 | 8/2005 | Fisher et al. |
| 2005/0192672 A1 | 9/2005 | Wyss et al. |
| 2005/0203630 A1 | 9/2005 | Pope et al. |
| 2006/0015187 A1 | 1/2006 | Hunter et al. |
| 2006/0036331 A1 | 2/2006 | Lu et al. |
| 2006/0045903 A1 | 3/2006 | Kadiyala et al. |
| 2006/0106419 A1 | 5/2006 | Gingras |
| 2006/0116774 A1 | 6/2006 | Jones et al. |
| 2006/0147332 A1 | 7/2006 | Jones et al. |
| 2006/0241776 A1 | 10/2006 | Brown et al. |
| 2006/0241781 A1 | 10/2006 | Brown et al. |
| 2006/0254200 A1 | 11/2006 | Clarke et al. |
| 2007/0071733 A1 | 3/2007 | Kandel et al. |
| 2007/0142914 A1 | 6/2007 | Jones et al. |
| 2007/0150068 A1 | 6/2007 | Dong et al. |
| 2007/0156249 A1 | 7/2007 | Lawrynowicz et al. |
| 2007/0173948 A1 | 7/2007 | Meridew et al. |
| 2007/0203584 A1 | 8/2007 | Bandyopadhyay et al. |
| 2007/0225390 A1 | 9/2007 | Wang et al. |
| 2008/0004709 A1 | 1/2008 | O'Neill et al. |
| 2008/0050412 A1 | 2/2008 | Jones et al. |
| 2008/0071381 A1 | 3/2008 | Buscher et al. |
| 2008/0161927 A1 | 7/2008 | Savage et al. |
| 2008/0206862 A1 | 8/2008 | Asgari |
| 2008/0288083 A1 | 11/2008 | Axelsson et al. |
| 2009/0068245 A1 | 3/2009 | Noble et al. |
| 2009/0087605 A1 | 4/2009 | Ramsey et al. |
| 2009/0105772 A1 | 4/2009 | Seebeck et al. |
| 2009/0112315 A1 | 4/2009 | Fang |
| 2010/0057211 A1 | 3/2010 | Cuckler et al. |
| 2010/0137990 A1 | 6/2010 | Apatsidis et al. |
| 2010/0174377 A1 | 7/2010 | Heuer |
| 2010/0298950 A1 | 11/2010 | McDonnell et al. |
| 2011/0076316 A1 | 3/2011 | Sivananthan et al. |
| 2011/0200478 A1 | 8/2011 | Billiet et al. |
| 2011/0245930 A1 | 10/2011 | Alley et al. |
| 2011/0313532 A1 | 12/2011 | Hunt |
| 2012/0022662 A1 | 1/2012 | Conway et al. |
| 2012/0067853 A1 | 3/2012 | Wang et al. |
| 2012/0148987 A1 | 6/2012 | Dolabdjian et al. |
| 2012/0215310 A1 | 8/2012 | Sharp et al. |
| 2012/0245697 A1 | 9/2012 | Hunter et al. |
| 2013/0030529 A1 | 1/2013 | Hunt |
| 2013/0056912 A1 | 3/2013 | O'Neill et al. |
| 2013/0123935 A1 | 5/2013 | Hunt et al. |
| 2013/0158672 A1 | 6/2013 | Hunt |
| 2013/0218282 A1 | 8/2013 | Hunt |
| 2013/0268085 A1 | 10/2013 | Dong et al. |
| 2014/0058526 A1 | 2/2014 | Meridew et al. |
| 2014/0121776 A1 | 5/2014 | Hunt |
| 2014/0277548 A1 | 9/2014 | Cohen et al. |
| 2014/0288649 A1 | 9/2014 | Hunt |
| 2014/0288650 A1 | 9/2014 | Hunt |
| 2014/0343681 A1 | 11/2014 | Cohen et al. |
| 2015/0374882 A1 | 12/2015 | McDemus et al. |
| 2017/0095337 A1 | 4/2017 | Pasini et al. |
| 2018/0280140 A1 | 10/2018 | Jones et al. |
| 2018/0361510 A1 | 12/2018 | Stamp et al. |
| 2019/0133770 A1 | 5/2019 | Dion et al. |

FOREIGN PATENT DOCUMENTS

| | | |
|---|---|---|
| CN | 101301230 A | 11/2008 |
| CN | 102087676 A | 6/2011 |
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1993 |
| EP | 1247537 A1 | 10/2002 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1800700 A2 | 6/2007 |
| EP | 1806154 A1 | 7/2007 |
| EP | 1949989 A1 | 7/2008 |
| JP | 2255329 A | 10/1990 |
| JP | 4041794 A | 2/1992 |
| JP | 11287020 A | 10/1999 |
| JP | 11348045 A | 12/1999 |
| JP | 2001303751 A | 10/2001 |
| JP | 2003293012 A | 10/2003 |
| JP | 2006158953 A | 6/2006 |
| RU | 2218242 C2 | 12/2003 |
| WO | 9606881 A2 | 3/1996 |
| WO | 9824574 A1 | 6/1998 |
| WO | 9933641 A1 | 7/1999 |
| WO | 02085246 A2 | 10/2002 |
| WO | 2005084216 A2 | 9/2005 |
| WO | 2005080029 A1 | 9/2005 |
| WO | 2005087982 A1 | 9/2005 |
| WO | 2007058160 A1 | 5/2007 |
| WO | 2009116950 A1 | 9/2009 |
| WO | 2011002765 A2 | 1/2011 |
| WO | 2013006778 A2 | 1/2013 |

OTHER PUBLICATIONS

Chua, C.K. et al., "Development of a Tissue Engineering Scaffold Structure Library for Rapid Prototyping Part 2: Parametric Library and Assembly Program", 2003, Int J Adv Manuf Technology, Springer-Verlag. (Year: 2003).*

Heinl, Peter et al. "Cellular Ti-6Al-4V Structures with Interconnected Macro Porosity for Bone Implants Fabricated by Selective Electron Beam Melting", Apr. 10, 2008, Acta Biomaterialia 4, Elsevier Ltd. (Year: 2008).*

Cheah, Chi-Mun et al., "Automatic Algorithm for Generating Complex Polyhedral Scaffold Structures for Tissue Engineering", 2004, Tissue Engineering, vol. 10, No. 3/4. (Year: 2004).*

Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr_html.

Hollander et al., Structural mechanical and in vitro characterization of individually structured Ti-A1-4V produces by direct layer forming, Biomaterials, pp. 1-9, 2005.

Vureal et al., Plasma-sprayed oxide ceramics on steel substrates, Surface Coatings and Technology, 97 (1997) 347-354.

Patello-femoral Arthroplasty X-ray Results, Stryker Howmedica Osteonics, published on or before Apr. 5, 2011.

The Metals Handbook, Desk Edition, 2nd Edition, ASM International, 1998, p. 29.

Meiners et al., "Direct Generation of Metal Parts and Tools by Selective Laser Powder Remelting (SLPR)", W. Meiners, C. Over, K. Wissenbach, R. Poprawe, pp. 655-661 Austin, Texas, Aug. 9-11, 1999.

Hawley's Condensed Chemical Dictionary, 14th edition. John Wiley & Sons, 2002. Definition: sintering.

(56) References Cited

OTHER PUBLICATIONS

Dr. Kerron Harvey, producer, Research Intelligence, The University of Liverpool, Issue 13, Jun. 2002.
H.J. Niu and I.T.H. Chang, "Selective Laser Sintering of Gas and Water Atomized High Speed Steel Powders, " Scripta Materialia vol. 41, No. 1, (1999), pp. 25-30.
European Search Report and Written Opinion, EP05028133, dated May 11, 2010.
European Search Report and Written Opinion, EP10162970, dated Jun. 17, 2010.
R. Morgan, C.J. Sutcliffe, W. O'Neill, "Experimental investigatoin of nanosecond pulsed Nd:YAG laser re-melted pre-placed powder beds," Rapid Prototyping Journal, vol. 7, No. 3, 2001, pp. 159-172.
N.K. Vail, L.D. Swain, W.C. fox, T.B. Aufdlemorte, G. Lee, J.W. Barlow, "Materials for biomedical applications," Materials and Design, 20, 1999, pp. 123-132.
R.H. Morgan, A.J. Papworth, C. Sutcliffe, P. Fox, W. O'Neill, "High density net shape components by direct laser re-melting of single phase powders," Journal of Materials Science, 37, 2002, pp. 3093-3100.
European Search Report and Written Opinion, EP06127218, dated May 6, 2010.
PCT/US2008/008955 International Search Report and Written Opinion dated Dec. 2, 2008.
PCT/US2008/008955 International Preliminary Report on Patentability dated Feb. 4, 2010.
C.K. Chua et al. Development of a Tissue Engineering Scaffold Structure Library for Rapid Prototyping. Parts 1 and 2, International Journal of Advanced Manufacturing Technology, Feb. 2003, vol. 21, pp. 291-31.
Australian Examination Report for Application No. 2013202686 dated Aug. 7, 2014.
Chen, "3D Texture Mapping for Rapid Manufacturing", Computer-Aided Design and Applications, University of Southern California, vol. 4, No. 6, pp. 761-771, Jan. 1, 2007.
Engelbrecht et al., Cellular Structures for Optimal Performance, Georgia Institute of Technology & Paramount Industries, Inc., 2009.
Wang, Computer-Aided Design Methods for Additive Fabrication of Truss Structures, Georgia Institute of Technology, 2002.
Australian Examination Report for Application No. 2013202075 dated Feb. 13, 2015.
Canadian Office Action and Examination Search Report for Appln. No. 2,860,188 dated Jun. 4, 2015.
"Solid Freeform Fabrication", IEEE Spectrum, Feb. 1999, pp. 34-43.
Custom Design and Manufacturing of Canine Knee Implants,<http://www.lib.ncsu.edu/resolver/1840.16/670>, Issued Dec. 2, 2003.
Cheah et al., Automatic Algorithm for Generating Complex Polyhedral Scaffold Structures for Tissue Engineering, Tissue Engineering, vol. 10, No. 3/4, pp. 595-610, Mar. 2004.
Heinl et al., Cellular Ti-6Al-4V structures with interconnected macro porosity for bone implants fabricated by selective electron beam melting, Acta Biomaterialia, vol. 4, Issue 5, pp. 1536-1544, Sep. 2008.
Tuan et al, "Application of Micro CT and Computation Modeling in Bone Tissue Engineering", Computer-Aided Design, vol. 37, No. 11, Sep. 2005, pp. 1151-1161.
Akamaru et al., "Healing of Autologous Bone in a Titanium Mesh Case Used in Anterior Column Reconstruction After Total Spondylectomy", SPINE vol. 27, No. 13, 2002, pp. E329-E333.
McAfee et al., "Current Concepts Review: Interbody Fusion Cages in Reconstructive Operations on the Spine", The Journal of Bone and Joint Surgery, vol. 81, Issue 6, Jun. 1999, pp. 859-880.
Lin et al., "Interbody Fusion Cage Design Using Integrated Global Layout and Local Microstructure Topology Optimization", SPINE vol. 29, No. 16, pp. 1747-1754, Aug. 2004.
Williams et al., "CT evaluation of lumbar interbody fusion: Current concepts", AJNR Am J Neuroradiol 26:2057-2066, Sep. 2005.
Stephen D. Kuslich, MD, "Lumbar Interbody Cage Fusion for Back Pain: An Update on the Bak (Bagby and Kuslich) System", SPINE: State of the art reviews—vol. 13, No. 2, May 1999, pp. 295-311.
Zdeblick et al., "LT-CAGE—Lumbar Tapered Fusion Device—Surgical Technique", Medtronic Sofamor Danek, 25 pages, Copyright 2000.
Cheung et al., "Spinal Instrumentation Overview in Lumbar Degenerative Disorders: Cages", Chapter 26 / Spinal—Instrumentation Overview, Section IV/Surgery, Lumbar Spine: Official Publication of the International Society for the Study of the Lumbar Spine (3), 2004, pp. 286-291.
Kim et al., "Spinal Instrumentation Surgical Techniques", Thieme Medical Publishers, Inc., New York, NY, Copyright 2005, 41 pages.
Lin et al., "Structural and mechanical evaluations of a topology optimized titanium interbody fusion cage fabricated by selective laser melting process", Received Jan. 31, 2006, revised Aug. 25, 2006, accepted Dec. 2006, Published online Apr. 5, 2007 in Wiley Interscience (www.interscience.wiley.com). DOI: 10.1002/jbm.a.31231. 8 pages.
EP Office Communication on Third Party Observation for EP Application No. 05028133.6, dated Mar. 25, 2019, 67 pages.
Bobyn et al., "The optimum pore size for the fixation of porous-surfaced metal implants by the ingrowth of bone", Clinical Orthopaedics and Related Research, 150; 263-270 (1980).
Canadian Office Action for Application No. 2,529,884 dated Mar. 27, 2013.
Cunningham et al., "Design of Interbody Fusion Cages: Historical Considerations and Current Perspectives in Cage Technology", Surgical Techniques; Spinal Implants; Chapter 29-31, 2006, pp. 421-465.
EBI Learning Center Cafe flyer, EBI Spine EBI & Interpore Cross, NASS Booth 801, prior to Sep. 27, 2005, Philadelphia, PA.
European Examination Report for Application No. 10162970.7 dated Feb. 9, 2016.
European Examination Report for Application No. EP10162970.7 dated Aug. 4, 2017.
European Examination Report for Application No. EP10162970.7 dated Dec. 3, 2013.
Filiz et al., Int. Journal of Machine Tools & Manufacture, 48, 459-472, 2008.
Inter Fix Threaded Fusion Device, Important Medical Information, 14 pages.
Interlocutory Decision for Application No. EP 06125422.3 dated Nov. 14, 2012.
Notice of Opposition for EP Application No. 06125422.3 dated Jul. 4, 2011.
Protek Cementless Replacement of the Acetabulum by E. Morscher, published on or before Apr. 5, 2011.
Wang et al., "A Hybrid Geometric Modeling Method for Large Scale Conformal Cellular Structures," ASME Design Engineering Technical Conferences, Sep. 2005, 7 pages.
Third Party Observation for EP05028133.6 dated Mar. 25, 2019, 3 pages.
Third Party Observation for EP05028133.6 dated May 18, 2020, 3 pages.
Williams, et al., "Advances in Modeling the Effects of Selected Parameters on the SLS Process," Rapid Prototyping Journal, Jun. 1, 1998, pp. 90-100, vol. 4, No. 2.

* cited by examiner

FIG. 3

| METAL POWDER | MEAN OVERLAP (%) | | -500 | | | | | | | | | -250 | | | | | | | |
|---|---|---|---|---|---|---|---|---|---|---|---|---|---|---|---|---|---|---|---|
| | LASER SCANNING SPEED (mm/s) | | 100 | 120 | 140 | 160 | 180 | 200 | 220 | 240 | 260 | 100 | 120 | 140 | 160 | 180 | 200 | 220 | 240 |
| | SUBSTRATE | | | | | | | | | | | | | | | | | | |
| CoCr | Ti ALLOY | | | | | | | | | | | | | | | | | | |
| | CoCr | | | | | | | | | | | | | | | | | | |
| | STAINLESS STEEL | | ✓ | ✓ | ✓ | ✓ | ✓ | ✓ | ✓ | ✓ | ✓ | ✓ | ✓ | ✓ | ✓ | ✓ | ✓ | ✓ | ✓ |
| Nb | Ti ALLOY | | | | | | | | | | | | | | | | | | |
| | CoCr | | | | | | | | | | | | | | | | | | |
| | STAINLESS STEEL | | | | | | | | | | | | | | | | | | |
| Ta | Ti ALLOY | | | | | | | | | | | | | | | | | | |
| | CoCr | | | | | | | | | | | | | | | | | | |
| Ti | Ti ALLOY | | | | | | | | | | | | | | | | | | |
| | CoCr | | | | | | | | | | | | | | | | | | |

| | MEAN OVERLAP (%) | | -40 | | | | | | | | 25 | | | | | | | |
|---|---|---|---|---|---|---|---|---|---|---|---|---|---|---|---|---|---|---|
| 0 | LASER SCANNING SPEED (mm/s) | | 160 | 170 | 180 | 190 | 200 | 210 | 220 | 230 | 240 | 100 | 120 | 140 | 160 | 180 | 200 | 220 | 240 |
| | SUBSTRATE | | | | | | | | | | | | | | | | | | |
| CoCr | Ti ALLOY | | | | | | | | | | | ✓ | ✓ | ✓ | ✓ | ✓ | ✓ | ✓ | ✓ |
| | CoCr | | | | | | | | | | | ✓ | ✓ | ✓ | ✓ | ✓ | ✓ | ✓ | |
| | STAINLESS STEEL | | | | | | | | | | | ✓ | ✓ | ✓ | ✓ | ✓ | ✓ | ✓ | ✓ |
| Nb | Ti ALLOY | | ✓ | ✓ | ✓ | ✓ | ✓ | ✓ | ✓ | ✓ | ✓ | | | | | | | | |
| | CoCr | | ✓ | ✓ | ✓ | ✓ | ✓ | ✓ | ✓ | ✓ | ✓ | | | | | | | | |
| | STAINLESS STEEL | | ✓ | ✓ | ✓ | ✓ | ✓ | ✓ | ✓ | ✓ | ✓ | | | | | | | | |
| Ta | Ti ALLOY | | ✓ | ✓ | ✓ | ✓ | ✓ | ✓ | ✓ | ✓ | ✓ | | | | | | | | |
| | CoCr | | ✓ | ✓ | ✓ | ✓ | ✓ | ✓ | ✓ | ✓ | ✓ | | | | | | | | |
| Ti | Ti ALLOY | | ✓ | ✓ | ✓ | ✓ | ✓ | ✓ | ✓ | ✓ | ✓ | | | | | | | | |
| | CoCr | | ✓ | ✓ | ✓ | ✓ | ✓ | ✓ | ✓ | ✓ | ✓ | | | | | | | | |

| | MEAN OVERLAP (%) | | 50 | | | | | | | | | 50 | | | | | | | |
|---|---|---|---|---|---|---|---|---|---|---|---|---|---|---|---|---|---|---|---|
| 0 | LASER SCANNING SPEED (mm/s) | | 100 | 120 | 140 | 160 | 180 | 200 | 220 | 240 | 260 | 280 | 300 | 320 | 340 | 360 | 380 | 400 | 420 |
| | SUBSTRATE | | | | | | | | | | | | | | | | | | |
| CoCr | Ti ALLOY | | | | | | | | | | | | | | | | | | |
| | CoCr | | | | | | | | | | | | | | | | | | |
| | STAINLESS STEEL | | ✓ | ✓ | ✓ | ✓ | ✓ | ✓ | ✓ | ✓ | ✓ | ✓ | ✓ | ✓ | ✓ | ✓ | ✓ | ✓ | ✓ |
| Nb | Ti ALLOY | | | | | | | | | | | | | | | | | | |
| | CoCr | | | | | | | | | | | | | | | | | | |
| | STAINLESS STEEL | | ✓ | ✓ | ✓ | ✓ | ✓ | ✓ | ✓ | ✓ | ✓ | | | | | | | | |
| Ta | Ti ALLOY | | | | | | | | | | | | | | | | | | |
| | CoCr | | | | | | | | | | | | | | | | | | |
| Ti | Ti ALLOY | | | | | | | | | | | | | | | | | | |
| | CoCr | | | | | | | | | | | | | | | | | | |

FIG. 27
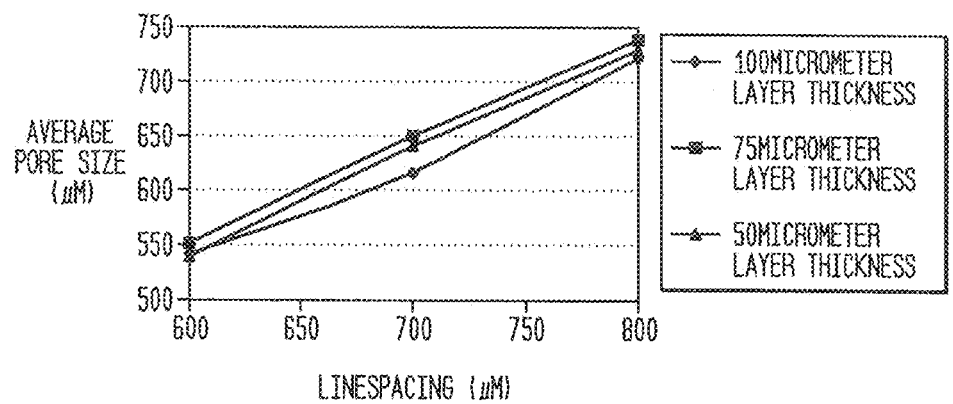
FIG. 28A  FIG. 28B  FIG. 28C
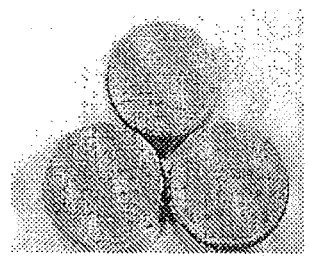 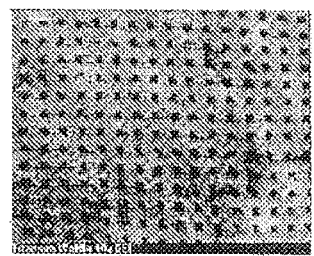 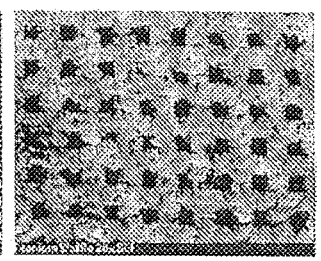
FIG. 28D  FIG. 28E  FIG. 28F
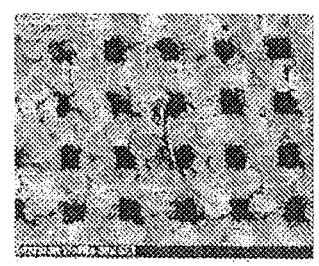  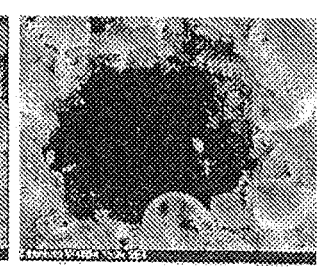

LASER-PRODUCED POROUS SURFACE

CROSS-REFERENCE TO RELATED APPLICATIONS

The present application is a continuation of U.S. patent application Ser. No. 14/671,545 filed Mar. 27, 2015 which is a continuation of U.S. patent application Ser. No. 13/605,354 filed Sep. 6, 2012, which is a continuation-in-part of U.S. patent application Ser. No. 12/843,376, now U.S. Pat. No. 8,268,100, filed Jul. 26, 2010, which is a continuation of U.S. patent application Ser. No. 12/386,679, now U.S. Pat. No. 8,268,099, filed Apr. 22, 2009, which is a continuation of U.S. patent application Ser. No. 10/704,270, now U.S. Pat. No. 7,537,664, filed Nov. 7, 2003, which claims the benefit of U.S. Provisional Application No. 60/424,923 filed Nov. 8, 2002, and U.S. Provisional Application No. 60/425,657 filed Nov. 12, 2002. U.S. patent application Ser. No. 13/605,354 is also a continuation of U.S. patent application Ser. No. 12/846,327 filed Jul. 29, 2010, which is a continuation of U.S. patent application Ser. No. 11/027,421, now abandoned, filed Dec. 30, 2004. The entire disclosures of all of the above-mentioned applications are incorporated by reference herein.

BACKGROUND OF THE INVENTION

The present invention relates to a porous surface and a method for forming the same, which uses a directed energy beam to selectively remelt a powder to produce a part. The energy beam may include a laser beam, and an electron beam or the like. In particular, this invention relates to a computer-aided laser apparatus, which sequentially remelts a plurality of powder layers to form unit cells to build the designed part in a layer-by-layer fashion. The present application is particularly directed toward a method of forming a porous and partially porous metallic structure.

DESCRIPTION OF THE RELEVANT ART

The field of free-form fabrication has seen many important recent advances in the fabrication of articles directly from computer controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to engineering drawings.

One example of a modern rapid prototyping technology is the selective laser sintering process practiced by systems available from DTM Corporation of Austin, Tex. According to this technology, articles are produced in layer-wise fashion from a laser-fusible powder that is dispensed one layer at a time. The powder is fused, remelted or sintered, by the application of laser energy that is directed in raster-scan fashion to portions of the powder layer corresponding to a cross section of the article. After the fusing of the powder in each layer or on one particular layer, an additional layer of powder is dispensed, and the process repeated, with fusion taking place between the current layer and the previously laid layers until the article is complete. Detailed descriptions of the selective laser sintering technology may be found in U.S. Pat. Nos. 4,863,538, 5,017,753, 5,076,869 and 4,944,817. Quasi-porous structures have also been developed in the form of regular and irregular lattice arrangements in which individual elements (column and connecting cross-members) are constructed singularly from a pre-defined computer-aided design model of the external geometry and lattice structure. The selective laser remelting and sintering technologies have enabled the direct manufacture of solid or dense three-dimensional articles of high resolution and dimensional accuracy from a variety of materials including wax, metal powders with binders, polycarbonate, nylon, other plastics and composite materials, such as polymer-coated metals and ceramics.

The field of the rapid prototyping of parts has, in recent years, made large improvements in broadening high strain, high density, parts for use in the design and pilot production of many useful articles, including metal parts. These advances have permitted the selective laser remelting and sintering processes to now also be used in fabricating prototype tooling for injection molding, with expected tool life in access of ten thousand mold cycles. The technologies have also been applied to the direct fabrication of articles, such as molds, from metal powders without a binder. Examples of metal powder reportedly used in such direct fabrication include two-phase metal powders of the copper-tins, copper-solder (the solder being 70% led and 30% tin), and bronze-nickel systems. The metal articles formed in these ways have been quite dense, for example, having densities of up to 70% to 80% of fully dense (prior to any infiltration). Prior applications of this technology have strived to increase the density of the metal structures formed by the remelting or sintering processes. The field of rapid prototyping of parts has focused on providing high strength, high density, parts for use and design in production of many useful articles, including metal parts.

However, while the field of rapid prototyping has focused on increasing density of such three-dimensional structures, the field has not focused its attention on reducing the density of three-dimensional structures. Consequently, applications where porous and partially porous metallic structures, and more particularly metal porous structures with interconnected porosity, are advantageous for use have been largely ignored. The present invention is equally adapted for building porous structure having a high density or a low density. It is an object of this invention to use a laser and powder metal to form pores in structures in which pores are irregular in size and have a controlled total porosity. It is a further object to produce porous tissue in growth surfaces with interconnected porosity with uniform pores and porosity.

SUMMARY OF THE INVENTION

The present invention relates to a method for producing a three-dimensional porous structure particularly for use with tissue ingrowth. In one embodiment of the present invention, a layer of metallic powder is deposited onto a substrate or a build platform. Preferred metals for the powder include titanium, titanium alloys, stainless steel, cobalt chrome alloys, tantalum or niobium. A laser beam with predetermined settings scans the powder layer causing the powder to preferentially remelt and consequently solidify with a decreased density, resulting from an increase in porosity as compared to a solid metal. The range of the laser's power may be between 5 W and 1000 W. After the first layer of powder has been completed, successive offset layering and remelting are continued until the porous part has been successfully completed. In this embodiment, the benefit of the part formed is that that decreased density increases porosity thus enabling the part to be used for, among other things, tissue ingrowth.

In a second embodiment, the first layer of metallic powder is deposited onto a solid base or core and fused thereto. Preferred metals used for the core include titanium, titanium alloys, stainless steel, cobalt chrome alloys, tantalum and niobium. Successive powder layers of the same or different materials are once again added in a layer-by-layer fashion until the part is completed. This embodiment has the desired effect of providing a structure in which the porosity may be increased as the structure is built, resulting in a graded profile in which the mechanical properties will also be reduced outwards from the core. This will allow the formed part to be used for, among other things, medical implants and prosthesis, but yet still include a surface for tissue ingrowth.

The method of producing a three-dimensional porous tissue ingrowth structure may include depositing a first layer of a powder made from a metal selected from the group consisting of titanium, titanium alloys, stainless steel, cobalt chrome alloys, tantalum and niobium, onto a substrate. Followed by scanning a laser beam at least once over the first layer of powder. The laser beam having a power (P) in Joule per seconds with a scanning speed (v) in millimeters per second with a range between 80 and 400 mms. and a beam overlap (b) in millimeters of between 50% and −1200%. Such that the number calculated by the formula P/(b×v) lies between the range 0.3-8 J/mm$^2$.

At least one additional layer of powder is deposited and then the laser scanning steps for each successive layer are repeated until a desired web height is reached. In a second embodiment, during the step of repeating the laser scanning steps, at least one laser scan is carried out angled relative to another laser scan in order to develop an interconnecting or non-interconnecting porosity.

The thickness of the first layer and said successive layers of powder is between 5 µm-2000 µm. The laser can be applied either continuously or in a pulse manner, with the frequency of the pulse being in the range of approximately 1 KHz to 50 KHz. Preferably, the method is carried out under an inert atmosphere, more preferably specifically an Argon inert atmosphere.

In order to achieve a greater mechanical strength between the base or core and the first layer of powder a third metal may be used to act as an intermediate. The third metal would act as a bond coat between the core and first layer of powder. Additionally, the core may be integral with the resultant porous ingrowth structure and impart additional physical properties to the overall construct. The core may also be detachable from the resultant porous surface buildup.

It is the object of the present invention to provide a method of fabricating porous and partially porous metallic structures with a known porosity for use in particularly but not exclusively hard or soft tissue interlock structures or medical prosthesis.

These and other objects are accomplished by a process of fabricating an article in which laser-directed techniques are used to produce a porous three-dimensional structure with interconnected porosity and predetermined pore density, pore size and pore-size distribution. The article is fabricated, in the example of remelting, by using a laser and varying either the power of the laser, the layer thickness of the powder, laser beam diameter, scanning speed of the laser or overlap of the beam. In fabricating a three-dimensional structure, the powder can be either applied to a solid base or not. The article is formed in layer-wise fashion until completion.

The present invention provides a method for building various structures and surfaces but specifically medical implants. The structures are built in a layer-by-layer fashion with individual layers including portions of predetermined unit cells.

In one embodiment of the present invention, a layer of metal powder is deposited on a substrate. The substrate may be a work platform or a base, with the base or core being provided to possibly be an integral part of the finished product. After an individual layer of powder is deposited a scanning process may be preformed to selectively melt the powder to form portions of a plurality of predetermined unit cells. The scanning process includes scanning a laser beam onto the metal powder.

As successive layers are deposited and scanned a structure is built form one end to an opposite end. The structure includes a plurality of predetermined unit cells. The unit cells provide the structure with interconnecting pores as well as porosity. The size of the pores and porosity as well as other factors may all be predetermined.

In one preferred embodiment the size of the pores of the porosity of the built structure are specifically chosen to provide the structure with characteristics similar to medical implants.

In one aspect of the present invention disclosed is a method of producing a three-dimensional porous tissue in-growth structure. The method preferably includes depositing a first layer of a powder made from a metal selected from the group consisting of titanium, titanium alloys, stainless steel, cobalt chrome alloys, tantalum and niobium onto a substrate. The layer of powder is than scanned using a laser beam. The laser beam has a power, and scans the powder layer for a period of time with a point distance. The power of the laser beam is preferably within the range of 5 to 1000 watts although the present invention may be adapted for different power ranges. Additionally, in a preferred embodiment, the exposure time is in a range between 100 µsec to 1000 µsec. The laser beam scans the powder layer to form a portion of a plurality of predetermined unit cells. The predetermined unit cells include struts having cross-sectional dimensions. The cross-section of the struts may be any regular of irregular shape. A few such examples include circular, rectangular, cubic cross-sections or the like.

In one preferred embodiment of the present invention the laser power is 90.5 W, the exposure time is 1000 µsec and the point distance is 90 µm.

The method also preferably includes depositing at least one additional layer of the powder onto the first layer and repeating the step of scanning the additional layers with a laser beam for at least one of the deposited layers in order to continuing forming the predetermined unit cells.

The predetermined unit cells make take the shape of most regular or irregular structure. For example, the unit cells may be in the shape of a tetrahedron, dodecahedron or octahedron as well as other symmetrical structures. As mentioned, the unit cells may not have such uniformity and have an irregular shape. The unit cells may also be truncated, which includes eliminating some of the struts, which form a unit cell. Truncated unit cells located at the exterior surface of a built product provide a barbed effect to the product.

In a preferred embodiment of the present invention, the layers of metal powder have a thickness between 5 µm to 2000 µm.

The present invention may also include predetermining a porosity range for at least one deposited powder layer and scanning the layer in a manner to provide the deposited layer with porosity within the predetermined porosity range.

In one aspect of the present invention, the substrate may include a base, core, work platform or the like. As with the layer of powder, the metal selected to form the base or core may be selected from the group consisting of titanium, titanium alloys, stainless steel, cobalt chrome alloys, tantalum and niobium. Portions of the powder layers may be fused and or sintered to the base or core. The base or core may either be separated from the finished built product or may be an integral part of the finished product. If the base or core is an integral part of the finished product it may impart additional physical properties to the overall construct. The base or core may be constructed using the present invention.

In one aspect of the present invention a solid or semipervious layer may be placed between the substrate and the first deposited powder layer.

In another aspect of the present invention during the at least one of the steps of the scanning process, a plurality of satellites may be formed on portions of the predetermined unit cells. The satellites may remain attached to the predetermined unit cells so as to affect the porosity of the structure. In an alternate embodiment, the satellites may be removed. One way to remove the satellites is by an acid etching process. The acid etching process may be conducted not only to remove some of all of the satellites but also to alter the cross-sectional dimensions of various struts forming the predetermined unit cells.

In another aspect of the present invention, a plurality of struts may intersect at an intersection point. Either prior to completion of after completion of the finished structure, various intersection points may be sintered. In one reason for sintering the intersection points is to eliminate any unmelted metal powder spots.

In a preferred aspect of the present invention, the laser beam may be adjusted to modify the length and/or cross-section of various struts. Additionally, at least some of the unit cells may be deformed so as to drape over the substrate. Laser beam compensation may also be employed. Some of the struts of the unit cells may overlap struts of other unit cells. This aspect also enables the adjusting of the porosity throughout the completed structure.

At least some of the predetermined unit cells may be coated with unmelted metal particles.

In one aspect of the present invention the metal powder layers are deposited and scanned in order to form a medical implant. The medical implant preferably having porosity within a predetermined range. The medical implant may include an acetabular cup, acetabular shell, a knee implant, femoral or hip implant or the like. The constructed medical implant may have a porosity, which promotes bone in-growth and/or provides the medical implant with soft tissue characteristics.

The medical implants, as well as other constructed structures, may be provided with an attaching mechanism for anchoring or at least more firmly attaching the medical implant to another element. One such example is an acetabular shell being provided with a rim to snap-fit to an acetabular cup.

In another aspect of the invention, the structure may be subjected to a hot isostatic pressing.

In one preferred embodiment of the present invention, the method of producing a three-dimensional construct includes loading a file of a component into an engineering design package. The component is scaled down in the file from its original size. A Boolean operation is next performed to subtract the scaled down component from the original component. This creates a jacket. The jacket can than be processed using a bespoke application that populates the jacket with a repeating open cellular structure.

The open cellular structure is than sliced using the bespoke application to a predetermine thickness.

The main body of the file component jacket is loaded into a user interface program and the jacket is sliced into layers having a predetermined thickness. Hatching is than applied to the file component jacket as required to build a construct and the jacket is merged with the open cellular lattice structure. Once a representation has been obtained the depositing and scanning steps of the present invention may be conducted to build the final product.

BRIEF DESCRIPTION OF THE DRAWINGS

Methods of forming the porous surface of the present invention can be performed in many ways and some embodiments will now be described by way of example and with reference to the accompanying drawings in which:

FIG. 3 is a table showing a series of parameters used for the samples of FIG. 2;

FIG. 27 shows the effect of line spacing on pore size.

FIG. 28A-28F are examples of typical waffle structures.

DETAILED DESCRIPTION OF THE INVENTION

Figure 1:
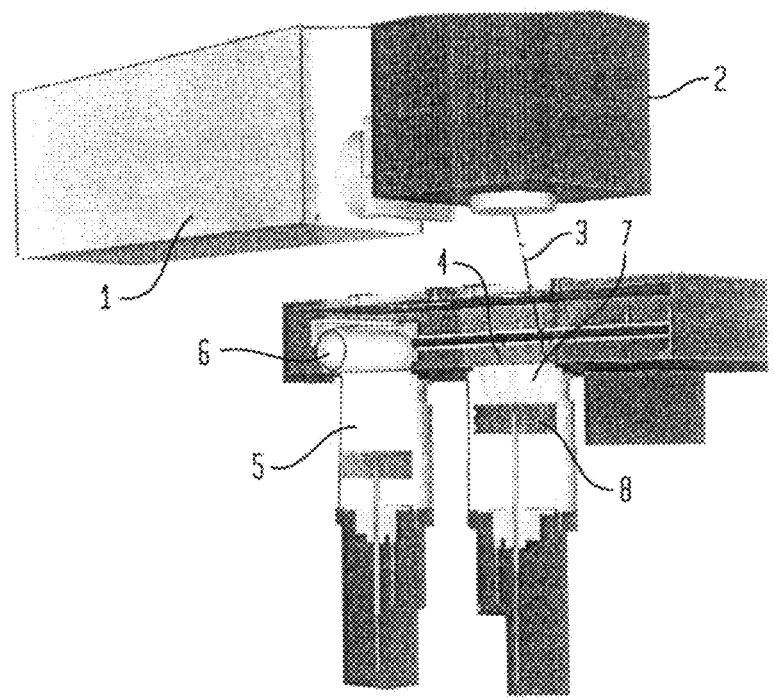
FIG. 1 is a diagrammatic illustration of the apparatus used to make test samples according to the processes of the present invention.

The present invention relates to a method of forming porous and partially porous metallic structures which are particularly but not exclusively applicable for use in hard or soft tissue interlock structures for medical implants and prosthesis. The method makes use of laser technology by employing a variety of scanning strategies. Typical metal and metal alloys employed include stainless steel, cobalt chromium alloys, titanium and its alloys, tantalum and niobium, all of which have been used in medical device applications. The present invention can be used for such medical device applications where bone and soft tissue interlock with a component is required, or where a controlled structure is required to more closely match the mechanical properties of the device with surrounding tissue. Additionally, the present invention may be employed to enhance the biocompatibility of a porous structure with animal tissue. With these advantages in mind, a structure may be created using specific dimensions required to accommodate a particular patient.

One particular intention of the present invention is to produce a three-dimensional structure using a laser remelting process, for example, for building structures with or without a solid base or core. When applied to an orthopedic prosthesis, the three-dimensional structure could be used to provide a porous outer layer to form a bone in-growth structure. Alternatively, the porous structure, when applied to a core, could be used to form a prosthesis with a defined stiffness to both fulfill the requirement of a modulus match with surrounding tissue and provide interconnected porosity for tissue interlock. A further use could be to form an all-porous structure with grade pore size to interact with more than one type of tissue. Again, the process can be used to build on a solid base or core with an outer porous surface, the porosity of which is constant or which varies. The base or core materials to which the process is applied may be either titanium and its alloys, stainless steel, cobalt chrome alloys, tantalum or niobium as well as any other suitable material. The preferred surface coatings are titanium, cobalt chrome and tantalum but both stainless steel and niobium can also be used as well as any other suitable material. Fully porous structures may be built from any of the materials tested, with the preferred material being titanium. One intention of the present invention is to produce a method which can be exploited on a commercial basis for the production of, for example, bone interlock surfaces on a device although it has many other uses.

According to the present invention, a method of forming a three-dimensional structure includes building the shape by laser melting powdered titanium and titanium alloys, stainless steel, cobalt chrome alloys, tantalum or niobium using a continuous or pulsed laser beam. Individual layers of metal are scanned using a laser. The laser may be a continuous wave or pulsed laser beam. Each layer or portion of a layer is scanned to create a portion of a plurality of predetermined unit cells, as will be described below. Successive layers are deposited onto previous layers and also may be scanned. The scanning and depositing of successive layers continues the building process of the predetermined unit cells. As disclosed herein, by continuing the building process refers not only to a continuation of a unit cell from a previous layer but also a beginning of a new unit cell as well as the completion of a unit cell.

The method can be performed so that the structure is porous and if desired, the pores can be interconnecting to provide an interconnected porosity.

If desired, the method can include using a base or core of cobalt chrome alloy, titanium or alloy, stainless steel, niobium and tantalum, on which to build a porous layer of any one of the aforementioned metals and alloys by laser melting using a continuous or pulsed laser beam. Thus, a mixture of desired mixed materials may be employed.

The method can be applied to an existing article made from cobalt chrome, titanium or titanium alloys, stainless steel, tantalum or niobium, such as an orthopedic implant, to produce a porous outer layer from any of the aforementioned metals or alloys to provide a bone in-growth structure.

Preferably, prior to the deposition of any powder onto a substrate, a cleaning operation to ensure a contaminant-free surface may be employed. Typically, this process may include a solvent wash followed by a cleaning scan of the laser beam without the presence of particles.

In order to increase the mechanical bond between a substrate i.e., core or base, and a first layer of deposited powder a coating process may be employed. The coating process includes applying a third metal directly to the substrate, which has a higher bond strength to the substrate then does the first layer of powder. This process is particularly useful when the substrate and first powder layer are of different materials. The process of coating the substrate may be accomplished using known processes including laser deposition, plasma coating, cold gas dynamic spraying or similar techniques. One example of the coating process includes using either niobium or tantalum as an interface between a cobalt chrome alloy substrate and a first layer of titanium powder.

The present invention can include a laser melting process, which precludes the requirement for subsequent heat treatment of the structure, thereby preserving the initial mechanical properties of the core or base metal. The equipment used for the manufacture of such a device could be one of many currently available including the MCP Realiszer, the EOS M270, Trumpf Trumaform 250, the Arcam EBM S12 and the like. The laser may also be a custom produced laboratory device.

The method may be applied to produce an all-porous structure using any of the aforementioned metal or metal alloys. Such structures can be used as finished or final products, further processed to form a useful device for bone or soft tissue in-growth, or used to serve some other function such as that of a lattice to carry cells, for example.

The pore density, pore size and pore size distribution can be controlled from one location on the structure to another. It is important to note that successive powder layers can differ in porosity by varying factors used for laser scanning powder layers. As for example, a first layer of powder is placed and subsequently scanned. Next a second layer of powder is placed and scanned. In order to control porosity the second scan may be angled relative to the first scan. Additionally, the angling of the scanning as compared to previous and post scans may be maneuvered and changed many times during the process of building a porous structure. If a structure was built without alternating the angling of any subsequent scans you would produce a structure having a plurality of walls rather than one with an interconnecting or non-interconnecting porosity.

In one such method, the laser melting process includes scanning the laser beam onto the powder in parallel scan lines with a beam overlap i.e., scan spacing, followed by similar additional scans or subsequent scans at 90°. The type of scan chosen may depend on the initial layer thickness as well as the web height required. Web height refers to the height of a single stage of the porous structure. The web height may be increased by deposited additional layers of powder of a structure and scanning the laser at the same angle of the previous scan.

Further, the additional scan lines may be at any angle to the first scan, to form a structure with the formation of a defined porosity, which may be regular or random. The scan device may be programmed to proceed in a random generated manner to produce an irregular porous construct but with a defined level of porosity. Furthermore, the scan can be pre-programmed using digitized images of various structures, such as a trabecular bone, to produce a similar structure. Contrastingly, the scan may be pre-programmed using the inverse of digitized images, such as the inverse of a digitized trabecular bone to produce trabecular shaped voids. Many other scanning strategies are possible, such as a waffle scan, all of which can have interconnecting porosity if required.

The beam overlap or layer overlap may be achieved by rotation of the laser beam, the part being produced, or a combination of both.

A first method according to the present invention is intended to produce a porous structure for bone in-growth on the outer surface layer of a prosthesis. To produce a porous surface structure, the nature of the material formed as a result of laser melting of powdered beads is principally dependent on the thermal profile involved (heating rate, soaking time, cooling rate); the condition of the raw material (size and size distribution of powder particles); atmospheric conditions (reducing, inert or oxidizing chamber gas) In some instances, the nature of the material formed may be further a result of accurate control of the deposited layer thickness.

There have been a number of studies to determine the optimum pore structure for maximization of bone in-growth on prostheses. The general findings suggest that optimum porosity is between approximately 20% and 40%, and aim to mid value with a mean volume percent of voids of about 70%. The preferred pore structure is interconnected, with a minimum pore size between about 80 μm and 100 μm and a maximum pore size between 80 μm and 800 μm. The structured thickness for in-growth is 1.4-1.6 mm, but can be larger or smaller depending on the application. As for example, it may be necessary to produce even smaller pore sizes for other types of tissue interaction or specific cellular interaction.

The first phase of development of the present invention involved an investigation, designed to characterize the material transformation process and to identify the optimum parameters for processing using three substrate materials CoCr and Ti stainless steel alloys, with five powder types Ti, CoCr, Ta and Nb, stainless steel.

The initial Direct Laser Remelting trials explored a comprehensive range of process parameters during the production of a number of coated base substrates. Results from this task were evaluated using laser scanning and white light interferometry in order to define the range of process parameters that produced the optimum pore structure.

Referring to FIG. 1, there is shown the apparatus used to carry out the method which comprises an Nd; YAG industrial laser 1 manufactured by Rofin Sinar Lasers, in Hamburg, Germany, integrated to an RSG1014 analogue galvo-scanning head 2 providing a maximum scan speed of 500 mm/s. The laser beam 3 is directed into an atmospherically controlled chamber 4, which consists of two computer-controlled platforms for powder delivery and part building. The powder is delivered from a variable capacity chamber 5 into the chamber 4 and is transported by a roller 6 to a build platform 7 above a variable capacity build chamber 8. In the embodiment shown in FIG. 1, the build and delivery system parameters are optimized for an even 100 μm coating of powder to be deposited for every build layer. The metals chosen as surface materials are all difficult to process due to their affinity for oxygen. Cr and Ti are easily oxidized when processed by laser in oxygen-containing atmosphere, their oxide products have high melting points and poor flowability. For this reason, and to prevent the formation of other undesirable phases, the methods were carried out under an Argon inert atmosphere in chamber 8. Pressure remained at or below atmospheric pressure during the entire application.

The build chamber 8 illustrated in FIG. 1 and method of layering described above is suitable for test specimens and constructs such as three-dimensional freestanding structures. However, in order to build on to an existing device, such as acetabular metal shells, hip and knee femoral components, knee tibial components and other such devices, considerable changes to the powder laying technique would need to be applied.

Preliminary experiments were performed on CoCr alloy to determine the efficacy of in-situ laser cleaning of the substrate. Typical processing conditions were: Laser power of 82 W, pulse frequency of 30 KHz, and a laser scan speed of 160 mm/sec.

Preliminary experiments were performed on CoCr to assess the environment conditions within the chamber. In these examples, Co212-e Cobalt Chrome alloy was used. The CoCr was configured into square structures, called coupons. Arrays of CoCr coupons were built onto a stainless steel substrate. The Co212-e Cobalt Chrome alloy had a particle size distribution of 90<22 urn, i.e., 90% of the particles are less than 22 μm, the composition of which is shown in the table below.

TABLE 1

Composition of Co212-e CoCr alloy

| Element | Cr | Mo | Si | Fe | Mn | Ni | N | C | Co |
|---|---|---|---|---|---|---|---|---|---|
| Wt % | 27.1 | 5.9 | 0.84 | 0.55 | 0.21 | 0.20 | 0.16 | 0.050 | Balance |

Figure 2:
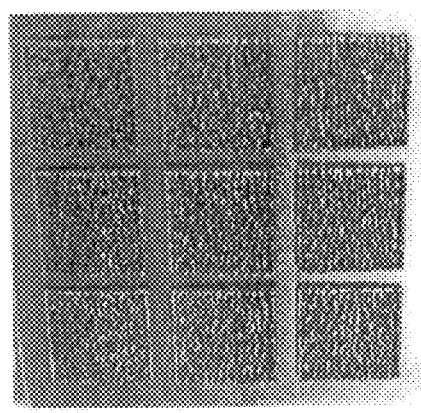
FIG. 2 is a photographic image showing an array of samples produced by the processes as performed by the apparatus of FIG. 1.

An array of nine sample coupons were produced as shown in FIG. 2, with the process of Table 2, using a maximum laser power of 78 watts (W) and laser scanning speed for each coupon varying between 100-260 mms$^{-1}$. Of course a higher laser power may be employed; however, a higher laser power would also necessitate increasing the speed of the laser scan speed in order to produce the desired melting of the powder layer. A simple linear x-direction scan was used on each of the coupons. This allowed the processing parameter, beam overlap, to be used to control the space between successive scan lines. That is, with a 100 μm laser spot size, an overlap of −200% produces a 100 μm gap between scans. Although the acceptable range for the beam overlap is given at +50% to −1200% it should be duly noted that the negative number only refers to the fact the there is a gap as opposed to a beam overlap between successive scans. For instance a beam overlap of zero refers to the fact that successive scans on the same layer of powder border each other. If the beam overlap was 5% then 5% of the first scan is overlapped by the second scan. When computing the Andrew number the absolute value of the beam overlap is used. The complete set of process parameters used is shown in Table 2 below.

TABLE 2

| | Process parameters | | | | | |
|---|---|---|---|---|---|---|
| Power Watts (W) | Layer Thickness (μm) | Beam Diameter (μm) | Scanning Speed (mms$^{-1}$) | Atmosphere | No. of Layers | Overlap (% of line width) |
| 78 | 100 | 100 | 100-260 | No | 16 | 25, 50, −500 |

The incremental changes in scanning speed and the size of the speed range were modified as the experiments progressed. To begin with, a large range of speeds was used to provide an initial indication of the material's performance and the propensity to melt. As the experiments progressed, the range was reduced to more closely define the process window. Speed and beam overlap variations were used to modify the specific energy density being applied to the powder bed and change the characteristics of the final structure. The complete series of parameters are given in FIG. 3, the parameters sets used for the definitive samples are shaded in gray.

CoCr was the first of four powders to be examined and, therefore, a wide range of process parameters was used. In each case, laser power and the pulse repetition rate were kept constant, i.e., continuous laser pulse, to allow the two remaining parameters to be compared. Layer thickness was maintained at 100 μm throughout all the experiments described here. Layer thickness can, however, vary between 5 μm to 2000 μm.

On completion of the initial series of experiments using CoCr powder on 2.5 mm thick stainless steel substrates, basic optical analysis was conducted of the surface of the coupons to ascertain the size of the pores and degree of porosity being obtained. Once a desired pore size was obtained and the coupons had suitable cohesion, the two experiments closest to the optimum desired pore size were repeated using first CoCr and then Ti substrates. The same structure could be obtained by other parameters.

Following the conclusion of the CoCr experiments, the remaining three powders; Niobium, Tantalum and Titanium were investigated in turn. The procedure followed a simple course although fewer parameter sets were explored as the higher melting points of these materials forced the reduction in speeds compared to CoCr powder.

For Niobium, the particle size description was 80%<75 μm at a purity of 99.85%. Due to its higher melting temperature compared to that of CoCr (Nb being at about 2468° C., and CoCr being at about 1383° C.), the laser parameters used included a reduced scanning speed range and increased beam overlap providing increased specific energy density at the powder bed. In addition, the pulse repetition rate was varied from 20 kHz to 50 kHz.

On completion of a small number (four in total) of preliminary experiments of Nb on stainless steel substrate, the experiment with the most ideal parameters was repeated on both the CoCr and Ti substrates.

The Tantalum used in this study had a particular size distribution of 80%<75 μm with a purity of 99.85%. Ta has a melting point of about 2996° C. and was processed using the same laser parameters as Nb. Now confident of the atmospheric inertness, the Ta powder was melted directly onto the CoCr and Ti substrates.

Bio-medical alloys of Titanium were not readily available in powder form and so pure Ti was chosen. The particle size distribution for the Ti powder was 80%<45 μm with a purity of 99.58%. The same parameters used for Nb and Ta were also used for the Ti powder. Ti has a lower melting point than Ta or Nb, Ti being at about 1660° C., but has a higher thermal conductivity than Ta or Nb. This implies that although the powder should require less energy before melting, the improved heat transfer means a larger portion of the energy is conducted away from the melt pool.

Following the completion of samples with all four powders on the required substrates, surface analysis was conducted using optical analysis and a scanning electron microscope to obtain images of the resultant pores. Porosity was calculated using a simple image processing technique involving the setting of contrast thresholds and pixel counting. While this technique is not the most accurate method, it allows the rapid analysis of small samples produced. Techniques such as Xylene impregnation would yield more accurate results but they are time consuming and require larger samples than those produced here.

Following an extended series of experimentation, two sets of laser processing parameters were selected for the laser melting of CoCr powder. From analysis of the stainless steel substrates, it was seen that a large portion of the results fell within the pore size required for these materials, stated as being in the range of 80 μm to 400 μm.

Optical analysis of the surface structure of each of the coupons produced with CoCr on CoCr and Ti alloy substrates were initially viewed but due to problems with the depth of field associated with an optical microscope, little information could be extracted. In addition to the coupons that were produced to satisfy the project requirements, two experiments were conducted using a relatively large negative beam overlap of −250 and −500%. Optical images of the coupon's surface and in section are shown in FIG. 4. These were not the definitive parameters chosen for the final arrays on CoCr and Ti alloy substrates as the pore size exceeds the required 80 μm to 400 μm. They are shown here to display what the Direct Laser Remelting process can produce when an excessive beam overlap is used.

Figure 5A:
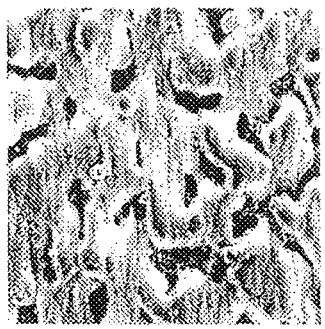
Figure 5B:
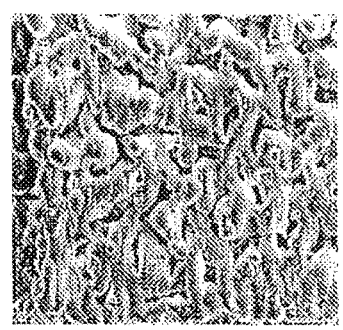
Figure 6A:
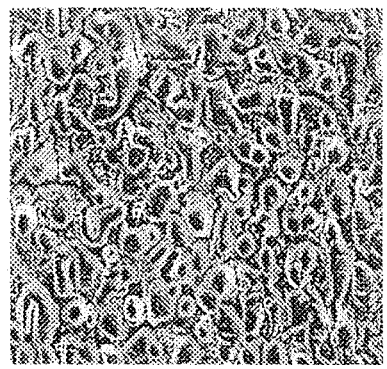
Figure 6B:
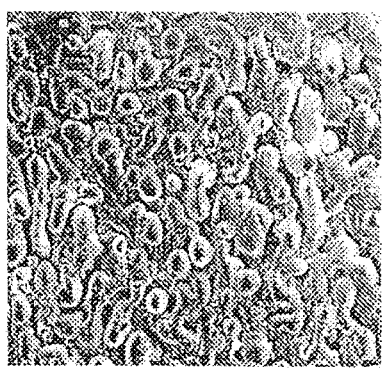
Figure 6C:
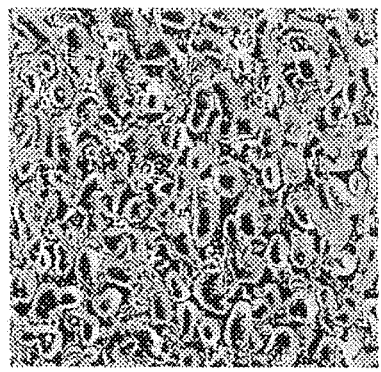
Figure 6D:
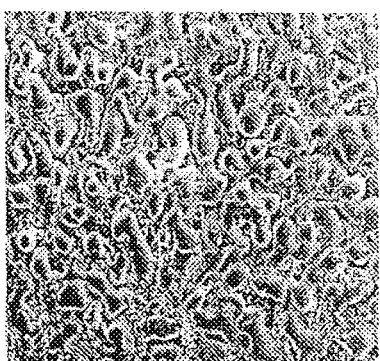
Figure 6E:
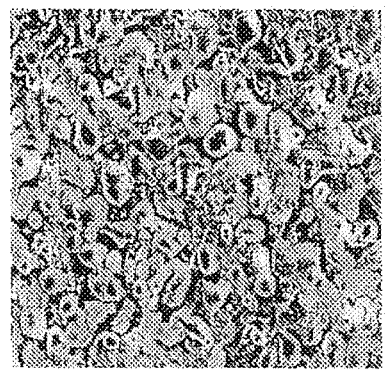

To provide a clearer indication of the pore size and pore density, the optical analysis was repeated using images obtained from the scanning electron microscope. FIG. 5 is an image of two coupons produced from a CoCr array on Ti alloy substrates. This array was chosen because it best satisfied the requirements of this exercise. The parameters were: laser power of 82 W continuous wave (cw); 25% beam overlap; scanning speed varied from 100 mms$^{-1}$ to 260 mms$^{-1}$ in 20 mm-$^1$ increments; the images of the coupons shown here, taken from this array, were produced with scanning speeds of 180 mms$^{-1}$ to 200 mms$^{-1}$. The surface is comprised of fused pathways that develop a network of interconnected pores. This structure continues throughout the layer until the interface is reached. The interface is characterized by a patchwork of fusion bonds. These bond sites are responsible for securing the interconnected surface structure to the baseplate. The macroscopic structure is covered with unmelted powder particles that appear to be loosely attached. In addition, there are larger resolidified globules that may have limited bonding to the surface.

FIGS. 6 and 7 are the scanning electron microscope images produced from the Nb and Ta coupons on Ti alloy substrates. Specifically, FIGS. 6A to 6E are scanning election microscope images of the surface structure of Nb on Ti alloy substrates, produced with a laser power of 82 W cw, −40% beam overlap. The scanning speeds used were: 160 mms$^{-1}$ for FIG. 6A, 190 mms$^{-1}$ for FIG. 6A, 200 mms$^{-1}$ for FIG. 6C, 210 mms$^{-1}$ for FIG. 6D and 240 mms$^{-1}$ for FIG. 6E, respectively.

Figure 7A:
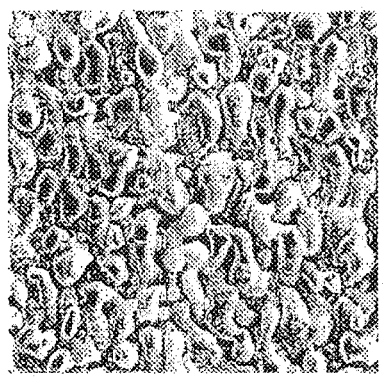
Figure 7B:
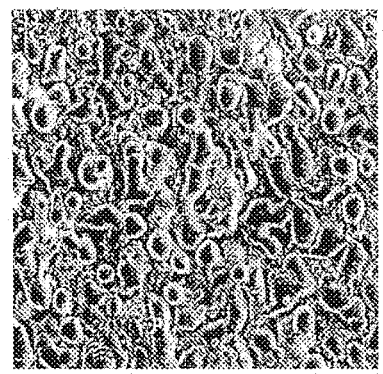
Figure 7C:
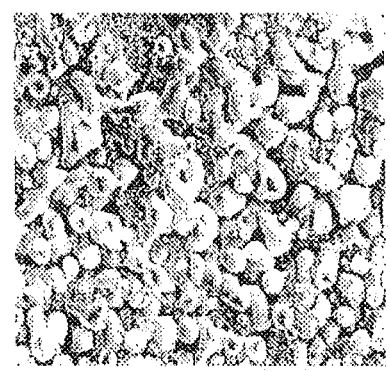

FIGS. 7A to 7C are scanning election microscope images of the surface structure of Ta on Ti alloy substrates produced using the same parameters used in the Nb or Ti alloy substrates except: FIG. 7A was produced with a scanning speed of 160 mms$^{-1}$; FIG. 7B's speed was 200 mms$^{-1}$ and FIG. 7C's speed was 240 mms$^{-1}$, respectively. An increased beam overlap was used here as Nb and Ta have high melting points, which require a greater energy density. The surfaces once again exhibit significant levels of unmelted powder particles and loosely attached resolidified beads that vary in size from a few microns to several hundred microns. All samples were loosely brushed after completion and cleaned in an ultrasonic aqueous bath. It is possible that further cleaning measures may reduce the fraction of loose particles.

Figure 8A:
Figure 8B:
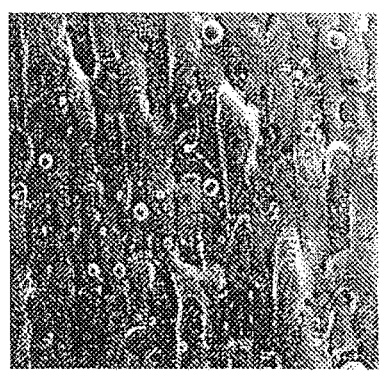
Figure 8C:
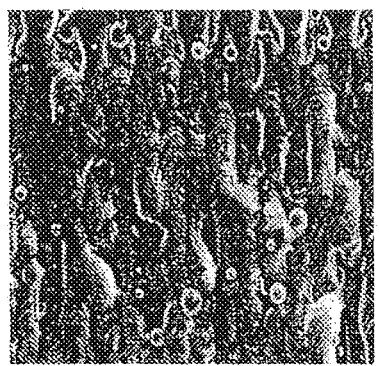
Figure 8D:
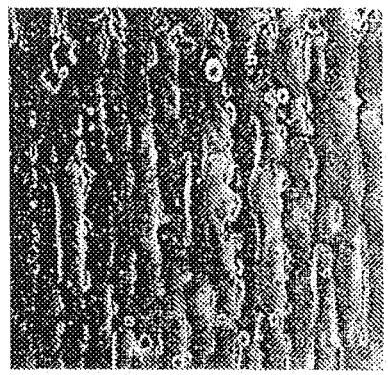
Figure 8E:
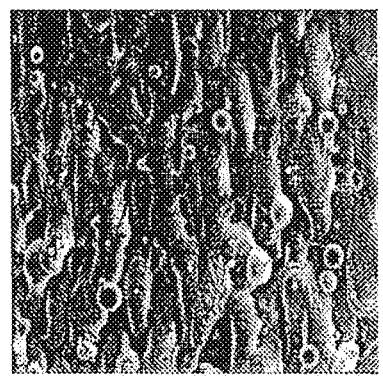
Figure 9A:
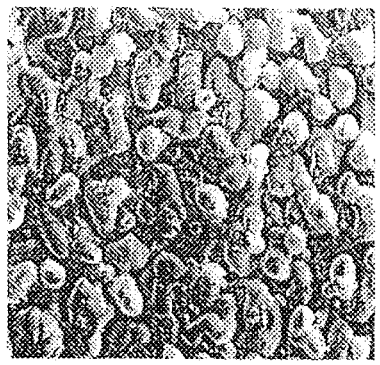
Figure 9B:
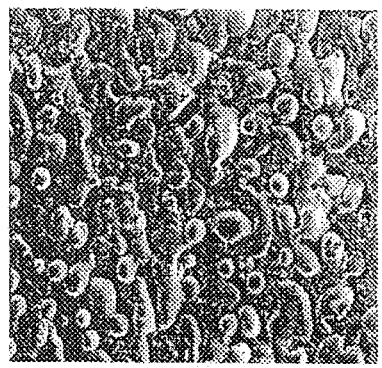
Figure 9C:
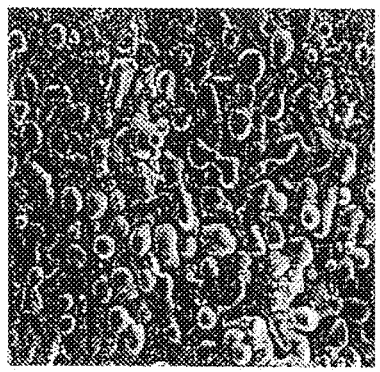
Figure 9D:
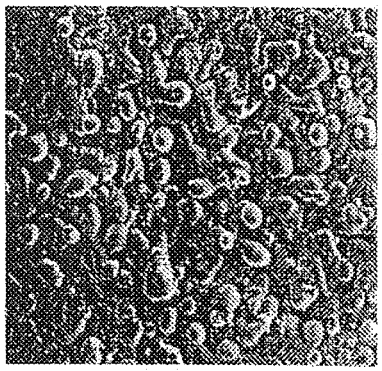
Figure 9E:
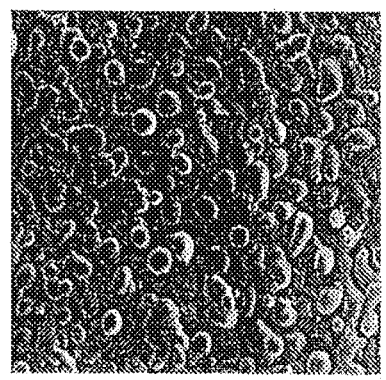
Figure 10A:
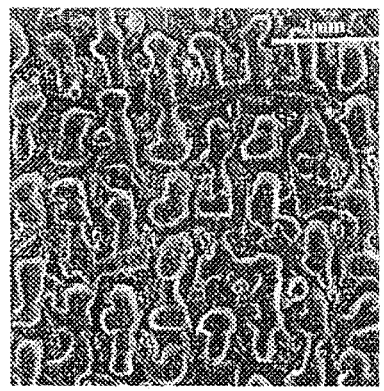
Figure 10B:
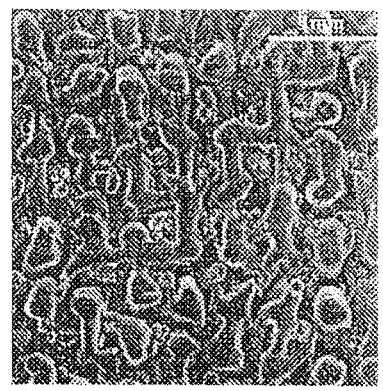
Figure 10C:
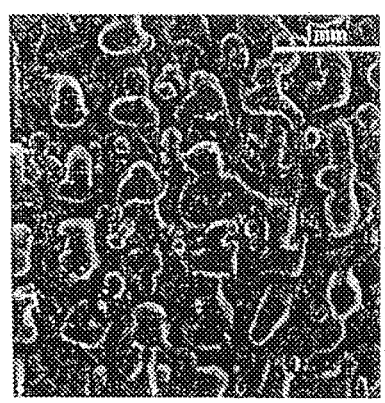
Figure 10D:
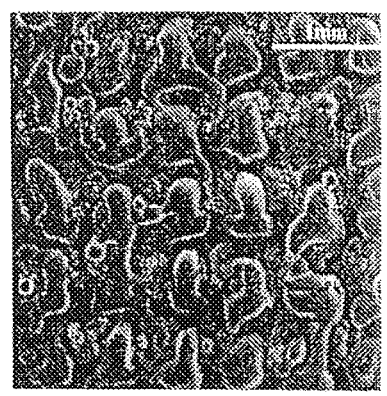
Figure 10E:
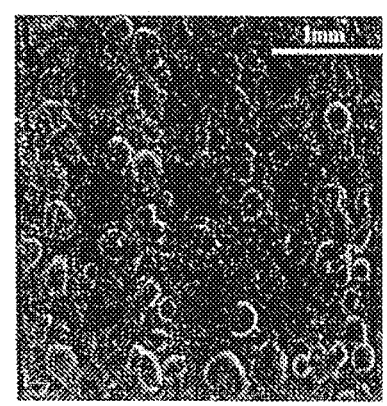
Figure 10F:
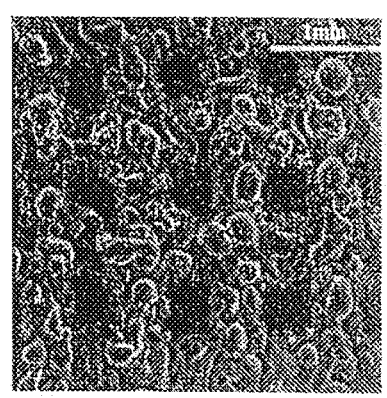

FIGS. 8A to 8E are scanning electron microscope images taken from the Ti coupons on the CoCr alloy substrates. The laser processing parameters used were the same as those for the Nb and Ta powders, with once again only the speed varying. The scanning speed was varied from 160 mms$^{-1}$ (FIG. 8A, 170 mms$^{-1}$ (FIG. 8B), 200 mms$^{-1}$ (FIG. 8C); 230 mms$^{-1}$ (FIG. 8D) to 240 mms$^{-1}$ (FIG. 8E). The Ti coupon on CoCr samples, (FIGS. 8A to 8C) indicate very high density levels compared to the other examples. The line-scans can be clearly seen, with good fusion between individual tracks, almost creating a complete surface layer. The surface begins to break up as the scanning speed is increased.

FIGS. 9A to 9E are scanning electron microscope images of surface structures of Ti on Ti alloy substrates produced with the same parameters used in FIGS. 8A to 8E, respectively. It is unclear why Ti should wet so well on CoCr substrates. In comparison, Ti on Ti exhibits similar characteristic patterns as with Nb, Ta, and CoCr, specifically, an intricate network of interconnected pores.

Figure 11:
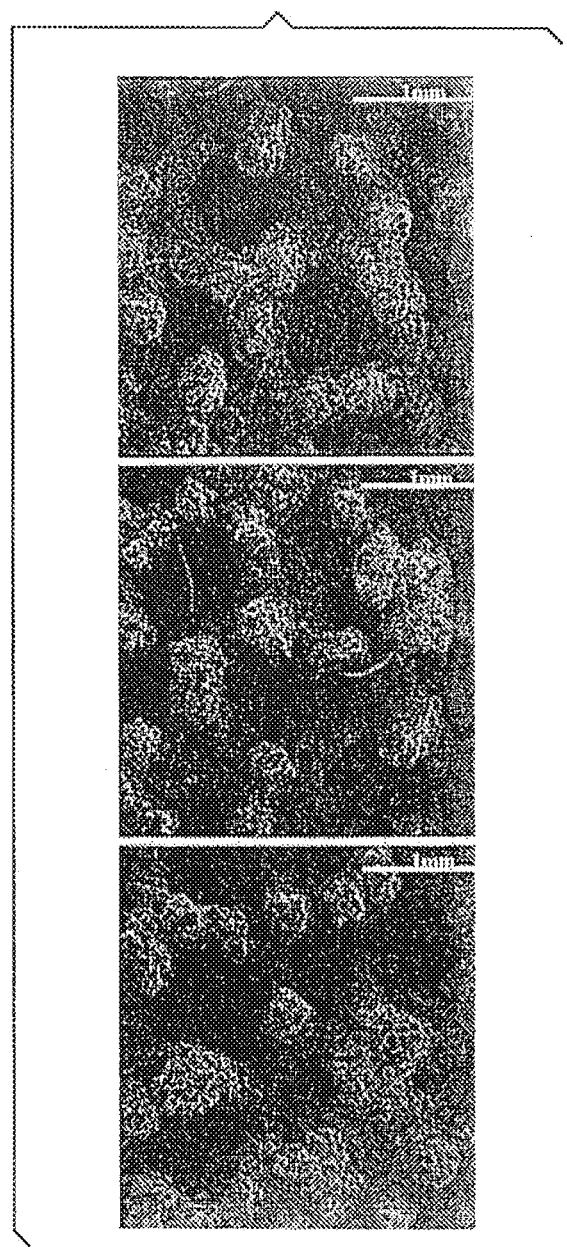
FIG. 11 is a scanning electron microscope micrograph taken from a porous Ti sintered structure.

Following the completion of the multi-layer coupons, a series of 20 mm×20 mm structures were produced from Ti that utilized an X and Y-direction "waffle" scanning format using the optimum Ti operating parameters with the two scans being orthogonal to one another. The intention behind these experiments was to demonstrate the ability of the Direct Laser Remelting process to produce parts with a controlled porosity, e.g. internal channels of dimensions equal to the required pore size, e.g. 80 μm to 400 μm. To do this, a relatively large beam overlap of between −400% and −600% was used. Scanning electron microscope images of the surfaces of these structures are shown in FIGS. 10A to 10F. The scanning speed, 160 mms$^{-1}$ and the laser power 72 W cw were kept constant while the beam overlaps; −400% in FIGS. 10A and 10B; −500% in FIGS. 10C and 10D and −600% in FIGS. 10E and 10F, were varied accordingly. Scanning electron microscope micrographs, taken from a porous Ti sintered structure provided by Stryker-Howmedica are shown for reference in FIG. 11.

Figure 12:
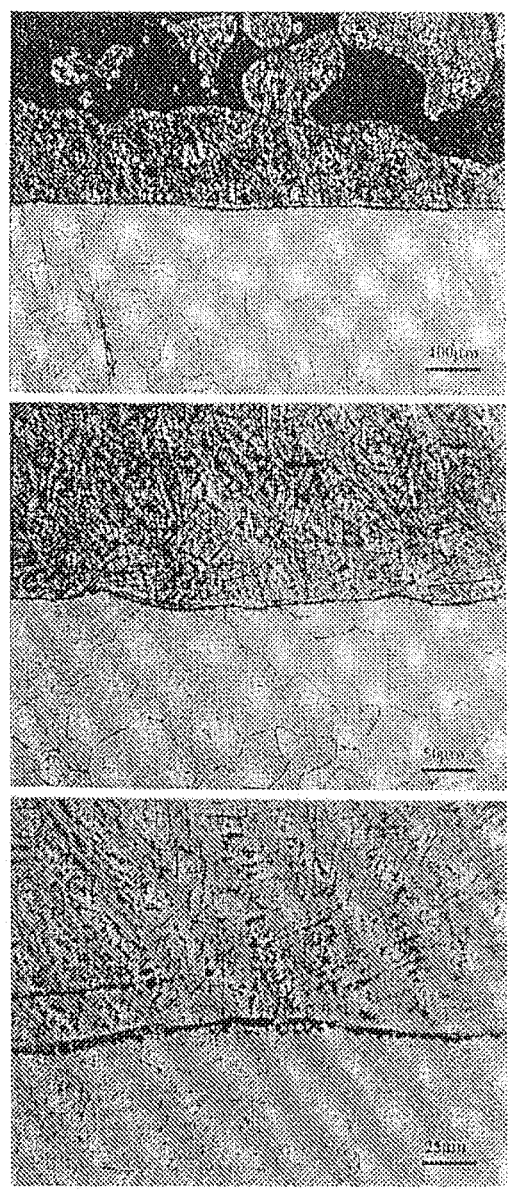
FIG. 12 is an optical image of a section through a sample showing the microstructure.

To illustrate more clearly the interaction between the substrate/structure metallurgical interaction, the Ti on Ti substrate was sectioned, hot mounted and polished using a process of 1200 and 2500 grade SiC, 6 μm diamond paste and 70/30 mixture of OPS and 30% $H_2O_2$. The polished sample was then etched with 100 ml $H_2O$, 5 ml NH.FHF and 2 $cm^3$ HCl for 30 seconds to bring out the microstructure. Optical images of this sample in section are shown in FIG. 12.

Figure 13:
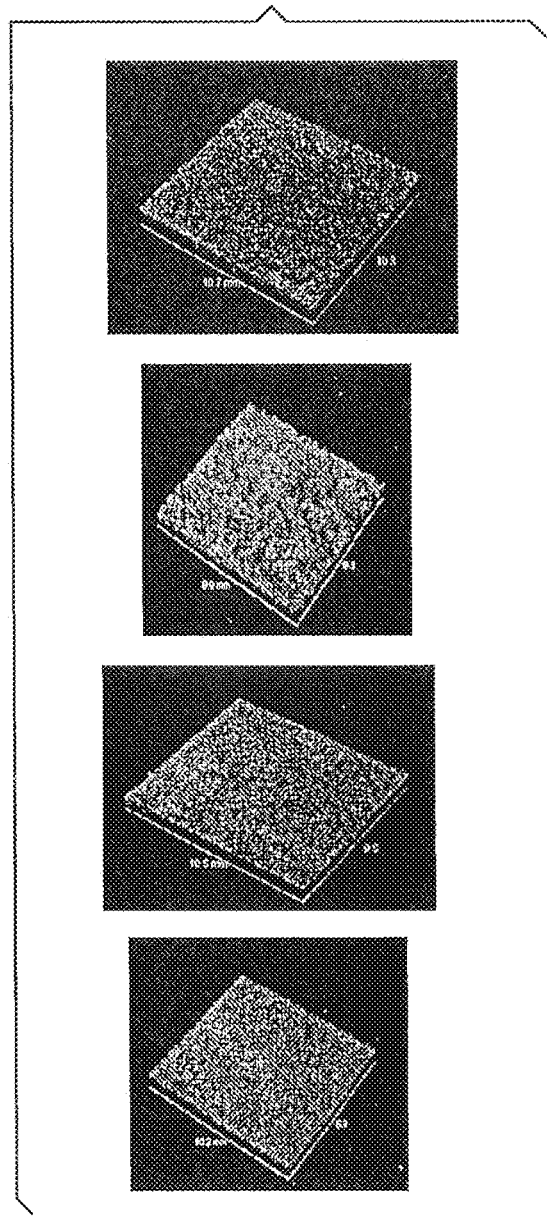
FIG. 13 is an image detailing surface structures.

FIG. 13 is an image taken from a non-contact surface profilimentry to show the surface structures obtained when using Ti, CoCr, Ta and Nb on Ti substrates. Values for Ra, Rq and Rb roughness are also shown.

From the optical and scanning election microscope analysis conducted, it is apparent that the Direct Laser Remelting process is capable of satisfying the requirements for pore characteristics, concerning maximum and minimum pore size, interconnectivity and pore density. From the initial visual analysis of the CoCr coupons, it was apparent from these and other examples, that subtle variations in pore structure and coverage could be controlled by scanning velocity and line spacing.

The key laser parameters varied for forming the three-dimensional metallic porous structures are: (a) Laser scanning speed (v.) in ($mms^{-1}$), which controls the rate at which the laser traverses the powder bed; (b) Laser power, P(W), which in conjunction with the laser spot size controls the intensity of the laser beam. The spot size was kept constant throughout the experiment; (c) Frequency, (Hz) or pulse repetition rate. This variable controls the number of laser pulses per second. A lower frequency delivers a higher peak power and vice versa.

The line width can be related to the laser scanning speed and the laser power to provide a measure of specific density, known as the "Andrew Number", where:

$$An = \frac{P}{b \times v} \ (J/mm^{-2})$$

Where P denotes the power of the laser, v is the laser scanning speed and b denotes beam width of the laser. The Andrew number is the basis for the calculation of the present invention. The Andrew number may also be calculated by substituting the line separation (d) for beam width (b). The two methods of calculating the Andrew number will result in different values being obtained. When using line separation (d) as a factor only on track of fused powder is considered, whereas when using the beam width (b) as a factor, two tracks of fused powder are considered as well as the relative influence of one track to the next. For this reason we have chosen to concern ourselves with the Andrew number using scan spacing as a calculating factor. It can thus be appreciated, that the closer these tracks are together the greater the influence they have on one another.

Additionally, the laser power may be varied between 5 W and 1000 W. Utilizing lower power may be necessary for small and intricate parts but would be economically inefficient for such coatings and structures described herein. It should be noted that the upper limit of laser power is restricted because of the availability of current laser technology. However, if a laser was produced having a power in excess of 1000 W, the scanning speed of the laser could be increased in order that an acceptable Andrew number is achieved. A spot size having a range between 5 um(fix) to 500 um(fix) is also possible. For the spot size to increase while still maintaining an acceptable Andrew number, either the laser power must be increased or the scanning speed decreased.

The above formula gives an indication of how the physical parameters can vary the quantity of energy absorbed by the powder bed. That is, if the melted powder has limited cohesion, e.g. insufficient melting, the parameters can be varied to concentrate the energy supply to the powder. High Andrew numbers result in reduced pore coverage and an increase in pore size due to the effects of increased melt volume and flow. Low Andrew numbers result in low melt volume, high pore density and small pores. Current satisfactory Andrew numbers are approximately 0.3 $J/mm^{-2}$ to 8 $J/mm^{-2}$ and are applicable to many alternative laser sources. It is possible to use a higher powered laser with increased scanning speed and obtain an Andrew number within the working range stated above.

Figure 4A:
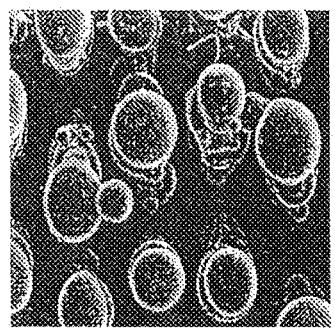
FIGS. 4A to 10F are scanning electron microscope images of the surface structure of various samples made by the method according to the invention.
Figure 4B:
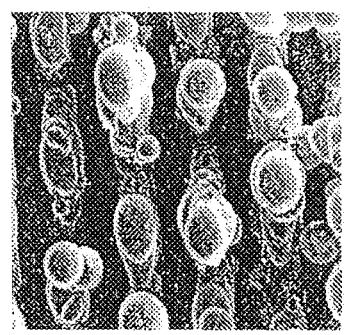
Figure 4C:
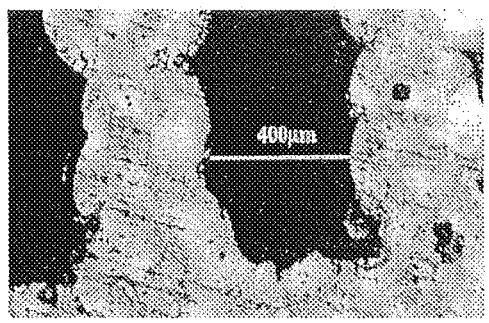

Line spacing or beam overlap can also be varied to allow for a gap between successive scan lines. It is, therefore, possible to heat selected areas. This gap would allow for a smaller or larger pore size to result. The best illustration of this is shown in FIGS. 4A to 4C where a −500% beam overlap has been applied. FIGS. 4A to 4C are scanning election microscope images of the surface structure of CoCr on stainless steel produced with a laser power of 82 W cw. FIG. 4A was produced with a laser scanning speed of 105 $mms^{-1}$ and FIG. 4B was produced with a laser scanning speed of 135 $mms^{-1}$. FIG. 4C is an image of the same structure in FIG. 4B, in section. There is a significant self-ordering within the overall structure. Larger columnar structures are selectively built leaving large regions of unmelted powder. It is worth noting that these pillars are around 300 μm wide, over 1.6 mm tall and fuse well with the substrate, as seen in FIG. 4C. Further analysis shows that the use of a hatched scanning format allows porosity to be more sufficiently controlled to allow the pore size to be directly controlled by the beam overlap.

The use of an optical inspection method to determine this approximate porosity is appropriate given the sample size. This method, although not accurate due to the filter selection process, can, if used carefully, provide an indication of porosity. An average porosity level of around 25% was predicted. This porosity level falls within the range of the desired porosity for bone in-growth structures. The mechanical characteristics of the porous structures are determined by the extent of porosity and the interconnecting webs. A balance of these variables is necessary to achieve the mechanical properties required by the intended application.

Increased fusion may, if required, be obtained by heating the substrate, powder or both prior to scanning. Such heating sources are commonly included in standard selective laser sintering/melting machines to permit this operation.

Following trials on the titanium build on the cobalt chromium substrate, it was determined that the interface strength was insufficient to serve the intended application. Trials were made by providing a bond coat of either tantalum or niobium on the cobalt chromium substrate prior to the deposition of the titanium layers to for the porous build. The typical protocol involved:
  (i) Initial cleaning scan with a scan speed between 60 to 300 mm/sec, laser power 82 watts, frequency of 30 KHz, and a 50% beam overlap.
  (ii) Niobium or tantalum deposition with three layers of 50 μm using a laser power of 82 watts, frequency 30 to 40 KHz, with a laser speed of between 160 to 300 mm/sec. The beam overlap was low at 50% to give good coverage.

(iii) A build of porous titanium was constructed using a laser power of 82 watts, frequency between 0 (cw) and 40 KHz, scanning speed of between 160 and 240 mm/sec, and beam overlap of −700%.

The strengths of the constructs are indicated in Table 3 with a comparison of the values obtained without the base coat.

TABLE 3

| SPECIMEN | MAXIMUM LOAD (kN) | TENSILE STRENGTH (MPa) | FAILURE MODE |
|---|---|---|---|
| Ti on CoCr | 2.5 | 5 | Interface |
| Ti on CoCr | 3.1 | 6.2 | Interface |
| 1 (Nb on Co—Cr) | 13.0 | 26.18 | 65% adhesive, 35% bond interface |
| 4 (Ti on Nb on Co—Cr) | 7.76 | 15.62 | Mostly bond coat interface |
| 5 (Ti on Nb on Co—Cr) | 9.24 | 18.53 | 20% adhesive, 40% bond coat, 40% porous Ti |
| 6 (Ti on Ta on Co—Cr) | 11.58 | 23.33 | Mostly adhesive with discrete webbing weakness |
| 8 (Ta on Co—Cr) | 13.93 | 27.92 | 60% adhesive, 40% bond interface |
| 9 (Ti on Ta on Co—Cr) | 6.76 | 13.62 | 100% bond interface |

Figure 26:
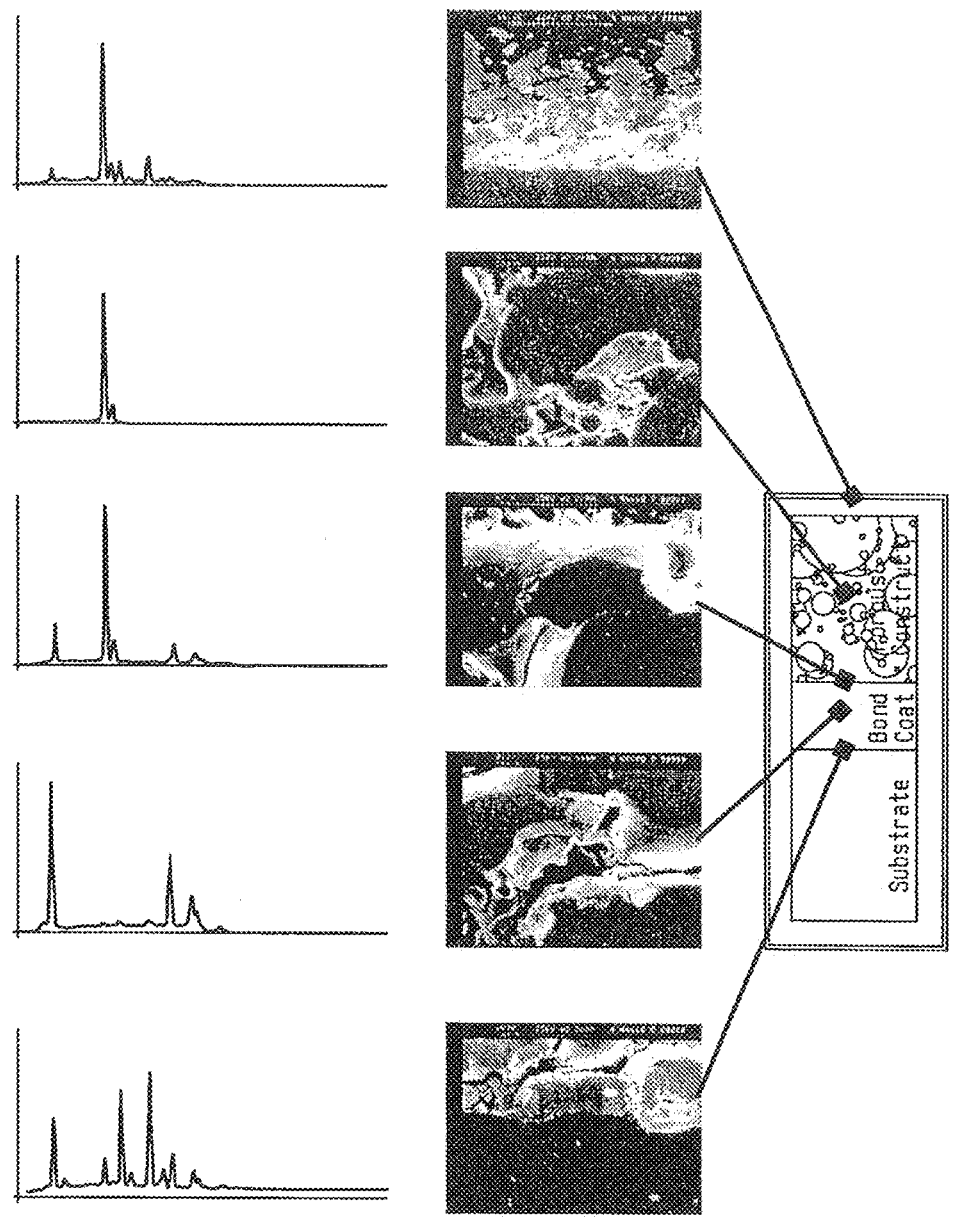
FIG. 26 indicates the metallography and spectra of a typical bond coat structure.

FIG. 26 shows the metallography of the structures with energy dispersive spectroscopy (EDS) revealing the relative metal positions within the build.

A typical waffle build of titanium on a titanium substrate was constructed as a way of regulating the porous structure. Scanning sequences of 0° 0° 0°, 90° 90° 90°, 45° 45° 45°, 135°, 135°, 135°, of layer thickness 0.1 mm were developed to form a waffle. Three layers of each were necessary to obtain sufficient web thickness in the "z" direction to give a structure of adequate strength. Typical parameters employed were: Laser power was 82 watts, operating frequency between 0 (cw) and 40 KHz, scan speed of between 160 and 240 mm/sec with a beam overlap of −700%. FIG. 27 gives an indication of the effect of line spacing and pore size. FIG. 28A shows typical examples of the waffle structure. The magnification level changes from 10, 20, 30, 70 and 150 times normal viewing as one moves respectively from Fig. B to F. FIG. 28A more specifically shows Ti powder on a Ti substrate with a controlled porosity by varying line spacing, i.e., beam overlap.

Figure 29:
FIG. 29 is a trabecular bone-type structure constructed from a micro CT scan.

Trabecular structures of titanium on a titanium substrate were constructed as a way of randomising the porous structures. An STL (sterolithography) file representing trabecular structure was produced from a micro CT scan of trabecular bone. This file was sliced and the slice data sent digitally to the scanning control. This allowed the layer-by-layer building of a metallic facsimile to be realised. FIG. 29 shows a cross-sectional view of such a construct.

Figure 30:
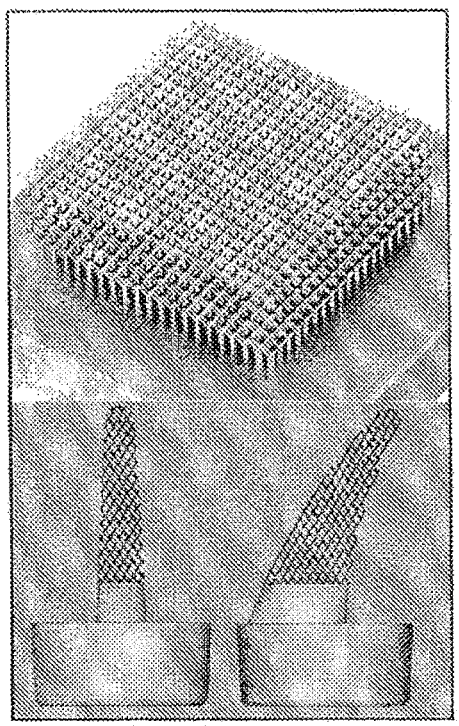
FIG. 30 shows typical freestanding structures.

A method for making lattice-type constructs was referred to in the relevant art. A typical example of this type of structure is shown in FIG. 30. The scanning strategy employed to form such a construct was mentioned and such a strategy could be produced within the range of Andrew numbers outlined. Table 4 shows an indication of scanning strategies and their relationships to the Andrew number.

TABLE 4

| LAYER | SCAN STRATEGY | PARAMETER SET | LAYER THICKNESS | RELATIVE BUILD PLATFORM POSITION | ADDITIONAL |
|---|---|---|---|---|---|
| Ti on Ta on CoCr Experimental Procedure. | | | | | |
| Initial Tantalum Coating | | | | | |
| Zero Distance Between Roller & Build Platform | | | | 0 | |
| 0 | 1$^{st}$ layer thickness set using feeler gauges but powder not laid in preparation for cleaning scan with no powder. | | 50 μm | −50 μm | |
| 1 | 50% Beam Overlap | P = 82 W Qs = 30 kHz v = 60 mm/s $A_n$ = 27.333 J/mm$^2$ | | | Initial Cleaning Scan (no powder) |
| | Circular profile. 5 concentric circles, 0.1 mm offset to negate effects of 'First Pulse' | P = 82 W Qs = 40 kHz V = 160 mm/s $A_n$ = 5.125 J/mm$^2$ | | | Powder laid as usual |
| | 50% Beam Overlap | P = 82 W Qs = 30 kHz v = 300 mm/s $A_n$ = 5.467 J/mm$^2$ | | | Scanned on same powder layer as previous profile scan. |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| 2 | Circular profile. 5 concentric circles, 0.1 mm offset to negate effects of 'First Pulse' | $P = 82$ W<br>$Qs = 40$ kHz<br>$V = 160$ mm/s<br>$A_n = 5.125$ J/mm$^2$ | 50 μm | −100 μm | Powder laid as usual |
|  | 50% Beam Overlap | $P = 82$ W<br>$Qs = 30$ kHz<br>$v = 300$ mm/s<br>$A_n = 5.467$ J/mm$^2$ |  |  | Scanned on same powder layer as previous profile scan. |
| 3 | Circular profile. 5 concentric circles, 0.1 mm offset to negate effects of 'First Pulse' | $P = 82$ W<br>$Qs = 40$ kHz<br>$V = 160$ mm/s<br>$A_n = 5.125$ J/mm$^2$ | 50 μm | −150 μm | Powder laid as usual |
|  | 50% Beam Overlap | $P = 82$ W<br>$Qs = 30$ kHz<br>$v = 300$ mm/s<br>$A_n = 5.467$ J/mm$^2$ |  |  | Scanned on same powder layer as previous profile scan. |
| | | Final Titanium Coating | | | |
| 0 | 1$^{st}$ layer thickness set using feeler gauges but powder not laid in preparation for cleaning scan with no powder. |  |  | −150 μm |  |
| 1 | 50% Beam Overlap | $P = 82$ W<br>$Qs = 30$ kHz<br>$v = 60$ mm/s<br>$A_n = 27.3$ J/mm$^2$ | 50 μm | −200 μm | Cleaning Scan (No powder. |
|  | Circular profile. 5 concentric circles, 0.1 mm offset to negate effects of 'First Pulse' | $P = 82$ W<br>$Qs = 40$ kHz<br>$V = 160$ mm/s<br>$A_n = 5.125$ J/mm$^2$ |  |  | Powder spread but build platform not lowered. |
|  | 50% Beam Overlap | $P = 82$ W<br>$Qs = 30$ kHz<br>$v = 300$ mm/s<br>$A_n = 5.467$ J/mm$^2$ |  |  | Scanned on same powder layer as previous profile scan. |
| 2 | Circular profile. 5 concentric circles, 0.1 mm offset to negate effects of 'First Pulse' | $P = 82$ W<br>$Qs = 40$ kHz<br>$V = 160$ mm/s<br>$A_n = 5.125$ J/mm$^2$ | 100 μm | −300 μm | Powder laid as usual |
|  | 25% Beam Overlap | $P = 82$ W<br>$Qs = 30$ kHz<br>$v = 300$ mm/s<br>$A_n = 3.644$ J/mm$^2$ |  |  | Scanned on same powder layer as previous profile scan. |
| 3 | Circular profile. 5 concentric circles, 0.1 mm offset to negate effects of 'First Pulse' | $P = 82$ W<br>$Qs = 40$ kHz<br>$V = 160$ mm/s<br>$A_n = 5.125$ J/mm$^2$ | 100 μm | −400 μm | Powder laid as usual |
|  | 0% Beam Overlap | $P = 82$ W<br>$Qs = 30$ kHz<br>$v = 300$ mm/s<br>$A_n = 2.733$ J/mm$^2$ |  |  | Scanned on same powder layer as previous profile scan. |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| 4 | Waffle 0 and 90° 700 μm linespacing (−600% Beam overlap) | P = 82 W<br>Qs = 0 Hz (cw)<br>v = 240 mm/s<br>$A_n$ = 0.488 J/mm² | 75 μm | −475 μm | Powder laid as usual |
| 5 | Waffle 0 and 90° 700 μm linespacing (−600% Beam overlap) | P = 82 W<br>Qs = 0 Hz (cw)<br>v = 240 mm/s<br>$A_n$ = 0.488 J/mm² | 75 μm | −550 μm | Powder laid as usual |
| 6 | Waffle 0 and 90° 700 μm linespacing (−600% Beam overlap) | P = 82 W<br>Qs = 0 Hz (cw)<br>v = 240 mm/s<br>$A_n$ = 0.488 J/mm² | 75 μm | −625 μm | Powder laid as usual |
| 7 | Waffle 45 and 135° 700 μm linespacing (−600% Beam overlap) | P = 82 W<br>Qs = 0 Hz (cw)<br>v = 240 mm/s<br>$A_n$ = 0.488 J/mm² | 75 μm | −700 μm | Powder laid as usual |
| 8 | Waffle 45 and 135° 700 μm linespacing (−600% Beam overlap) | P = 82 W<br>Qs = 0 Hz (cw)<br>v = 240 mm/s<br>$A_n$ = 0.488 J/mm² | 75 μm | −775 μm | Powder laid as usual |
| 9 | Waffle 45 and 135° 700 μm linespacing (−600% Beam overlap) | P = 82 W<br>Qs = 0 Hz (cw)<br>v = 240 mm/s<br>$A_n$ = 0.488 J/mm² | 75 μm | −850 μm | Powder laid as usual |
| Ti on Ti Experimental Procedure. | | | | | |
| Initial Titanium Coating | | | | | |
| Zero Distance Between Roller & Build Platform | | | | 0 | |
| 0 | 1$^{st}$ layer thickness set using feeler gauges but powder not laid in preparation for cleaning scan with no powder. | | 50 μm | −50 μm | |
| 1 | 50% Beam Overlap | P = 82 W<br>Qs = 30 kHz<br>v = 60 mm/s<br>$A_n$ = 27.333 J/mm² | | | Initial Cleaning Scan (no powder) |
| | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm² | | | Powder laid as usual |
| | 50% Beam Overlap | P = 82 W<br>Qs = 30 kHz<br>v = 300 mm/s<br>$A_n$ = 5.467 J/mm² | | | Scanned on same powder layer as previous profile scan. |
| 2 | Circular profile. 5 concentric circles, 0.1 mm offset to negate | P = 82 W<br>Qs = 40 kHz<br>V = 160 mm/s<br>$A_n$ = 5.125 J/mm² | 50 μm | −100 μm | Powder laid as usual |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| | effects of 'First Pulse' | | | | |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |
| 3 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 50 μm | −150 μm | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |
| | Final Titanium Coating | | | | |
| 1 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 100 μm | −250 μm | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan |
| 2 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 100 μm | −350 μm | Powder laid as usual |
| | 25% Beam Overlap | P = 82 W<br>Qs = 30 kHz<br>v = 300 mm/s<br>$A_n$ = 3.644 J/mm$^2$ | | | Scanned on same powder layer as previous profile scan. |
| 3 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 100 μm | −450 μm | Powder laid as usual |
| | 0% Beam Overlap | P = 82 W<br>Qs = 30 kHz<br>v = 300 mm/s<br>$A_n$ = 2.733 J/mm$^2$ | | | Scanned on same powder layer as previous profile scan. |
| 4 | Waffle 0 and 90° 700 μm linespacing (−600% Beam overlap) | P = 82 W<br>Qs = 0 Hz (cw)<br>v = 240 mm/s<br>$A_n$ = 0.488 J/mm$^2$ | 75 μm | −525 μm | Powder laid as usual |
| 5 | Waffle 0 and 90° 700 μm linespacing (−600% Beam overlap) | P = 82 W<br>Qs = 0 Hz (cw)<br>v = 240 mm/s<br>$A_n$ = 0.488 J/mm$^2$ | 75 μm | −600 μm | Powder laid as usual |
| 6 | Waffle 0 and 90° 700 μm linespacing (600% Beam overlap) | P = 82 W<br>Qs = 0 Hz (cw)<br>v = 240 mm/s<br>$A_n$ = 0.488 J/mm$^2$ | 75 μm | −675 μm | Powder laid as usual |
| 7 | Waffle 45 and 135° 700 μm linespacing (−600% Beam overlap) | P = 82 W<br>Qs = 0 Hz (cw)<br>v = 240 mm/s<br>$A_n$ = 0.488 J/mm$^2$ | 75 μm | −750 μm | Powder laid as usual |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| 8 | Waffle 45 and 135° 700 μm linespacing (−600% Beam overlap) | P = 82 W $Q_s$ = 0 Hz (cw) v = 240 mm/s $A_n$ = 0.488 J/mm² | 75 μm | −825 μm | Powder laid as usual |
| 9 | Waffle 45 and 135° 700 μm linespacing (−600% Beam overlap) | P = 82 W $Q_s$ = 0 Hz (cw) v = 240 mm/s $A_n$ = 0.488 J/mm² | 75 μm | −900 μm | Powder laid as usual |

Figure 31:
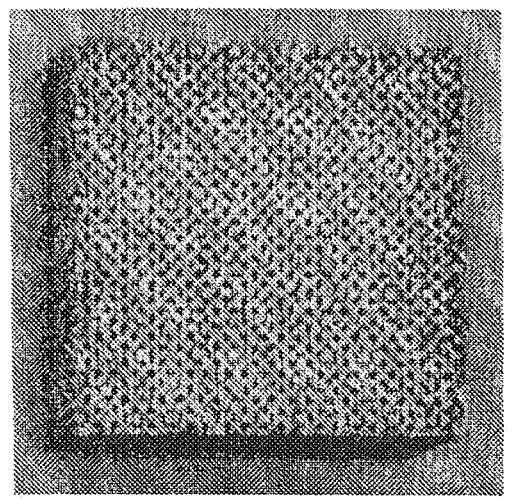
FIG. 31 shows a freestanding structure built using the preferred scanning strategy.

The second and preferred approach uses a continuous scanning strategy whereby the pores are developed by the planar deposition of laser melted powder tracks superimposed over each other. This superimposition combined with the melt flow produces random and pseudorandom porous structures. The properties of the final structure, randomness, interconnectivity, mechanical strength and thermal response are controlled by the process parameters employed. One set of scanning parameters used was: Scanning sequences of 0° 0° 0°, 90° 90° 90°, 45° 45° 45°, 135°, 135°, 135°, of layer thickness 0.1 mm were developed to form a waffle. Three layers of each were necessary to obtain sufficient web thickness in the "z" direction. The array of sequences was repeated many times to give a construct of the desired height. Laser power was 82 watts, operating frequency between 0 (cw) and 40 KHz, scan speed of between 160 and 240 mm/sec with a beam overlap of −700%. FIG. 31 shows such a construct.

The use of an optical inspection method to determine this approximate porosity is appropriate given the sample size. This method, although not accurate due to the filter selection process, can, if used carefully, provide an indication of porosity. An average porosity level of around 25% was predicted. This porosity level falls within the range of the desired porosity for bone in-growth structures.

In consideration of the potential application, it is important to minimize loose surface contamination and demonstrate the ability to fully clean the surface. Laser cleaning or acid etching technique may be effective. Additionally, a rigorous cleaning protocol to remove all loose powder may entail blowing the porous structure with clean dry compressed gas, followed by a period of ultrasonic agitation in a treatment fluid. Once dried, a laser scan may be used to seal any remaining loose particles.

On examination, all candidate materials and substrates were selectively fused to produce a complex interconnected pore structure. There were small differences in certain process parameters such as speed and beam overlap percentage. From FIG. 12 it can also be seen how the Ti build has successfully fused with the Ti alloy substrate using a laser power of 82 W cw, beam overlap of −40% and a laser scanning speed of 180 mms$^{-1}$. With the ability to produce structures with a controlled porosity, this demonstrates how the Direct Laser Remelting process can be used as a surface modification technology. Certain metal combinations interacted unfavourably and resulted in formation of intermetallics, which are inherently brittle structures. To overcome this problem it may be necessary to use a bond coat with the substrate. It is then possible to build directly on to the substrate with a porous build. A typical example of the use of a bond coat is provided by the combination of titanium on to a cobalt chromium substrate. Tantalum also was an effective bond coat in this example. Note that the bond coat may be applied by laser technology, but other methods are also possible such as gas plasma deposition.

Figure 14A:
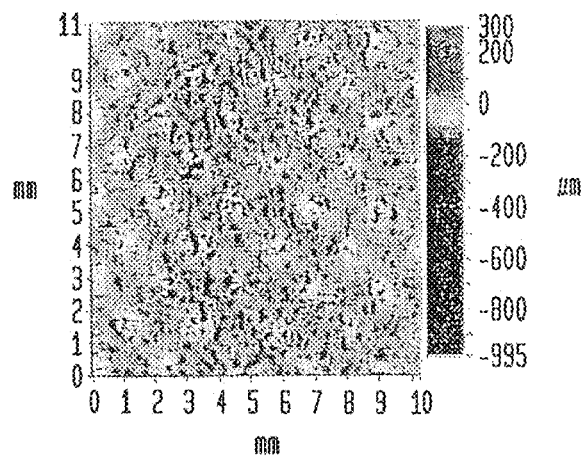
FIGS. 14A-15B are non-contact surface profilimetry images detailing plan views of the samples.
Figure 14B:
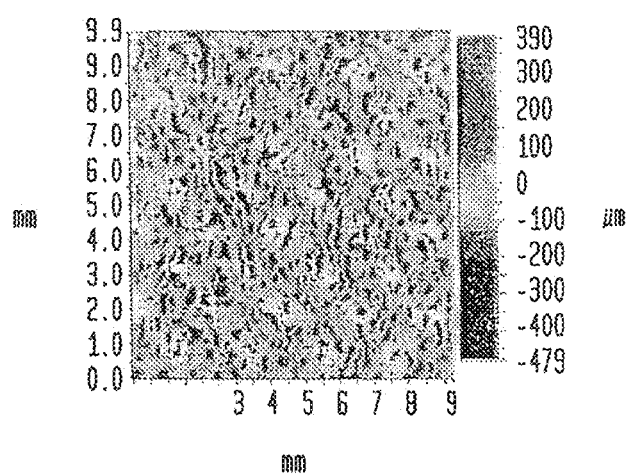
Figure 15A:
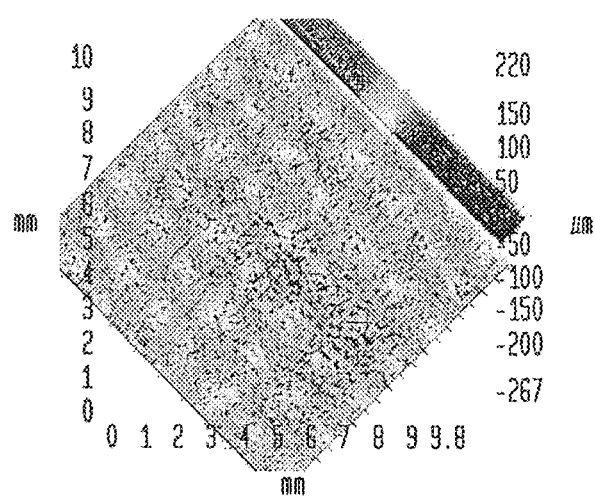
Figure 15B:
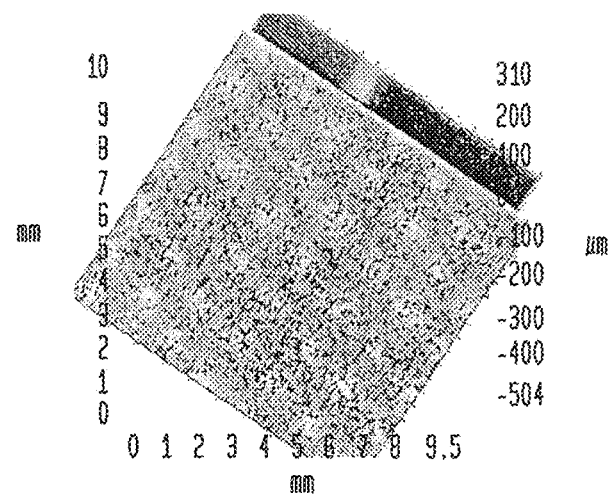

The non-contact surface profilimeotry (OSP) images shown in FIGS. 13A to 13D show the surface profile. In addition, the Surface Data shown in FIGS. 14A and 14B and 15A and 15B show a coded profile of the plan views of the samples. FIG. 14A shows Ti on Ti (OSP Surface Data) where v=200 mms-$^1$, FIG. 14B shows CoCr on Ti (OSP Surface Data) where v=200 mms-$^1$, and FIG. 15A shows Nb on Ti (OSP Surface Data) where v=200 mms-$^1$ and FIG. 15B shows Ta on Ti (OSP Surface Data) where v=200 mms-$^1$.

FIGS. 16A to 25 are scanning electron microscope (SEM) micrographs of a series of single layer Ti on CoCr and Ti on Ti images that were produced prior to the multi-layer builds shown in FIGS. 8 and 9 respectively and as follows.

Figure 16A:
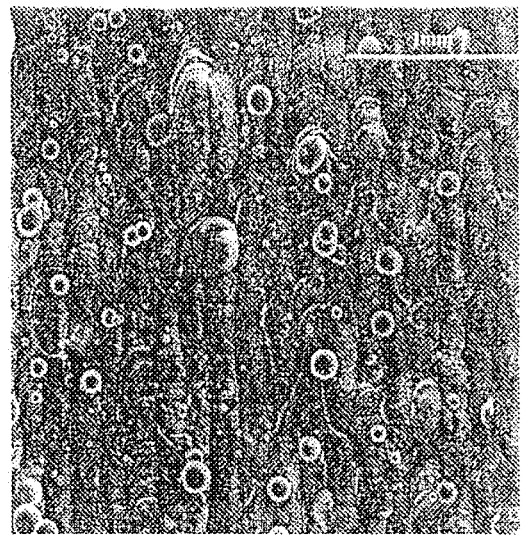
FIGS. 16A-25 are scanning electron microscope micrographs produced prior to multi-layer builds shown in FIGS. 7A-8E.
Figure 16B:
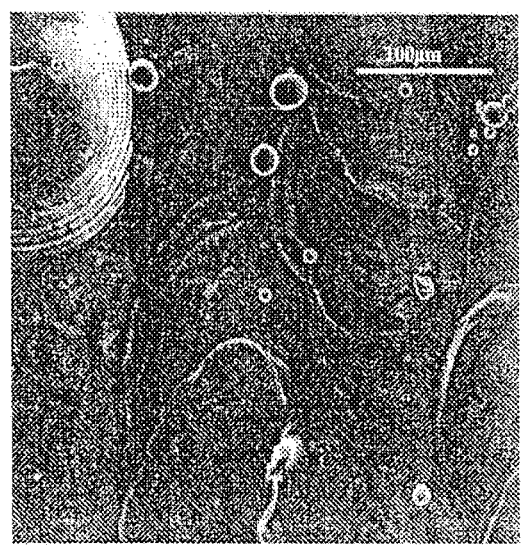
Figure 17A:
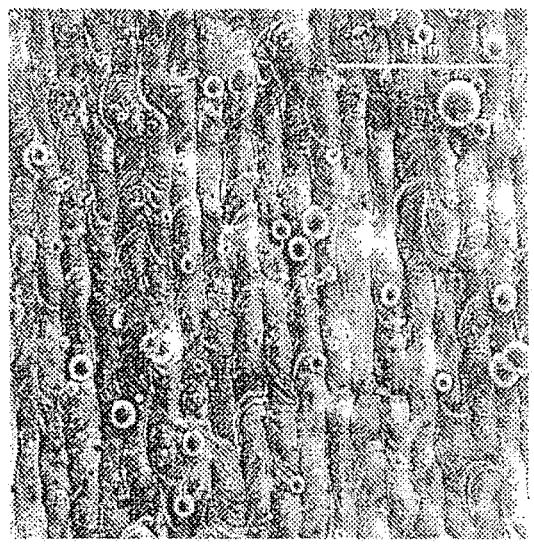
Figure 17B:
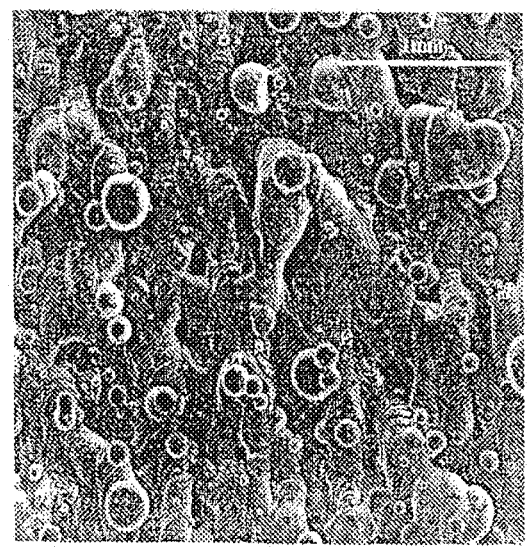
Figure 18A:
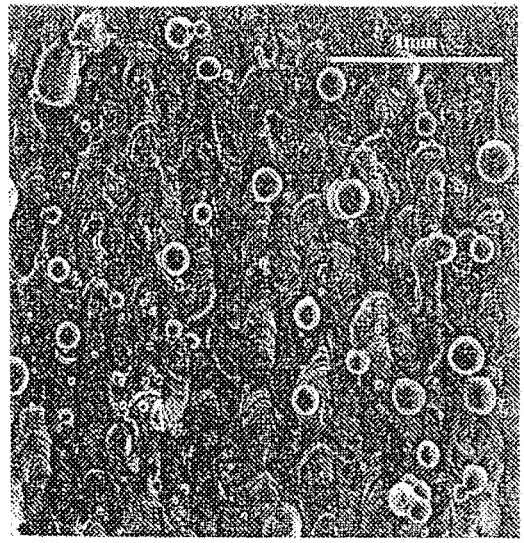
Figure 18B:
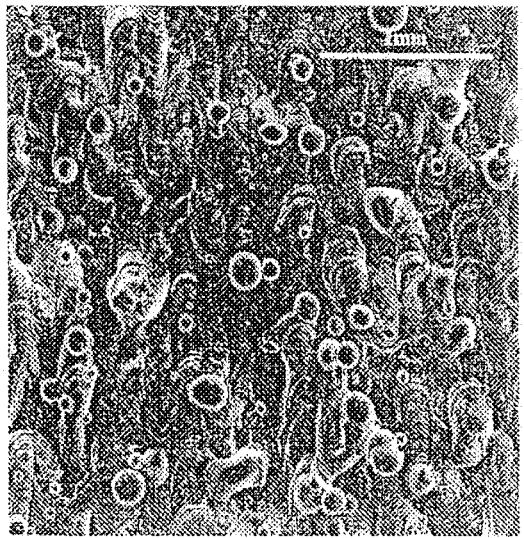
Figure 19A:
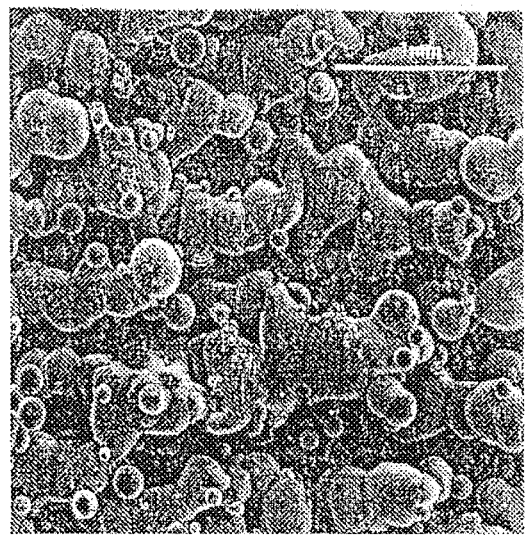
Figure 19B:
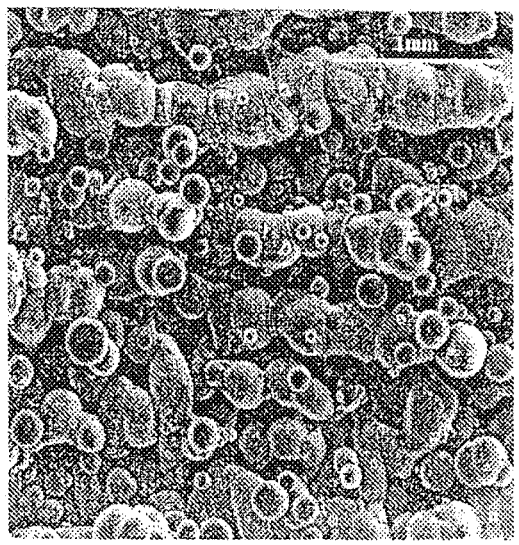
Figure 20A:
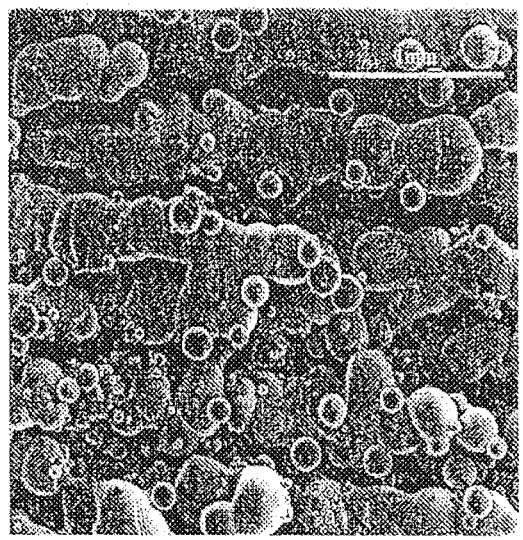
Figure 20B:
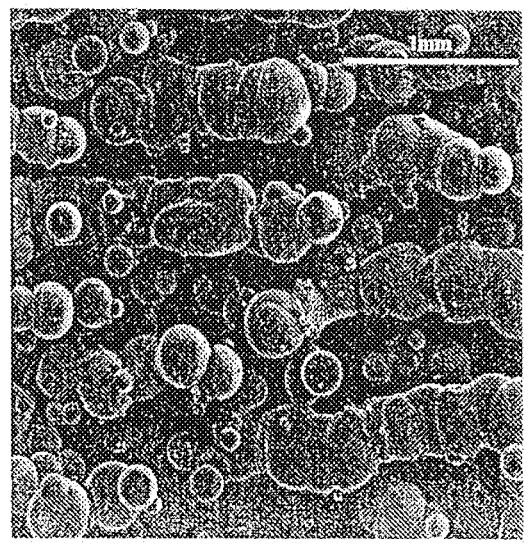
Figure 21A:
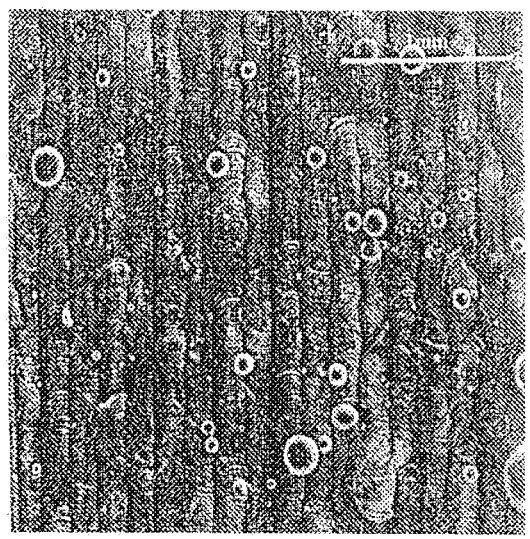
Figure 21B:
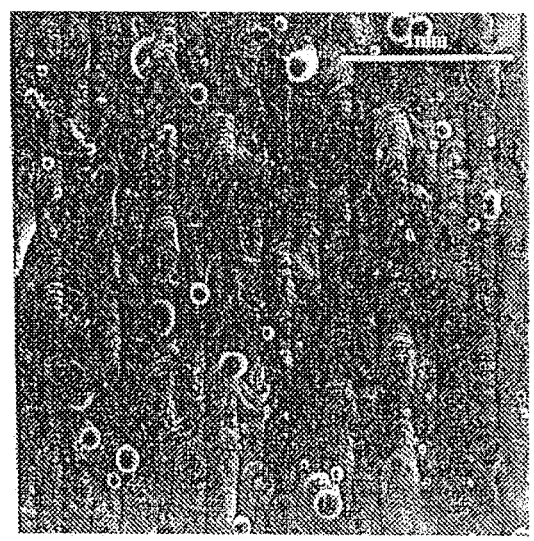
Figure 22A:
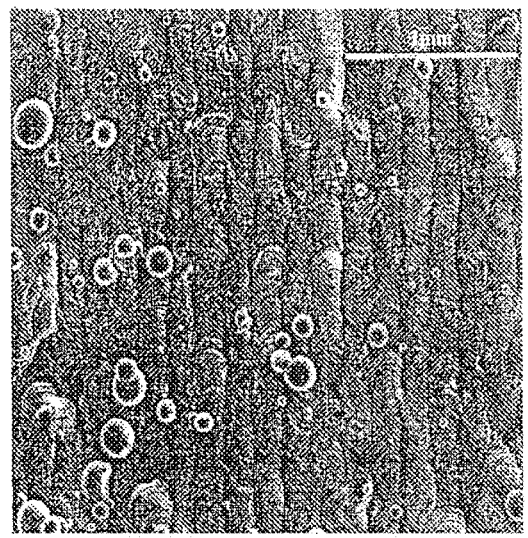
Figure 22B:
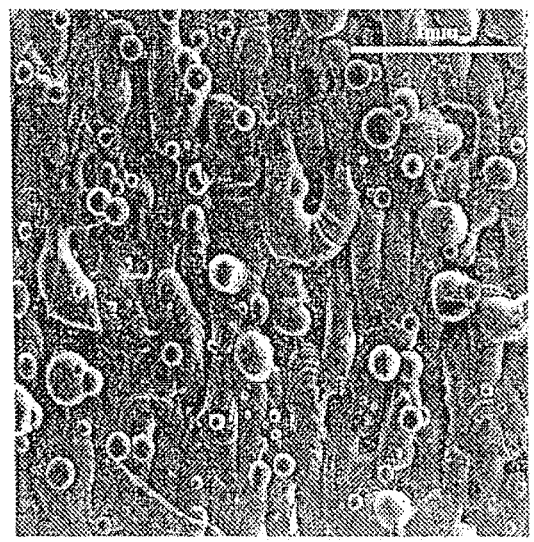
Figure 23A:
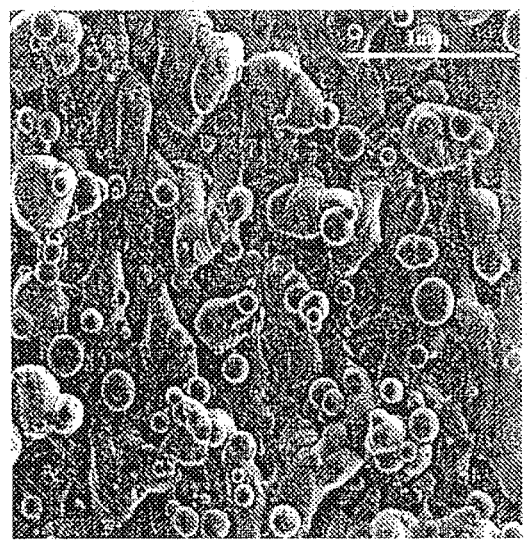
Figure 23B:
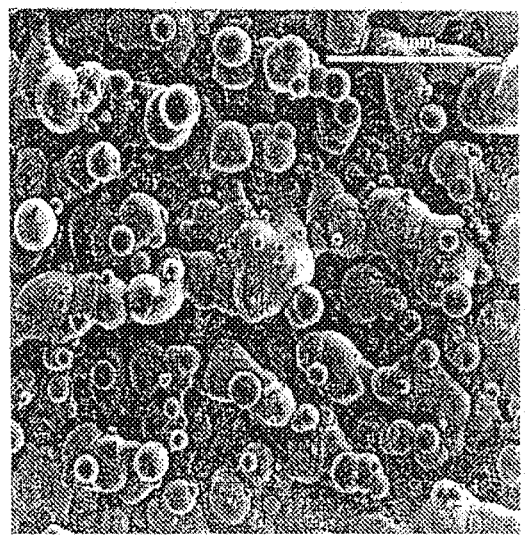
Figure 24A:
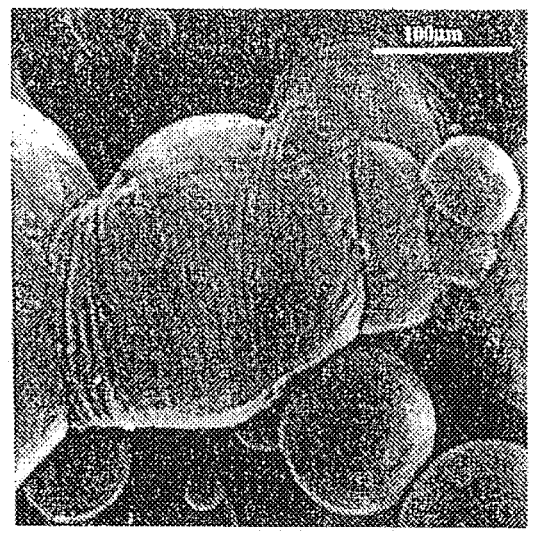
Figure 24B:
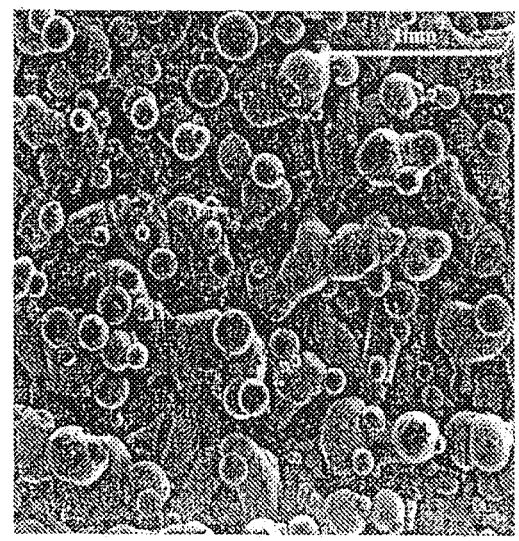
Figure 25:
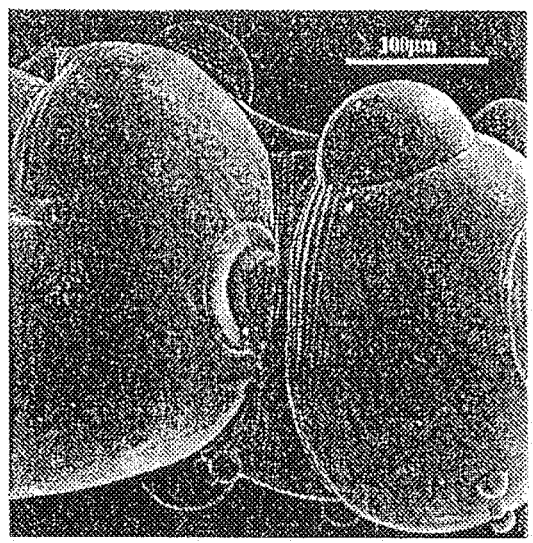

FIG. 16A shows Ti on CoCr (Single Layer; SEM Micrograph) v=160 mms-$^1$;
FIG. 16B shows Ti on CoCr (Single Layer; SEM Micrograph) v=160 mms-$^1$;
FIG. 17A shows Ti on CoCr (Single Layer; SEM Micrograph) v=170 mms-$^1$;
FIG. 17B shows Ti on CoCr (Single Layer; SEM Micrograph) v=180 mms-$^1$;
FIG. 18A shows Ti on CoCr (Single Layer; SEM Micrograph) v=190 mms-$^1$;
FIG. 18B shows Ti on CoCr (Single Layer; SEM Micrograph) v=200 mms-$^1$;
FIG. 19A shows Ti on CoCr (Single Layer; SEM Micrograph) v=210 mms-$^1$;
FIG. 19B shows Ti on CoCr (Single Layer; SEM Micrograph) v=220 mms-$^1$;
FIG. 20A shows Ti on CoCr (Single Layer; SEM Micrograph) v=230 mms-$^1$;
FIG. 20B shows Ti on CoCr (Single Layer; SEM Micrograph) v=240 mms-$^1$;
FIG. 21A shows Ti on Ti (Single Layer; SEM Micrograph) v=160 mms-$^1$;
FIG. 21B shows Ti on Ti (Single Layer; SEM Micrograph) v=170 mms-$^1$;
FIG. 22A shows Ti on Ti (Single Layer; SEM Micrograph) v=190 mms-$^1$;
FIG. 22B shows Ti on Ti (Single Layer; SEM Micrograph) v=200 mms-$^1$;
FIG. 23A shows Ti on Ti (Single Layer; SEM Micrograph) v=220 mms-$^1$;

FIG. 23B shows Ti on Ti (Single Layer; SEM Micrograph) v=230 mms$^{-1}$;

FIG. 24A shows Ti on Ti (Single Layer; SEM Micrograph) v=240 mms$^{-1}$;

FIG. 24B shows Ti on Ti (Single Layer; SEM Micrograph) v=240 mms$^{-1}$;

The method according to the present invention can produce surface structures on all powder/baseplate combinations with careful selection of process parameters.

As described above, the process is carried out on flat baseplates that provide for easy powder delivery in successive layers of around 100 μm thickness. Control of powder layer thickness is very important if consistent surface properties are required. The application of this technology can also be applied to curved surfaces such as those found in modern prosthetic devices; with refinements being made to the powder layer technique.

The structures have all received ultrasonic and aqueous cleaning. On close examination, the resultant porous surfaces produced by the Direct Laser Remelting process exhibit small particulates that are scattered throughout the structure. It is unclear at this stage whether these particulates are bonded to the surface or loosely attached but there are means to remove the particulates if required.

The Direct Laser Remelting process has the ability to produce porous structures that are suitable for bone in-growth applications. The powdered surfaces have undergone considerable thermal cycling culminating in rapid cooling rates that have produced very fine dendritic structures (e.g. FIGS. 13A to 13D).

The Direct Laser Remelting process can produce effective bone in-growth surfaces and the manufacturing costs are reasonable.

In the preceding examples, the object has been to provide a porous structure on a base but the present invention can also be used to provide a non-porous structure on such a base to form a three-dimensional structure. The same techniques can be utilized for the materials concerned but the laser processing parameters can be appropriately selected so that a substantially solid non-porous structure is achieved.

Again, a technique can be used to deposit the powder onto a suitable carrier, for example a mold, and to carry out the process without the use of a base so that a three-dimensional structure is achieved which can be either porous, as described above, or non-porous if required.

Additionally, the porosity of successive layers of powder can be varied by either creating a specific type of unit cell or manipulating various dimensions of a given unit cell.

There have been a number of studies to determine the optimum pore structure for maximization of bone in-growth on prostheses. The general findings suggest that optimum porosity is between approximately 20% and 40%, and aim to mid value with a mean volume percent of voids of about 70%. The preferred pore structure is interconnected, with a minimum pore size between about 80 μm and 100 μm and a maximum pore size between 80 μm and 800 μm. The structured thickness for in-growth is 1.4-1.6 mm, but can be larger or smaller depending on the application.

In the present invention porous structures are built in the form of a plurality of unit cells. Many designs of unit cells are possible to give the shape, type, degree, and size of porosity required. Such unit cell designs can be dodecahedral, octahedral, diamond, as well as many other various shapes. Additionally, besides regular geometric shapes as discussed above the unit cells of the present invention may be configured to have irregular shapes where various sides and dimensions have little if any repeating sequences. The unit cells can be configured to constructs that closely mimic the structure of trabecular bone for instance. Unit cells can be space filling, all the space within a three-dimensional object is filled with cells, or interconnected where there may be some space left between cells but the cells are connected together by their edges.

The cells can be distributed within the construct a number of ways. Firstly, they may be made into a block within a computer automated design system where the dimensions correspond to the extent of the solid geometry. This block can then be intersected with the geometry representing the component to produce a porous cellular representation of the geometry. Secondly, the cells may be deformed so as to drape over an object thus allowing the cells to follow the surface of the geometry. Thirdly, the cells can be populated through the geometry following the contours of any selected surface.

The unit cell can be open or complete at the surface of the construct to produce a desired effect. For instance, open cells with truncated lattice struts produce a surface with a porosity and impart the surface with some degree of barb.

Modifying the lattice strut dimensions can control the mechanical strength of the unit cell. This modification can be in a number of key areas. The lattice strut can be adjusted by careful selection of build parameters or specifically by changing the design of the cross-section of each strut. The density of the lattice can similarly be adjusted by modification of the density of the unit cells as can the extent and shape of porosity or a combination thereof. Clearly the overall design of the unit cell will also have a significant effect of the structural performance of the lattice. For instance, dodecahedral unit cells have a different mechanical performance when compared to a tetrahedral (diamond) structure.

Figure 32A:
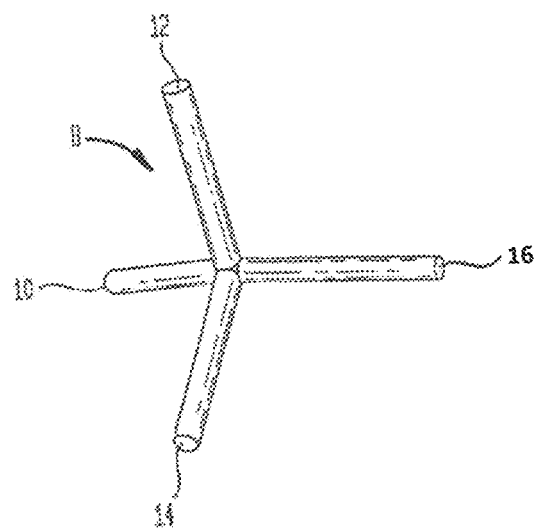
FIG. 32A illustrates one embodiment of a unit cell of the present invention.
Figure 32B:
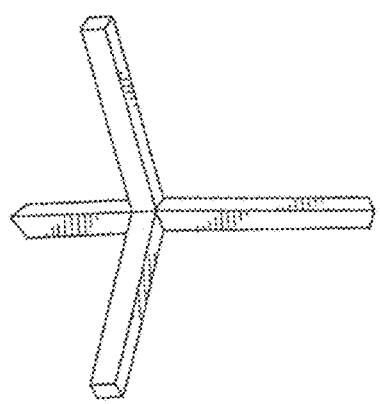
FIG. 32B illustrates an alternate embodiment of a unit cell of the present invention.

As shown in FIGS. 32A and 32B, in a tetrahedron 8, each point 10, 12, 14, and 16 is the same distance from the neighboring point. This structure is analogous to the arrangements of the carbon atoms in diamond.

Each carbon atom in the diamond is surrounded by four nearest neighbors. They are connected together by bonds that separate them by a distance of 1.5445 angstroms. The angles between these bonds are 109.5 degrees. As a result, the central atom and its neighbors form a tetrahedron. This geometry as in the case discussed herein may then be scaled to appropriate value for the pore construct required.

The two key parameters used to define the relations regarding height, surface area, space height, volume of tetrahedron, and the dihedral angle of a tetrahedron are the strand length of the tetrahedron and, i.e., the diameter or height and width, cross section area of the strand i.e., strut. These two parameters control the pore size and porosity of the structure. The parameter editor and relation editor within a typical CAD system can be used to control these parameters. Hence, by changing the parameters one can change the fundamental properties of the porous structure. As shown in FIGS. 32A and 32B, the diamond structure may have a circular cross-section strands or square cross-section strands. Although only two strand cross-sections are illustrated, strands having various cross-sections are possible. Further, this is true with most of the designs for the unit cell.

Figure 32C:
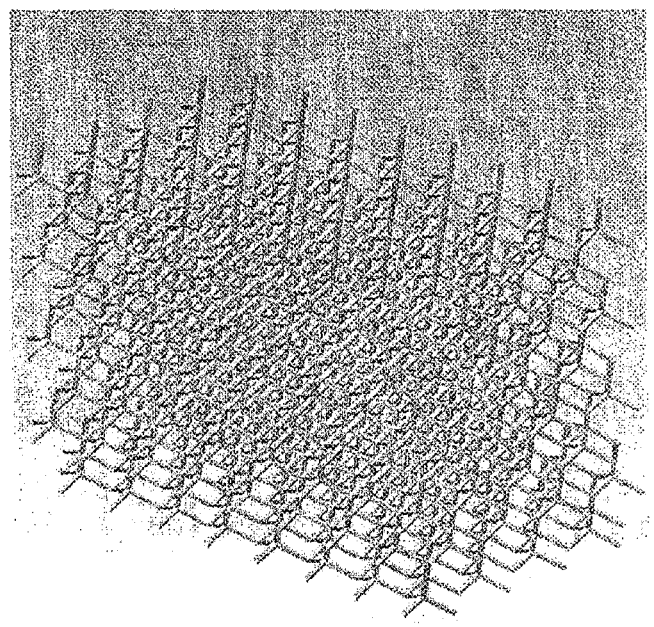
FIG. 32C illustrates a lattice structure formed using a plurality of unit cells illustrated in FIG. 32BB.
Figure 33:
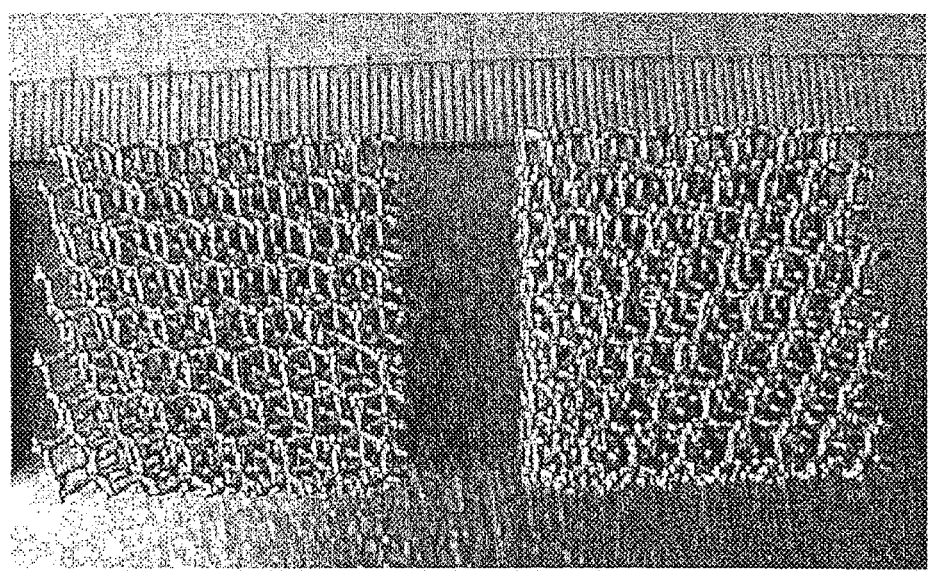
FIG. 33 illustrates lattice structures with and without laser beam compensation formed using the unit cells illustrated in FIG. 32B.

To create the mesh as shown in FIG. 32C, the unit cell can be instanced across the 3-D space to produce the required lattice. FIG. 33 illustrates a view of a diamond lattice structure with and without laser beam compensation. Laser beam compensation essentially allows the diameter of the beam to be taken into account. Without it the constructed geometry is one beam diameter too wide as the beam traces out the contour of the particular section being grown. When laser beam compensation is utilized, the contour is offset half a beam diameter all around the constructed geometry which is represented in the CAD file. Although various parameters may be used, the parameters employed to create the lattices of FIG. 33 include a laser power of 90.5 watts with an exposure time of 1,000 μsec from a point distance of 90 μm. Table 1 illustrates various other examples of parameters that may be used to create various unit cells.

TABLE 1

| Part build on SLM | edge length μm | diameter μm | laser power Watts | exposure μsec | point distance μm |
|---|---|---|---|---|---|
| Diamond Structure | 2000 | 200 | 90.5 | 1000 | 90 |
| Diamond Structure with compensation | 2000 | 200 | 90.5 | 1000 | 90 |
| Dodecahedron Structure | 1500 | 200 | 68.3 | 1000 | 90 |
| Dodecahedron Structure with compensation | 1500 | 200 | 68.3 | 1000 | 90 |
| Modified Truncated Octahedron | 1500 | 200 | 90.5 | 1000 | 90 |

Figure 34A:
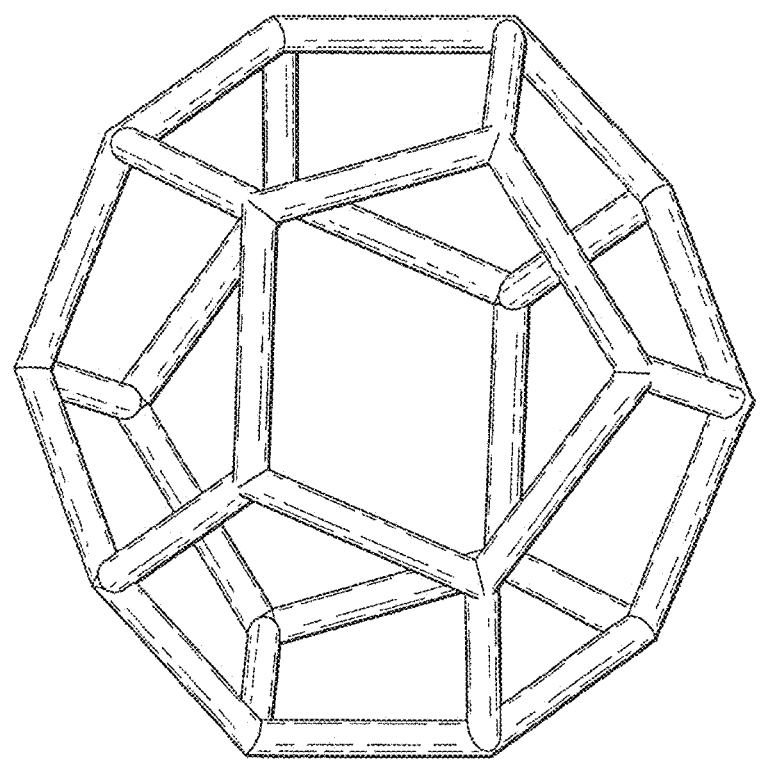
FIG. 34A illustrates an alternate embodiment of a unit cell of the present invention.
Figure 34B:
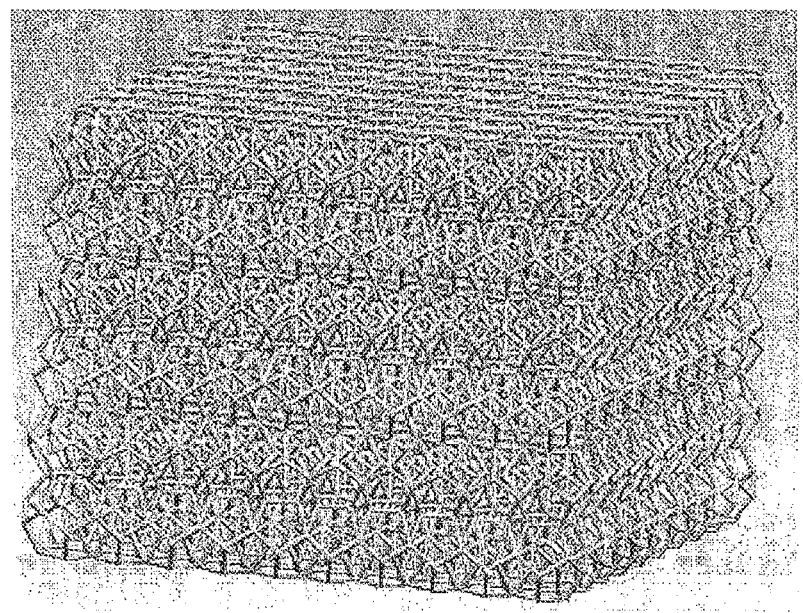
FIG. 34B illustrates a lattice structure formed using a plurality of unit cells illustrated in FIG. 34A.

As shown in FIGS. 34A and 34B, the porous structure can also be created using a unit cell in the shape of a dodecahedron. The regular dodecahedron is a platonic solid composed of 20 polyhedron vertices, 30 polyhedron edges, and 12 pentagonal faces. This polyhedron is one of an order of five regular polyhedra, that is, they each represent the regular division of 3-dimensional space, equilaterally and equiangularly. This basic unit cell for a decahedron mesh can be built up in a CAD package using the following calculations and procedure. The dodecahedron has twelve regular pentagonal faces, twenty vertices, and thirty edges. These faces meet at each vertex. The calculations for a side length of a dodecahedron are given by simple trigonometry calculations and are known by those in the art.

In a method of use, a sweep feature is first used to model the dodecahedron structure by driving a profile along a trajectory curve. The trajectory curves are constructed from datum points corresponding to the vertices of the dodecahedron connected by datum curves. The type of profile remains constant along the sweep producing the model shown in FIG. 34A. The size and shape of the profile can be designed to suit the particular application and the required strut diameter. Once a particular unit cell has been designed, the cell can be instanced to produce a regular lattice as shown in FIG. 34B. As a dodecahedron is not spaced filling, meshes are produced by simple offsetting of the unit cell and allowing some of the struts to overlap. This method of overlapping may be used with the alternate shapes of the unit cell.

Figure 35:
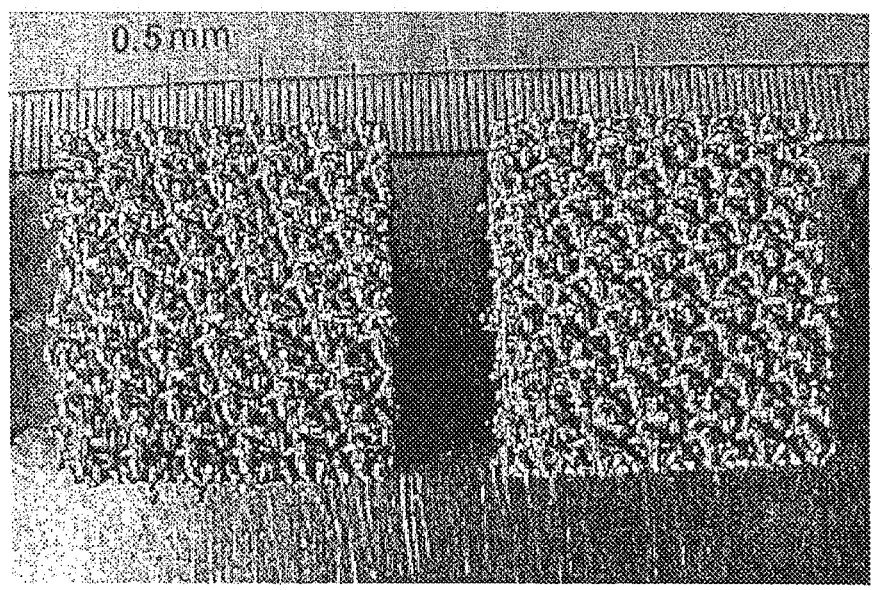
FIG. 35 illustrates lattice structures formed with and without laser beam compensation.

FIG. 35 shows a view of a dodecahedron (with and without laser beam compensation, from left to right) structure using selective laser melting process parameters. Once again, although the parameters may be varied, the lattices of FIG. 35 were created using the following parameters; a laser power of 90.5 watts, exposure of the powder for 1,000 μsec and a point distance of 90 μm.

Figure 36A:
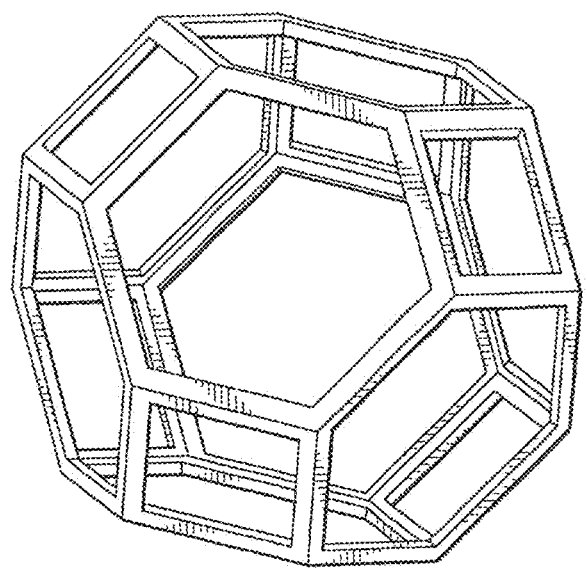
FIG. 36A illustrates an alternate embodiment of a unit cell of the present invention.
Figure 36B:
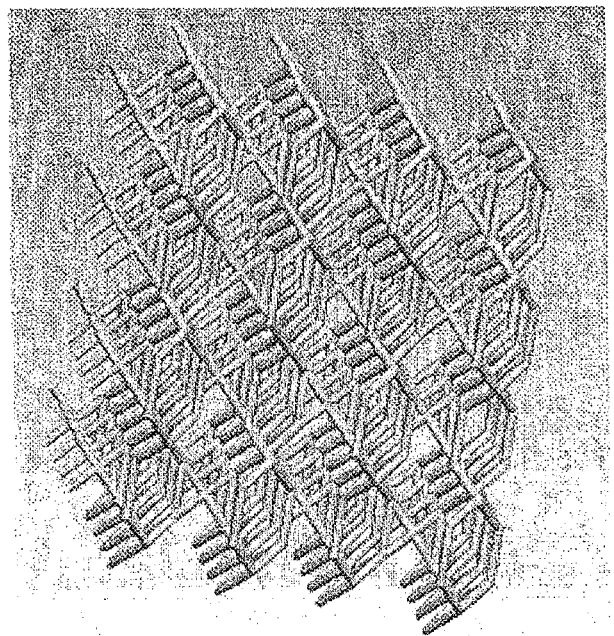
FIG. 36B illustrates a lattice structure formed using a plurality of the unit cells illustrated in FIG. 36A.
Figure 37A:
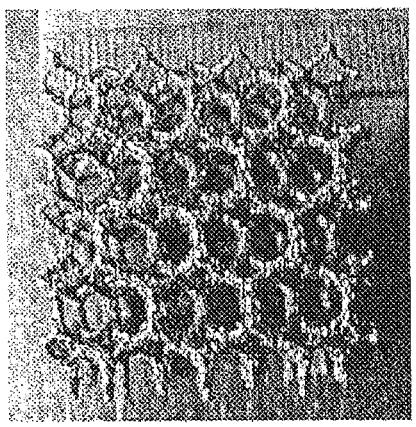
FIGS. 37A and 37B illustrate actual lattice structures formed using a plurality of unit cells represented in FIG. 36A.
Figure 37B:
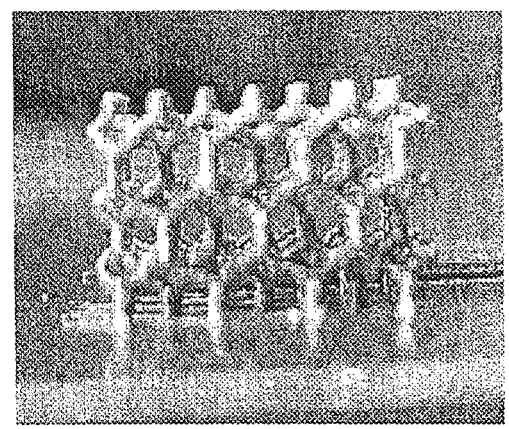

As shown in FIGS. 36A and 36B, the unit cell of the present invention may also be constructed in the shape of a truncated octahedron. A truncated octahedron has eight regular hexagonal faces, six regular square faces, twenty-four vertices, and thirty-six edges. A square and two hexagons meet at each vertex. When the octahedron is truncated, it creates a square face replacing the vertex, and changes the triangular face to a hexagonal face. This solid contains six square faces and eight hexagonal faces. The square faces replace the vertices and thus this leads to the formation of the hexagonal faces. It should be noted here that these truncations are not regular polyhedra, but rather square-based prisms. All edges of an Archimedean solid have the same length, since the features are regular polygons and the edges of a regular polygon have the same length. The neighbors of a polygon must have the same edge length, therefore also the neighbors and so on. As with previous unit cells, various dimensions such as the octahedron height, octahedron volume, octahedron surface area, octahedron dihedral angle, and truncated octahedron volume, truncated octahedron height, truncated octahedron area, truncated octahedron volume, truncated octahedron dihedral angle can be determined by simple trigonometry and are known by those skilled in the art.

Figure 38A:
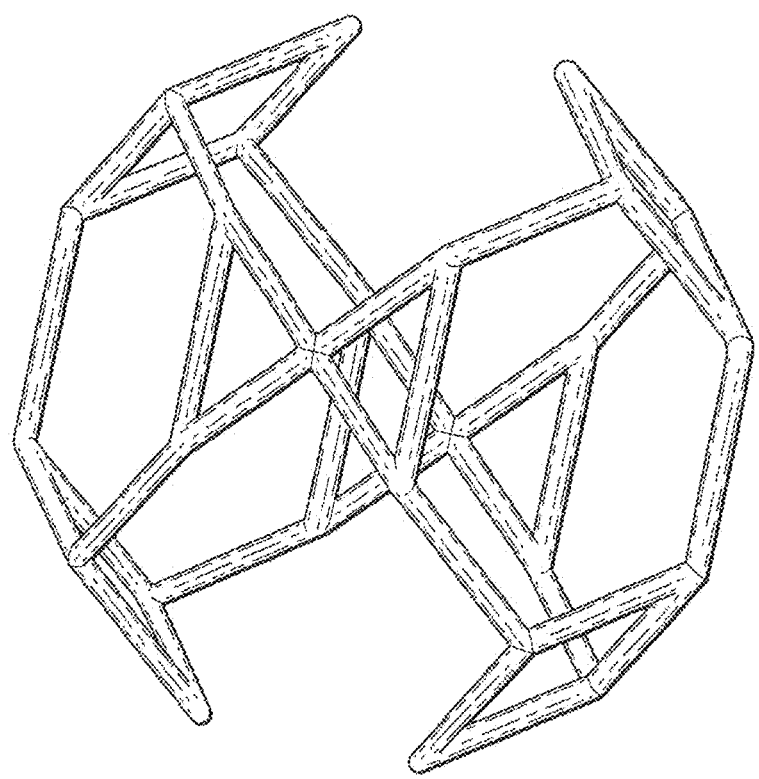
FIG. 38A illustrates an additional embodiment of a unit cell of the present invention.
Figure 38B:
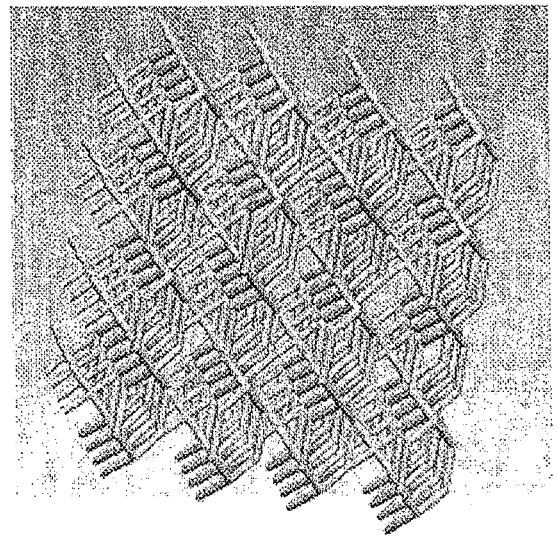
FIG. 38B illustrates a lattice structure created using a plurality of unit cells illustrated in FIG. 38A.

In a method of use, a CAD model of the truncated octahedron is constructed using the sweep feature and calculations and dimensions are incorporated using basic trigonometry. Two tessellate the unit cell, the unit cell is first reoriented to enable easy tessellation and to reduce the number of horizontal struts in the model. Further, the model can be modified to remove all of the horizontal struts as shown in FIG. 38A. The modified structure is reproduced in order to save file size in the Stereolithography ("STL") format of the program. Next, in order to create the unit cells, the method of using a laser melting process is performed. In one preferred embodiment, the parameter chosen includes a laser power of 90.5 watts, an exposure of 1000 μsec with a point distance of 90 μm. FIG. 38B illustrates a lattice structure formed using a plurality of individual truncated octahedron. As discussed earlier, the removal of various struts can create a barb effect on the exterior surface of the lattice structure.

Figure 39A:
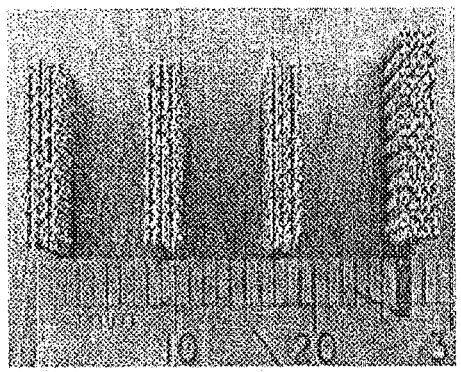
FIG. 39A illustrates lattice structures created using unit cells illustrated in FIG. 38A with varying exposure time.
Figure 39B:
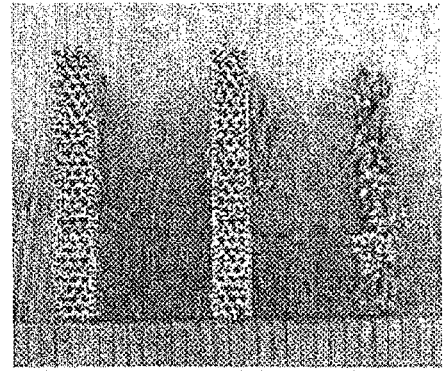
FIG. 39B illustrates lattice structures created using unit cells illustrated in FIG. 32A with varying exposure time.
Figure 39C:
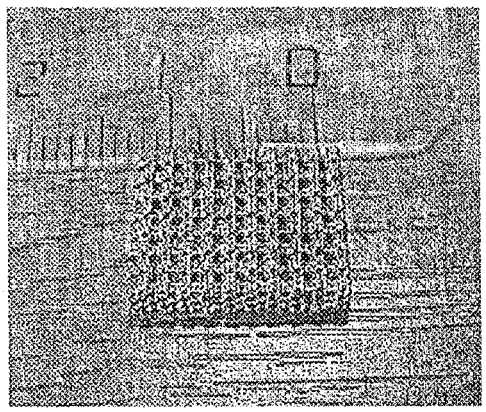
FIG. 39C illustrates a side view of an embodiment of FIG. 39A.
Figure 39D:
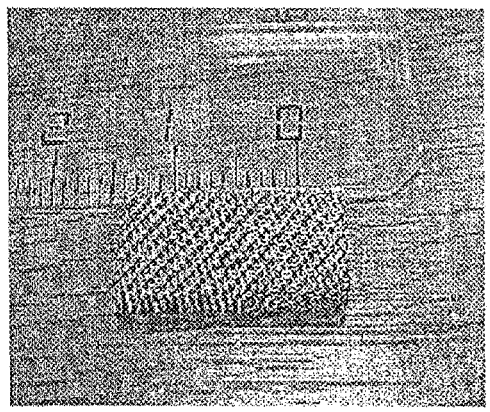
FIG. 39D illustrates a side view of a lattice structure illustrated in FIG. 39B.

As shown in FIGS. 39A-D, it is possible to reduce the size of the unit cell geometry. Also as shown, it is possible to manufacture open cell structures with unit cell sizes below 1 millimeter. FIG. 39A illustrates truncated octahedron structures manufactured using the laser melting process. All the structures were created using a laser power of 90.5 W, and a point distance of 90 μm; however, from left to right, the exposure time was varied from 500 μsec and 100 μsec. FIG. 39B illustrates similar structures and parameters as used with FIG. 39A, however, the unit cell used to create the lattice is diamond. FIGS. 39C and 39D illustrate a side view of the truncated octahedron structure of FIG. 39A and the diamond structure of FIG. 39B, respectively. Table 2 includes various manufacturing parameters used to construct various unit cell structure.

TABLE 2

| Part build on SLM | Strand length μm | Length of strand c/s μm | Width of strand c/s μm | Laser Power Watts | Exposure μsec | Point distance μm |
|---|---|---|---|---|---|---|
| Truncated Octahedron | 3000 | 50 | 50 | 90.5 | 500 | 90 |
| Truncated Octahedron | 3000 | 50 | 50 | 90.5 | 300 | 90 |

TABLE 2-continued

| Part build on SLM | Strand length μm | Length of strand c/s μm | Width of strand c/s μm | Laser Power Watts | Exposure μsec | Point distance μm |
|---|---|---|---|---|---|---|
| Truncated Octahedron | 3000 | 50 | 50 | 90.5 | 100 | 90 |
| Truncated Octahedron | 1000 | 50 | 50 | 90.5 | 500 | 90 |
| Truncated Octahedron | 1000 | 50 | 50 | 90.5 | 300 | 90 |
| Truncated Octahedron | 1000 | 50 | 50 | 90.5 | 100 | 90 |
| Diamond Structure | 700 | 50 | 50 | 90.5 | 500 | 90 |
| Diamond Structure | 700 | 50 | 50 | 90.5 | 300 | 90 |
| Diamond Structure | 700 | 50 | 50 | 90.5 | 100 | 90 |

Figure 40:
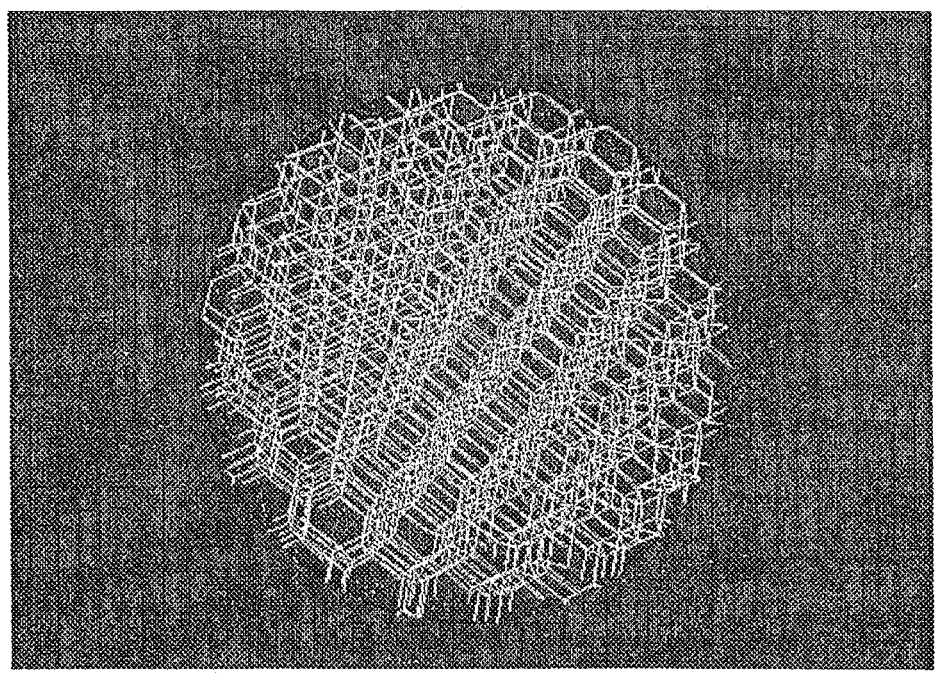
FIG. 40 is a representation of a lattice structure created using a plurality of the unit cells illustrated in FIG. 38A with random perturbation.
Figure 41:
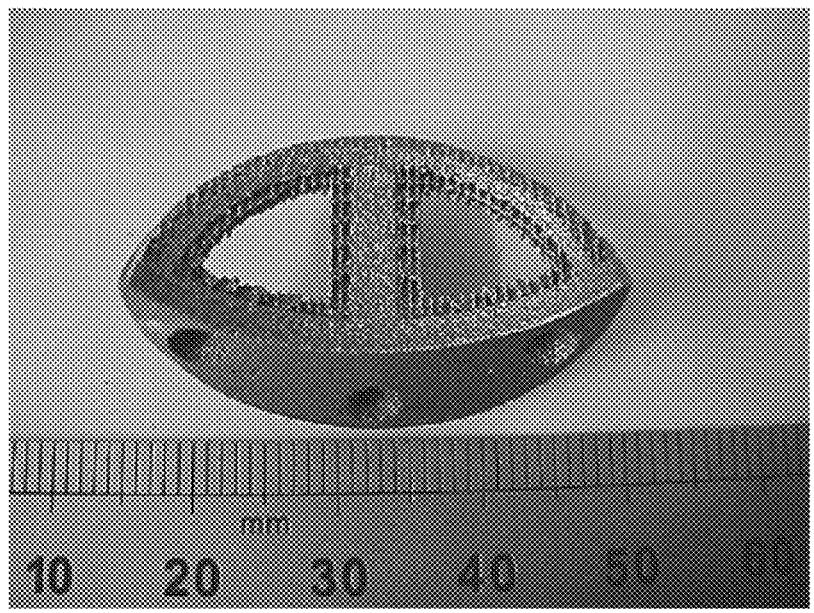
FIG. 41 illustrates graduation of a solid to a lattice build.
Figure 42:
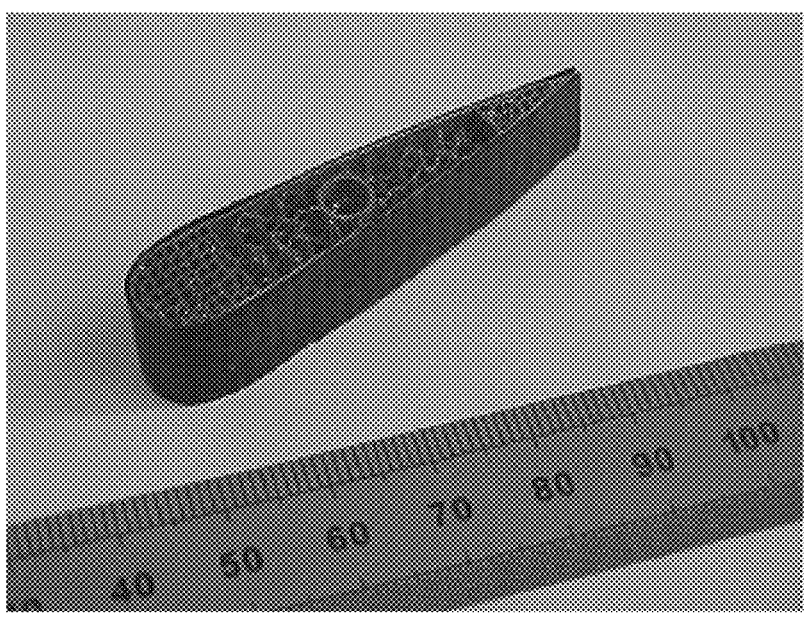
FIG. 42 illustrates a graduation from one lattice density to another.

Random representative geometries may be made from the current regular unit cells by applying a random X, Y, Z perturbation to the vertices of the unit cells. One such example can be seen in FIG. 40. In another aspect of the present invention, various freestanding constructs can be generated. In a typical manufacturing procedure for the production of a construct, in this case a femoral hip component, the laser melting of appropriate metallic powders is employed. Table 3 listed below, includes various examples of equipment and material used in the construct, as well as typical software utilized.

TABLE 3

| Equipment/Software | Description |
|---|---|
| Magics V8.05 (Materialise) | CAD software package used for manipulating STL files and preparing builds for Rapid Manufacture (RM) |
| Python | Programming language |
| Equipment/Software | Description |
| MCP Realizer | SLM machine using 100 w fibre laser |
| 316 L gas atomized metal powder Osprey Metal Powders Ltd | Metal powder with an mean particle size of approximately 40 μm |

Figure 43A:
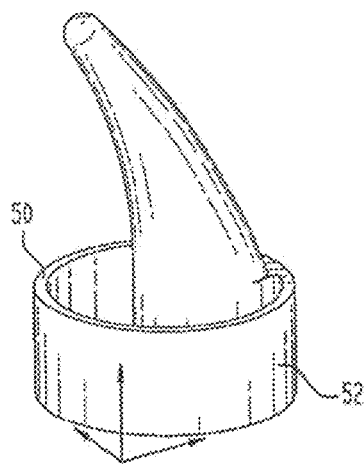
FIG. 43A illustrates a femoral hip component.
Figure 43B:
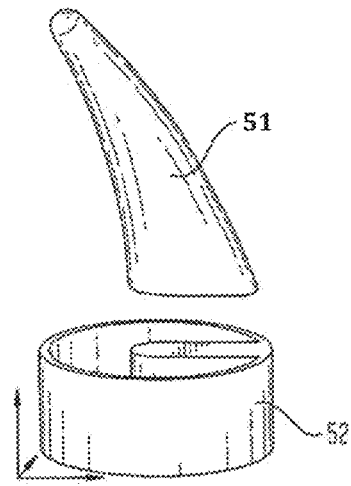
FIG. 43B illustrates an exploded view of FIG. 43A.
Figure 44:
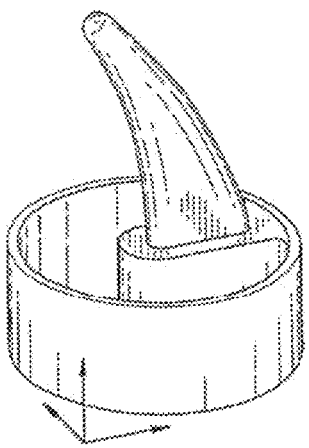
FIG. 44 illustrates the component of FIG. 43A with a reduced sized femoral attachment.
Figure 45:
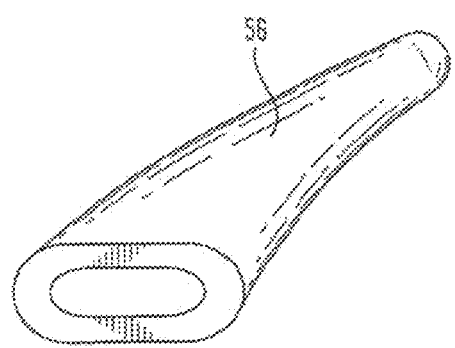
FIG. 45 illustrates a "jacket" created by the subtraction of the embodiment of FIG. 44 from the embodiment of FIG. 43A.

In one example of this procedure an STL file of hip component 50 is loaded into an engineering design package such as Magics, as shown in FIG. 43A. The femoral attachment 51 may then be segmented from the body 52 of the construct. The femoral attachment 51 may then be scaled down to 80% of its original size and reattached to the body 52 of the implant 50 as shown in FIG. 44. This permits the implant to act as a structural core for the surface coating. The selection of the amount of scaling or indeed the design of the core allows for the production of the required structural properties of the stem. Thus, the core may either be scaled down even more or less to meet the required needs of the implant. A Boolean operation may next be performed in Magics to subtract the reduced femoral attachment from the original. This creates a "jacket" 56 i.e., mold to be used as the interconnecting porous construct as shown in FIG. 45.

Figure 46A:
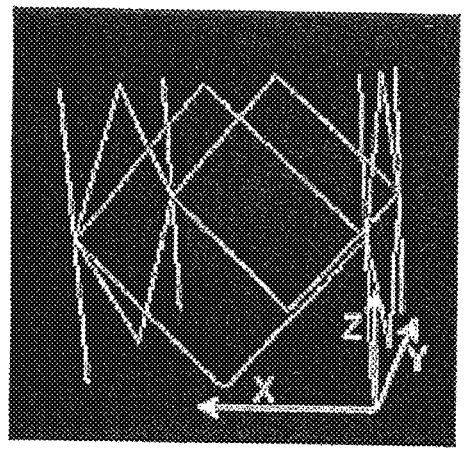
FIG. 46A illustrates one embodiment of a single unit cell for use in an open cellular lattice structure.
Figure 46B:
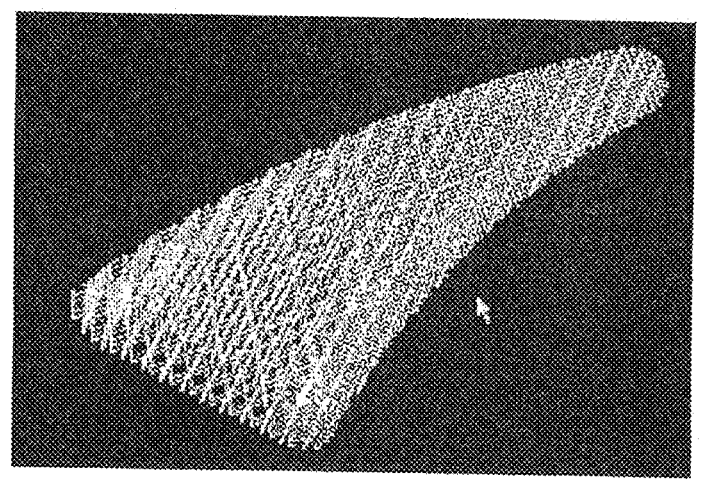
FIG. 46B illustrates an open cellular lattice structure.
Figure 47:
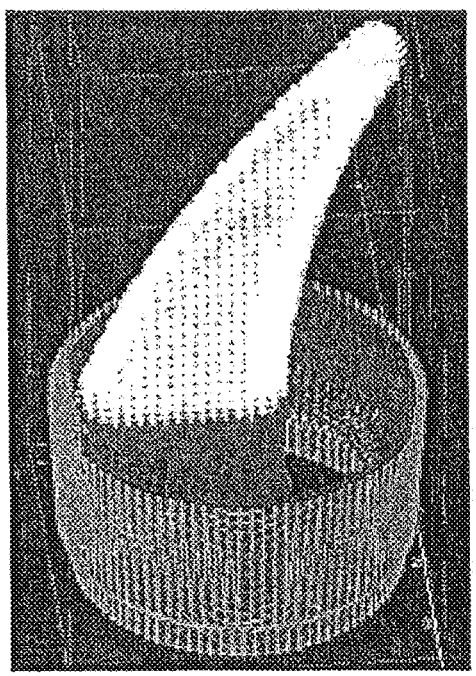
FIG. 47 illustrates the embodiment illustrated in FIG. 46B merged with the embodiment illustrated in FIG. 44.

Jacket 56 is processed via a bespoke application that populates STL shapes with repeating open cellular lattice structures (OCLS). The OCLS used in this instance is a repeating unit cell of size 1.25 millimeters and strand diameter 200 μm. FIG. 46A illustrates a representation of a single unit cell of the OCLS which will be used to populate jacket 56. The OCLS "jacket" 56 as shown in FIG. 46B will act as the porous surface coating of the femoral attachment 50. Once produced, the OCLS is sliced using a bespoke program written in the Python programming language with a layer thickness of 50 μm. The main body of the construct is then loaded into Fusco, a user interface for the MCP realizer. The file is then prepared for manufacture by slicing the file with a 50 μm layer thickness and applying the hatching necessary for building solid constructs. The component and OCLS femoral coating are then merged as shown in FIG. 47. The component may then be built on the SLM system as shown in FIG. 48A with typical process parameters being shown in table 4 below.

TABLE 4

| Feature | Slice height (μm) | Power (watts) | Exposure (μs) | $P_{dist}$ (μm) | $H_{dist}$ (mm) |
|---|---|---|---|---|---|
| Solid layer | 100 | 90.5 | 800 | 80 | 0.125 |
| Porous layer | 100 | 90.5 | 3500 | N/a (spot) | N/a |

Figure 48A:
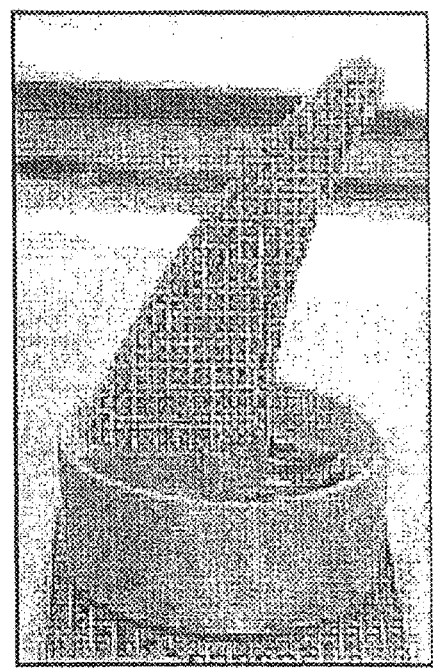
FIGS. 48A and 48B illustrate one embodiment of a finished product.
Figure 48B:
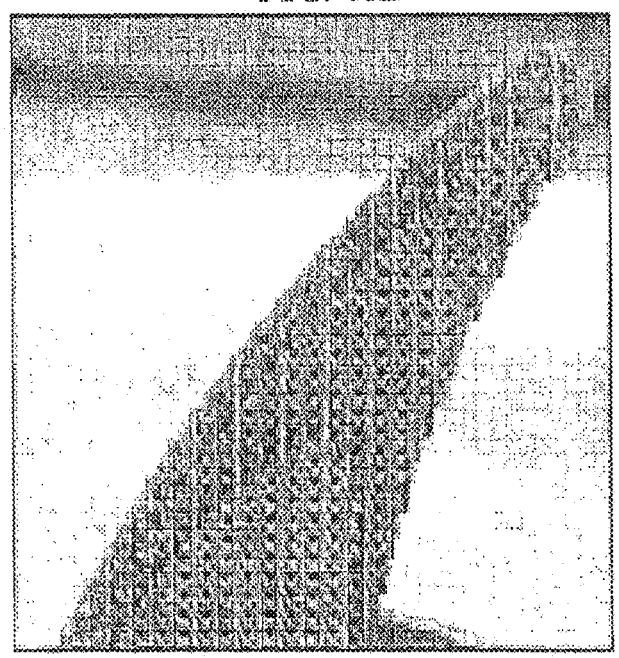
Figure 49A:
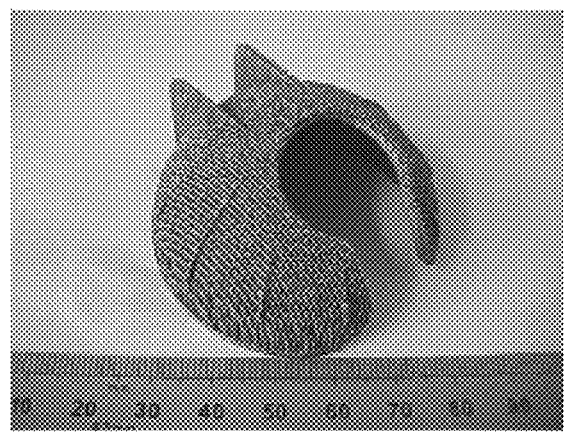
FIGS. 49A-49C illustrate an alternate embodiment of a finished product.
Figure 49B:
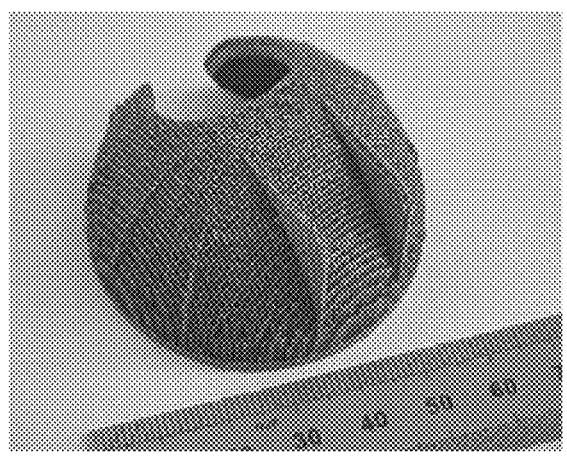
Figure 49C:
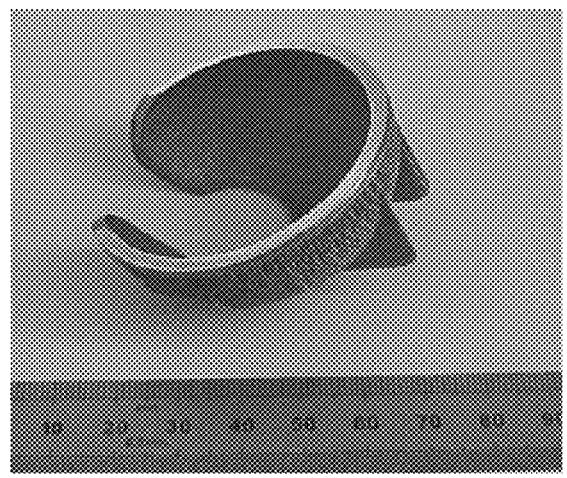
Figure 50A:
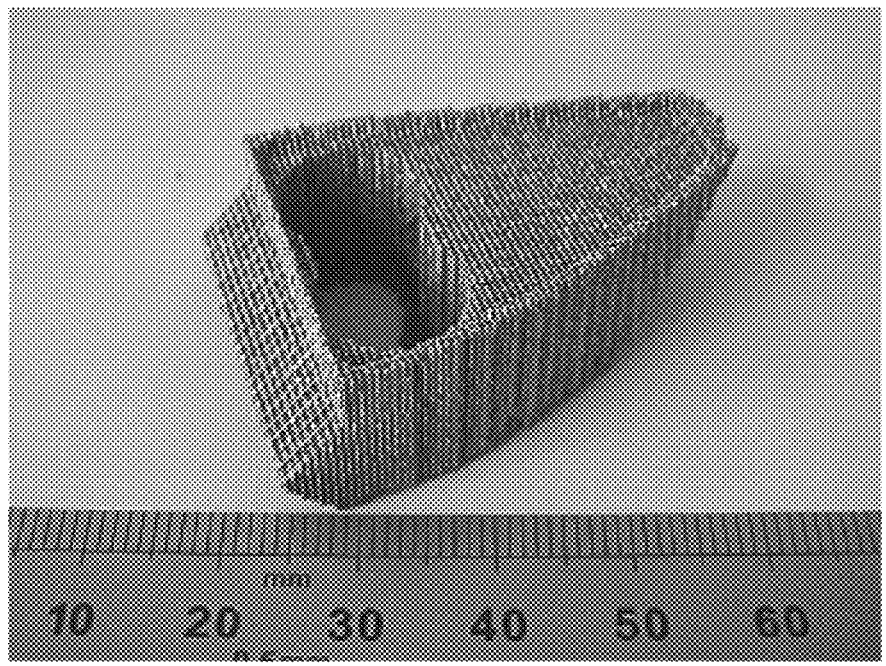
FIGS. 50A and 50B illustrate an alternate embodiment of a finished product.
Figure 50B:
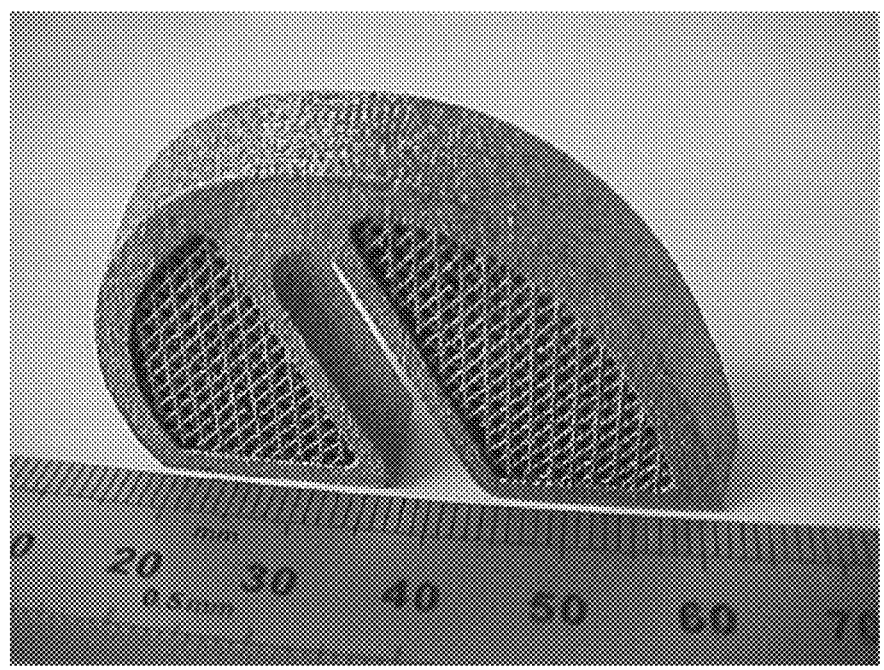
Figure 51A:
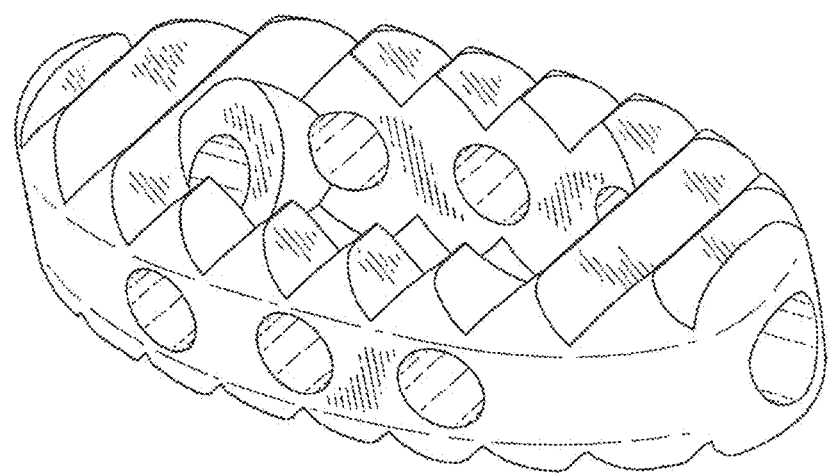
FIGS. 51A-51C illustrate an alternate embodiment of a finished product.
Figure 51B:
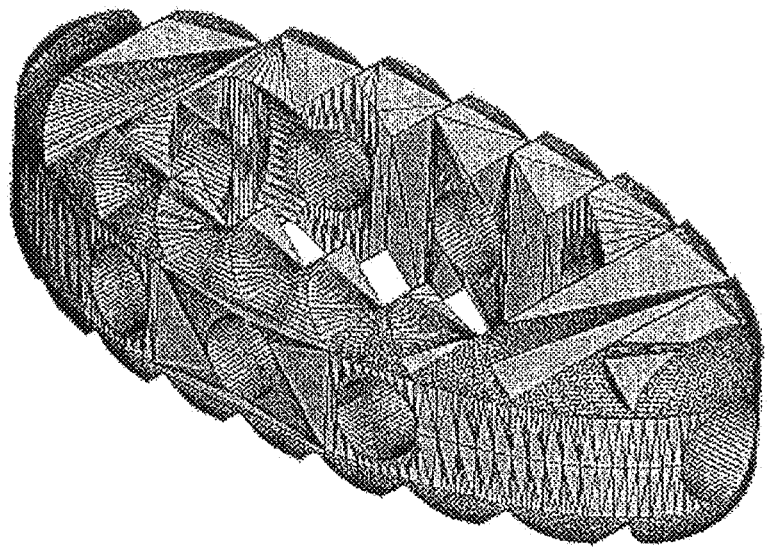
Figure 51C:
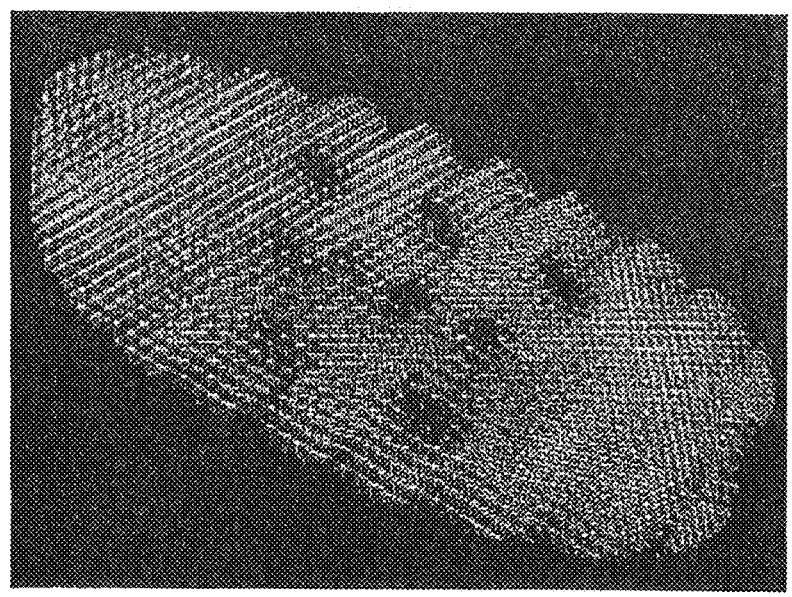
Figure 52A:
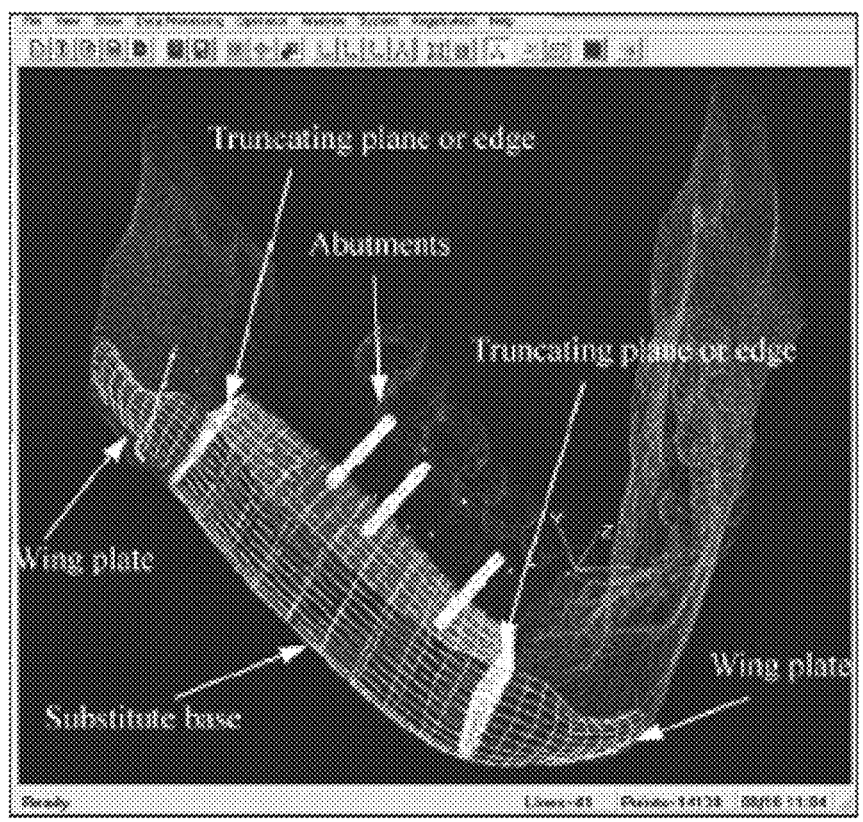
FIGS. 52A and 52B illustrate an alternate embodiment of a finished product.
Figure 52B:
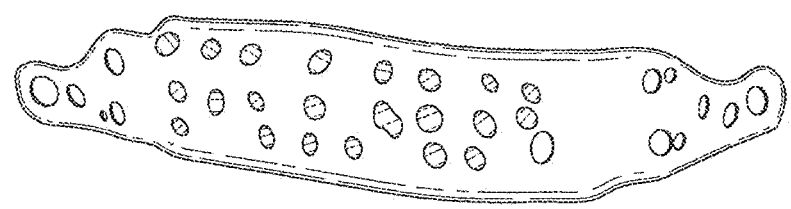
Figure 53:
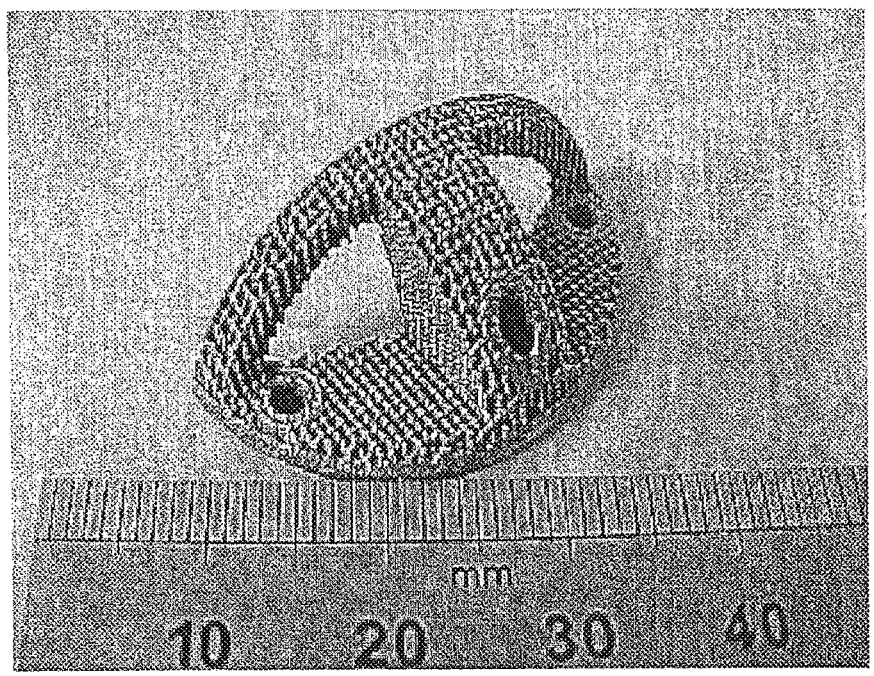
FIG. 53 illustrates an alternate embodiment of a finished product.
Figure 54:
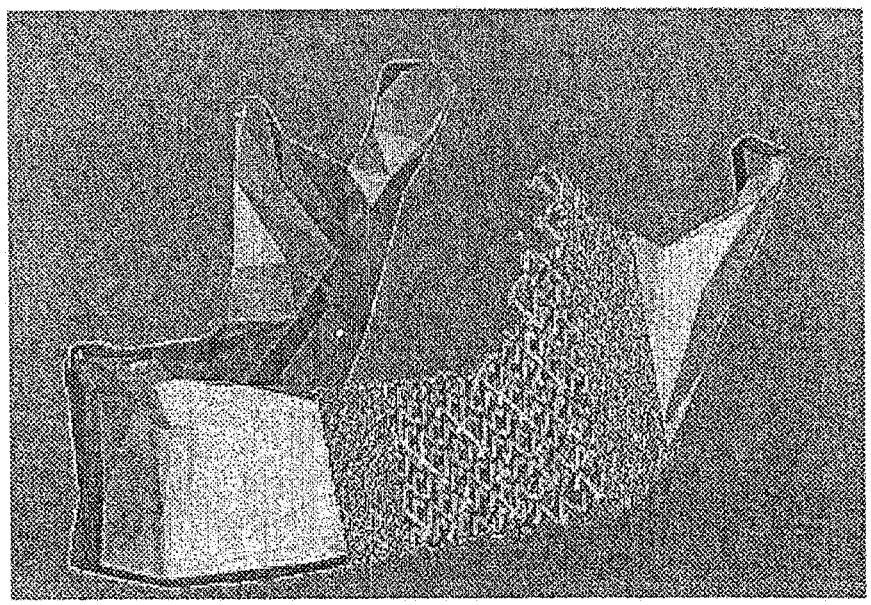
FIG. 54 illustrates an alternate embodiment of a finished product.
Figure 55A:
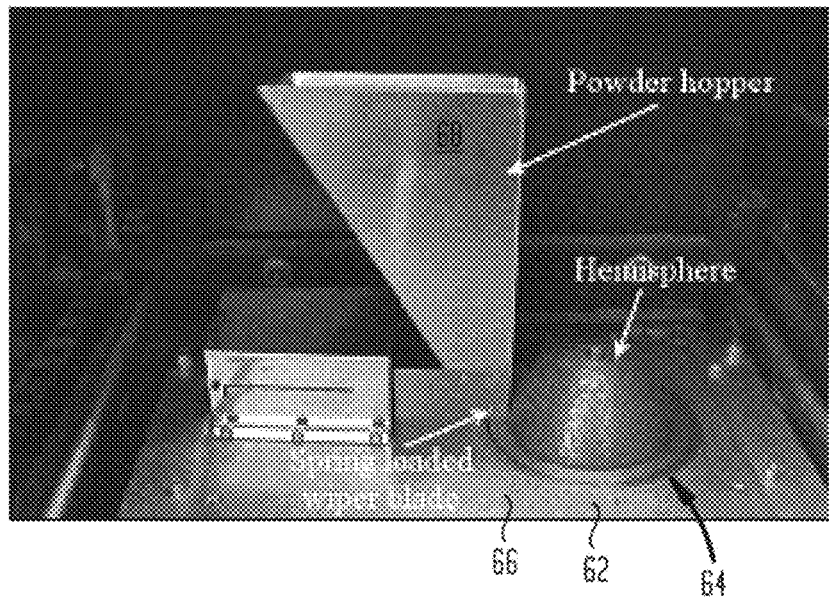
FIGS. 55A and 55B illustrate an apparatus used in conjunction with the present invention.
Figure 55B:
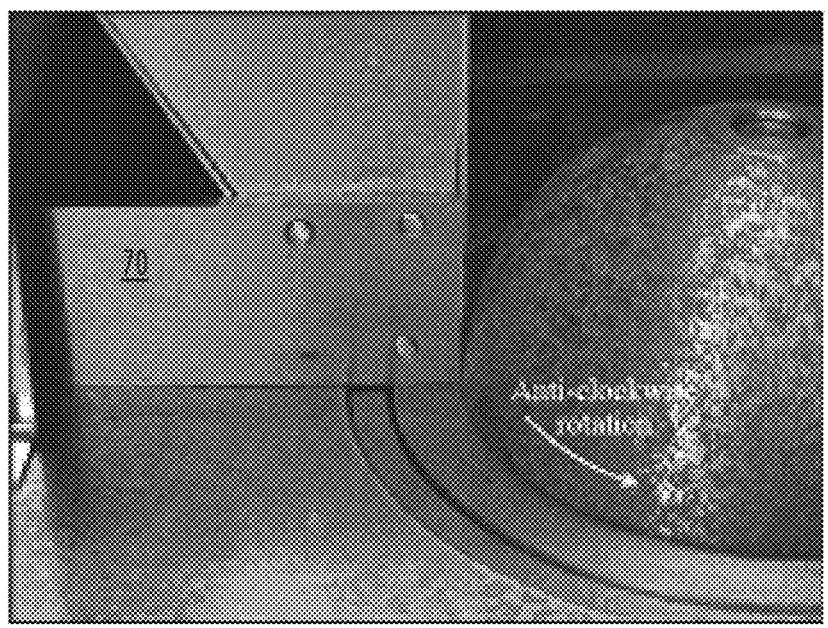
Figure 56:
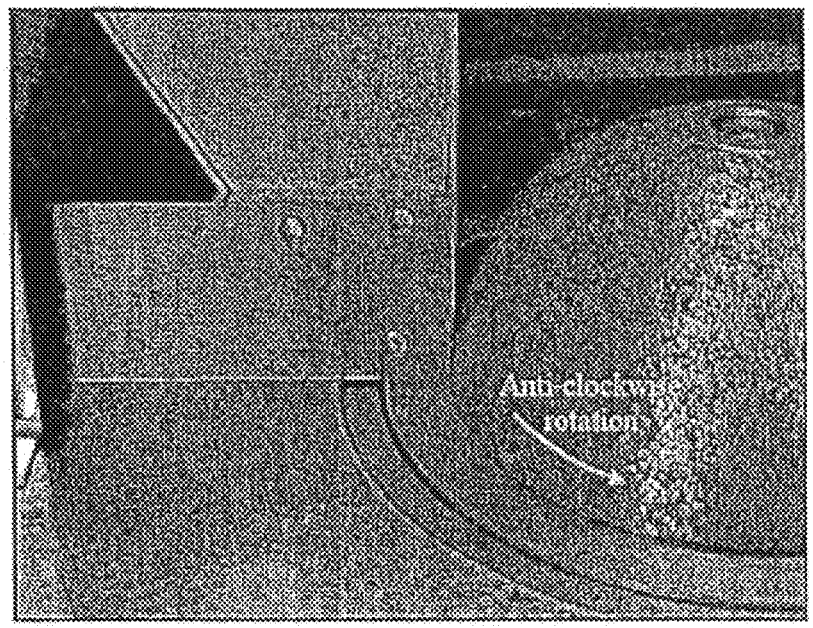
FIG. 56 illustrates a zoomed-in view of the embodiment illustrated FIG. 55B.
Figure 57:
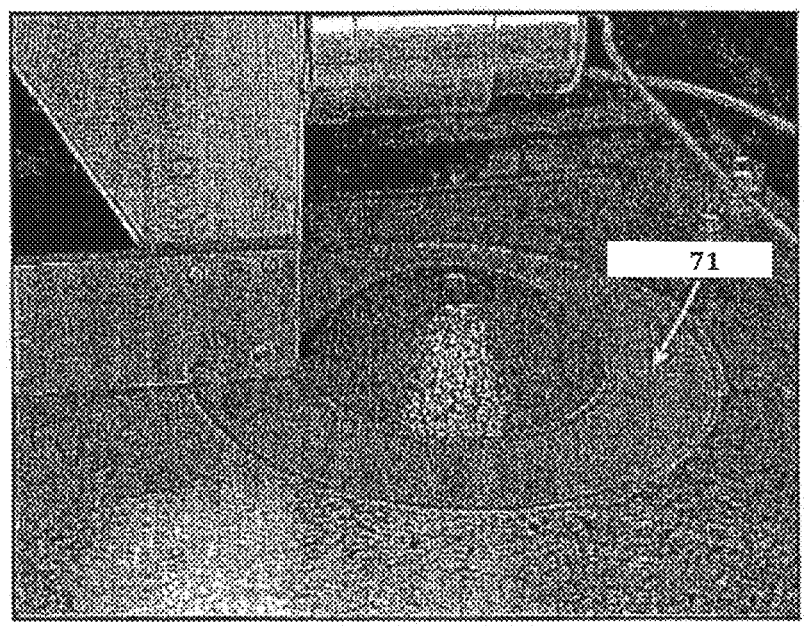
FIG. 57 illustrates a zoomed-in view of the apparatus illustrated in FIG. 55B, further along in the process.
Figure 58:
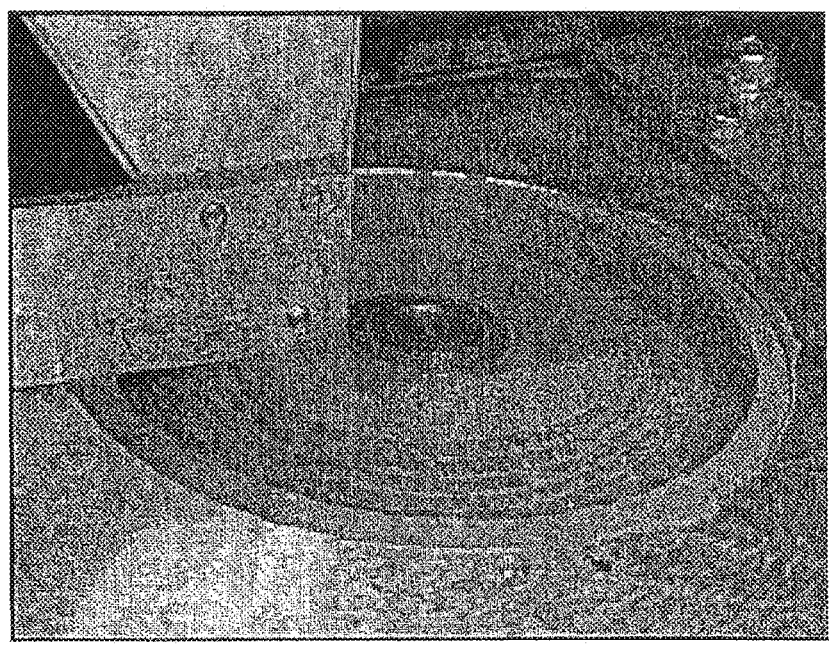
FIG. 58 illustrates a zoomed-in view of the apparatus illustrated in FIG. 55B, further along in the process.

Although the present invention has been described with regard to the femoral hip component as shown in FIG. 48A, the present invention may also be used to construct additional elements. For example, other elements include an acetabular cup component illustrated in FIGS. 49A-49C, augments from knee and hip surgery, FIGS. 50A and 50B, spinal components FIGS. 51A-51C, maxillofacial reconstruction FIGS. 52A and 52B, part of a special Nature, FIG. 53, and other additional irregular shapes such as that shown in FIG. 54. The list of illustrative components above is only an example of various constructs which may be composed using the method as disclosed herein and should be thought of as being inclusive as opposed to exclusive.

Figure 59A:
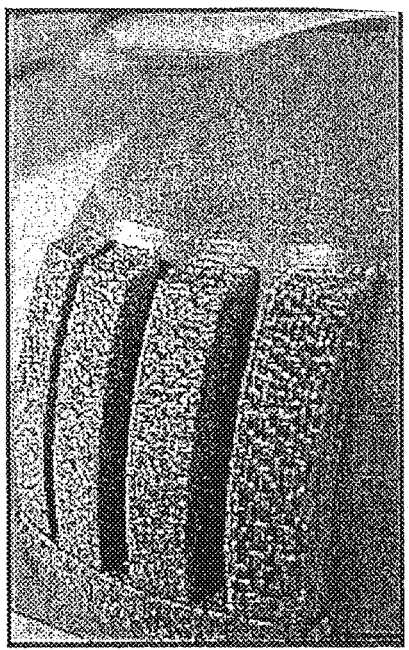
FIGS. 59A and 59B illustrate porous surface coatings being applied to a substrate.
Figure 59B:
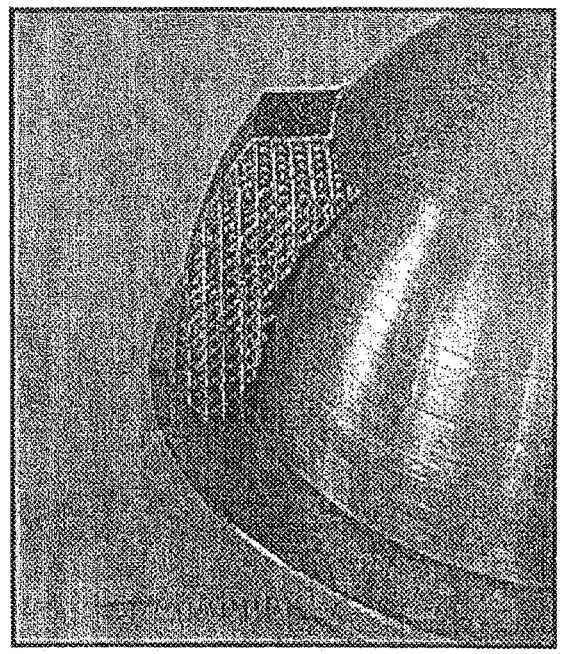
Figure 60A:
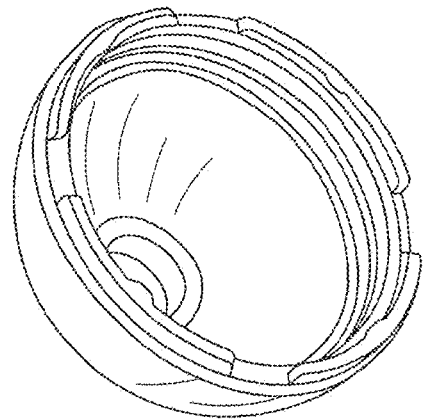
FIGS. 60A and 60B illustrate one embodiment of a representation of a finished product.
Figure 60B:
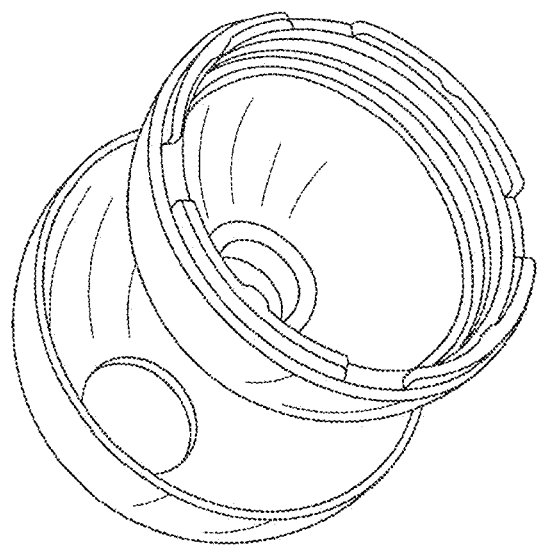
Figure 61A:
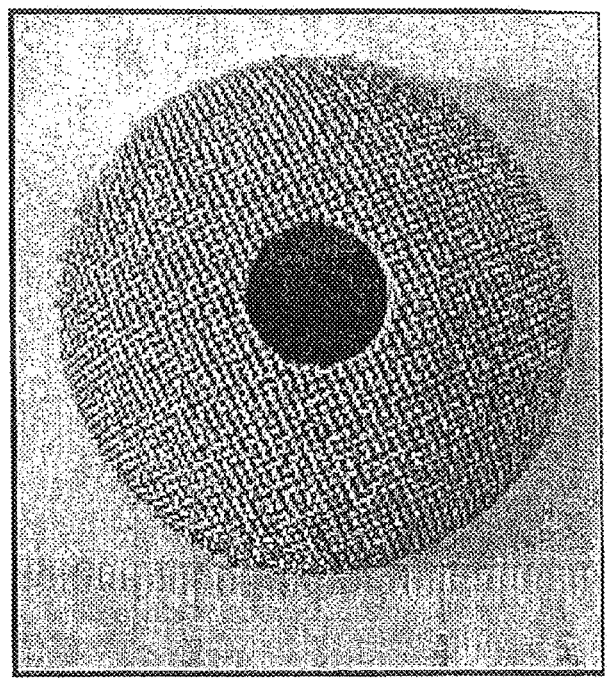
FIGS. 61A and 61B illustrate one embodiment of a finished product created using the present invention.
Figure 61B:
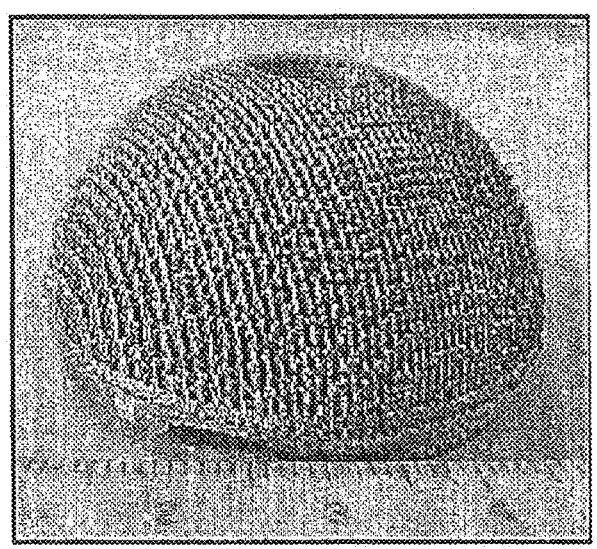
Figure 62A:
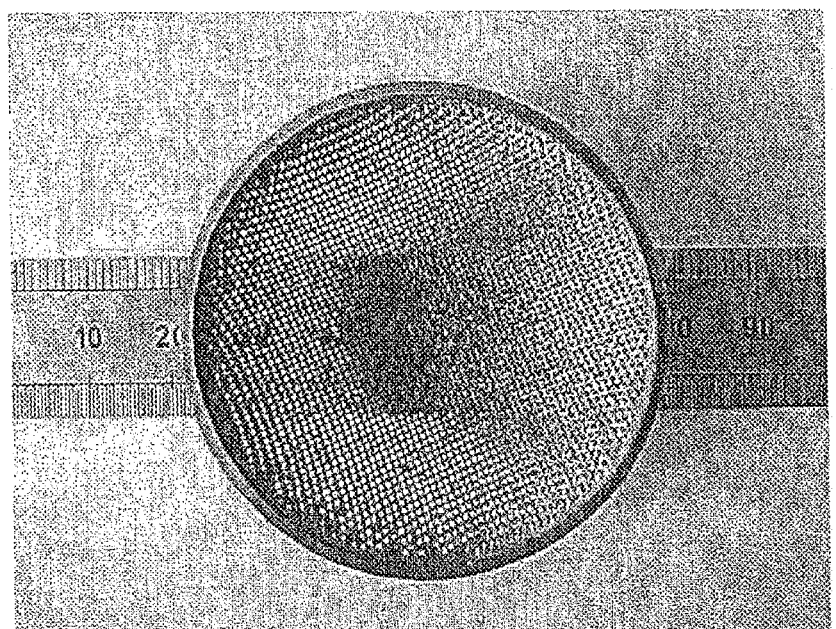
FIGS. 62A to 62D illustrate one embodiment of a finished product created using the present invention.
Figure 62B:
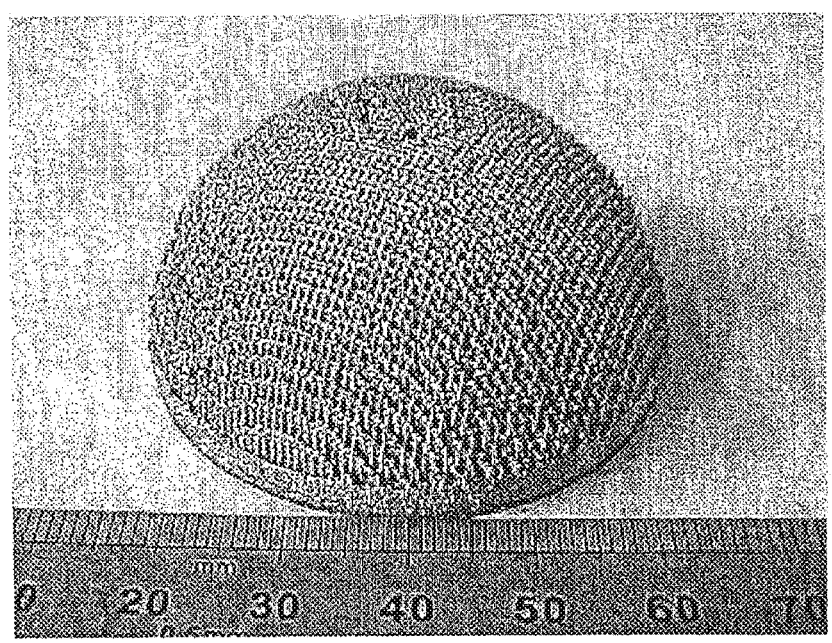
Figure 62C:
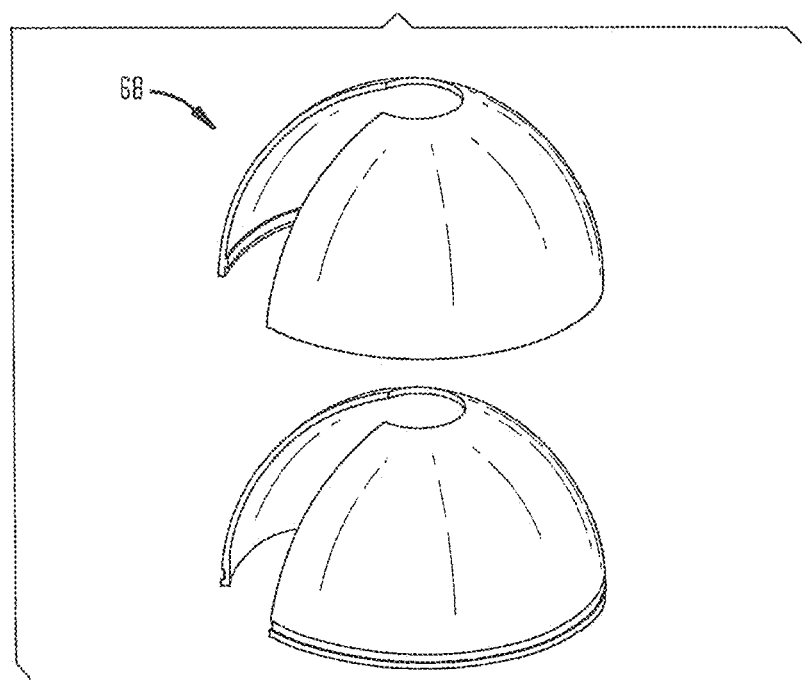
Figure 62D:
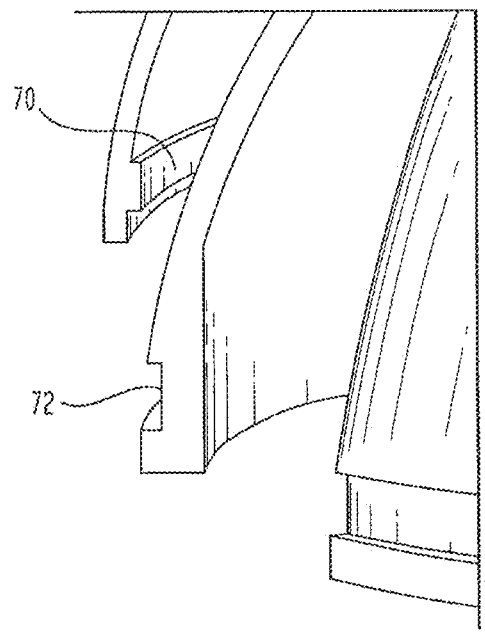

In other aspect of the present invention an existing product may be coated with various metal layers and then scanned with a laser in order to produce a finished product. In order to apply coating to existing products having either concave and/or convex profiles the present invention i.e., SLM requires the design of a special powder lay system. One such example was conducted and is shown in FIGS. 55A-59B. Specifically, a convex surface was created by using build apparatus 60 as shown in FIGS. 55A-58. Build apparatus 60 includes a rotating piston 62 and a cylinder onto which the convex surface 64 to be coated was mounted. As the component rotates on the cylinder, it was made to drop in the Z-direction using platform 66 within the SLM machine. Powder 71 was deposited onto the side of the component using a powder hopper 68 and a wiper device 70 that runs up against the surface of the component. Once the correct amount of powder has been established a laser (not shown in the figures) in conjunction with a computer and various programming packages, including those already discussed, were used to apply a laser beam to the powder in a predetermined manner. The powder was deposited by hopper 68 and wiped to the correct height by wiper device 70. A full layer of metal powder was deposited by rotation of the cylinder through a full 360 degrees. However, the synthesis of the laser melting process and the layer production process requires that only a fraction of the circumference is layered and melted at any one time. For example, the method from production of a full layer would require that the service be built up from, possibly individual quarter revolutions and melting steps as depicted in FIG. 59A. Preferably the laser melting process is fast enough that the discreet stepping process tends to be a continuous one with melting and rotation as well as layering occurring at the same time so as to increase throughput. FIGS. 55A-58 illustrate the sequence of operations with a final coated sample being shown in FIGS. 59A and 59B. In FIG. 59A, the lattice structure was built 3 mm thick and disposed against a 70 mm diameter steel hemisphere. In FIG. 59B, the same hemisphere was used, but the lattice structure is 6 mm thick. FIGS. 60A-60B are CAD illustrations of the final assembly of a product component.

In an alternate embodiment of the present invention, the process can be parallelized by addition of many pistons and cylinder pairs around a central laser beam. Optimal laser alignment to the surface can be achieved by a number of methods, including inclining the piston and cylinder pairs so the powder surface and the part surface are correctly aligned normal to the laser beam. Typical operating parameters are shown in Table 5 below.

TABLE 5

| Slice height (μm) | Power (watts) | Exposure (μs) | $P_{dist}$ (μm) | $H_{dist}$ (mm) |
|---|---|---|---|---|
| 100 | 90.5 | 700 | 80 | 0.125 |

In another aspect of the present invention the laser produced porous structure system may be used to manufacture a porous shell which then can be inserted over a substrate and sintered in order to fix permanently to the same. Some examples include the preparation of an acetabular cup component, a tibia knee insert component, and a femoral insert as well as many additional products. In order to illustrate this aspect of the present invention, reference will be made to the outer profile of an acetabular component which serves as an inner profile of a "cap" to insure that an accurate fit is achieved when the cap is set on the substrate (acetabular shell). The cup is built to a thickness of 1.5 millimeters for example using a diamond configured construct to develop the interconnecting porosity. The metal powder used in one example is stainless steel. The processing parameters are shown in Table 6 listed below:

TABLE 6

| Slice height (μm) | Power (watts) | Exposure (μs) | $P_{dist}$ (μm) | $H_{dist}$ (mm) |
|---|---|---|---|---|
| 100 | 90.5 | 2000 | N/a | N/a |

However, the process parameters are dependent on the metal used and if a different metal, say for example, titanium was used, the parameters would be different. FIGS. 61A-62B illustrate finished products manufactured by SLM.

In order to achieve a better and tighter fit of the cap over the component, some adjustments to the geometry of the cap may be considered. For example, the inclusion of a rim 70 on the inner surface of the cap that interfaces with the groove 72 on the outer surface of the acetabular cup component 68 may be included. This mechanism acts a simple lock and gives both security and extra rigidity during the sintering process. Additional modifications may be utilized to improve closeness of the fit and stability. For instance, the introduction of "snap-fits" which are apparent in everyday plastic components may be employed to provide a more reliable attachment mechanism between the two elements. Typical pads or center pads for both the femoral and tibial knee components can be produced by the SLM process and dropped or snapped fit into place to the components and then sintered to attach firmly to the underlying substrate. As previously stated, this technique can apply to other components where a porous outer surface is required to interface with either soft or hard tissue.

A further improvement in the mechanical and microstructural properties of the porous construct may be achieved by either conventional sintering under vacuum or inert atmosphere and/or hot isostatic pressing using temperature regimes known in the state of the art. As the constructs possess high density properties throughout their strands minimal degradation in the structure of the construct is apparent.

Figure 63:
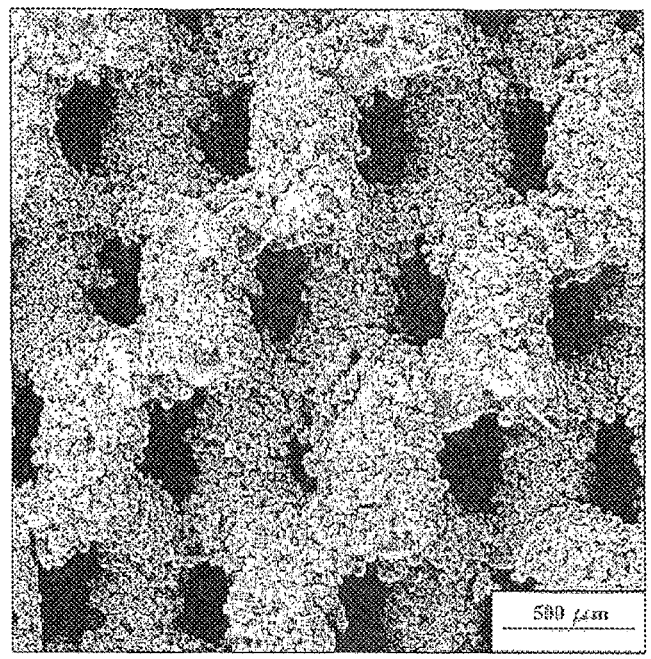
FIG. 63 illustrates a titanium lattice structure with hierarchical surface coating of sintered titanium satellites.

In another aspect of the present invention, the appearance of the porous construct can be changed by the alteration of the processing conditions or by the introduction of an acid etch process. For example, the laser power or laser residence time may be reduced or a combination of both which creates struts of the porous construct having a coating with layers of unmelted metal particles firmly adhered to the strut surfaces. This has the effect of producing additional porous features that offer a new dimension to the overall porous structure of the construct. Such features are able to interact with cells in a different manner than the microstructure imparted by the lattice construct and provide extra benefits. A typical example of such construct with this satellite appearance as depicted in FIG. 63 together with the processing parameters is employed. The structure illustrated in FIG. 63 was created using a laser power of 44.2 W and exposure time of 400 μsec. The metal layer thickness was 50 μm.

Figure 64:
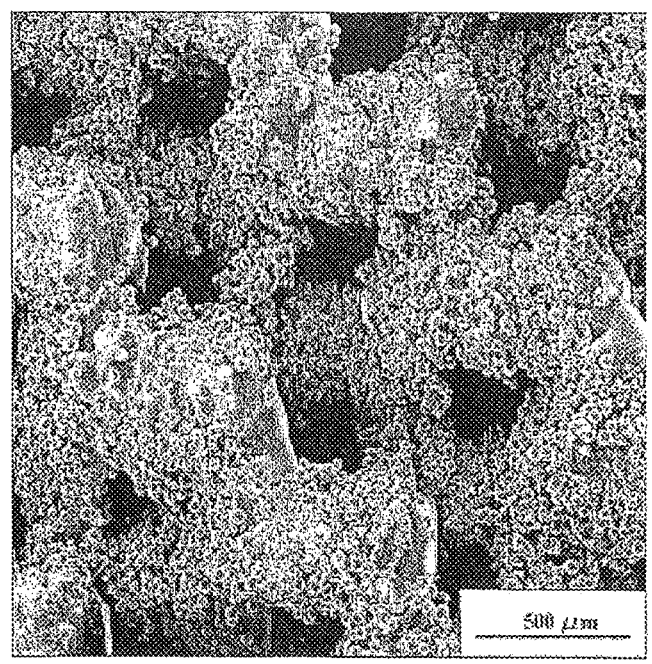
FIGS. 64-71 illustrate the change occurring to the embodiment illustrated in FIG. 63, while the lattice is exposed to a laser at increasing time periods.
Figure 65:
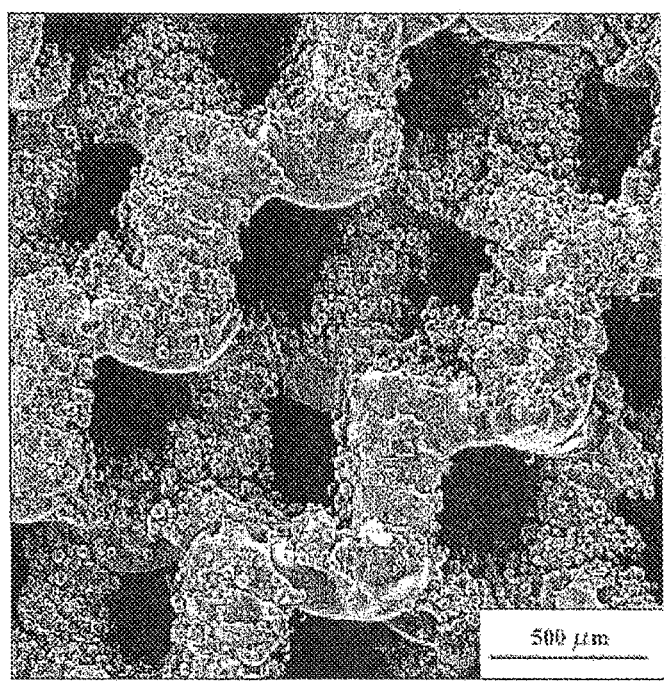
Figure 66:
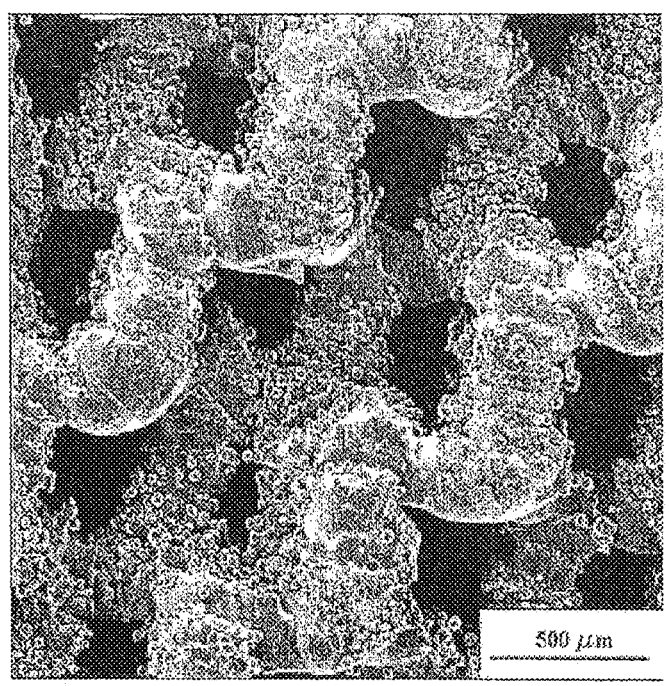
Figure 67:
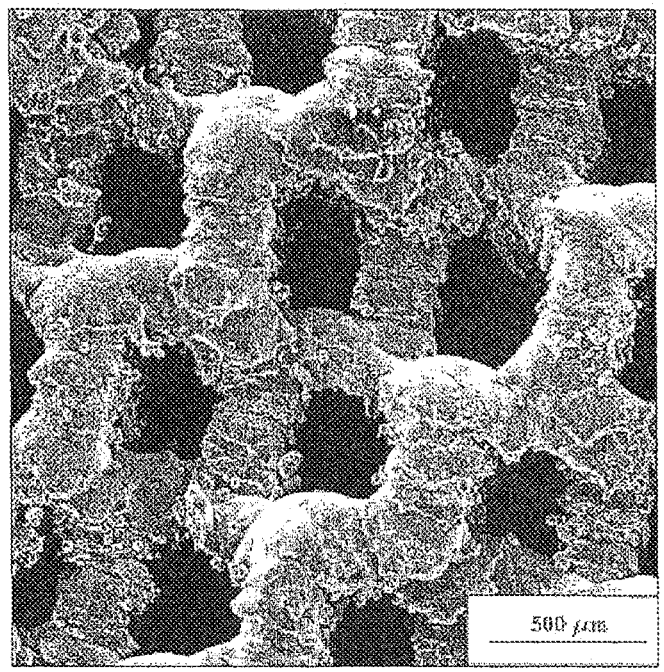
Figure 68:
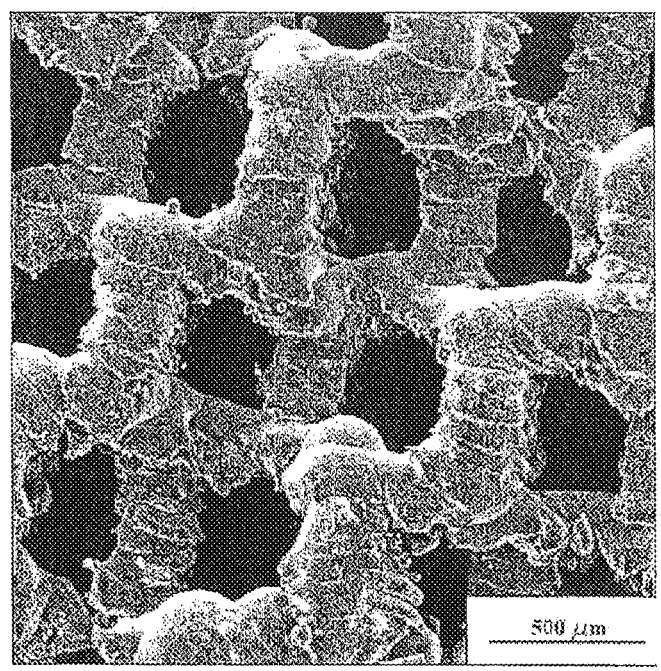
Figure 69:
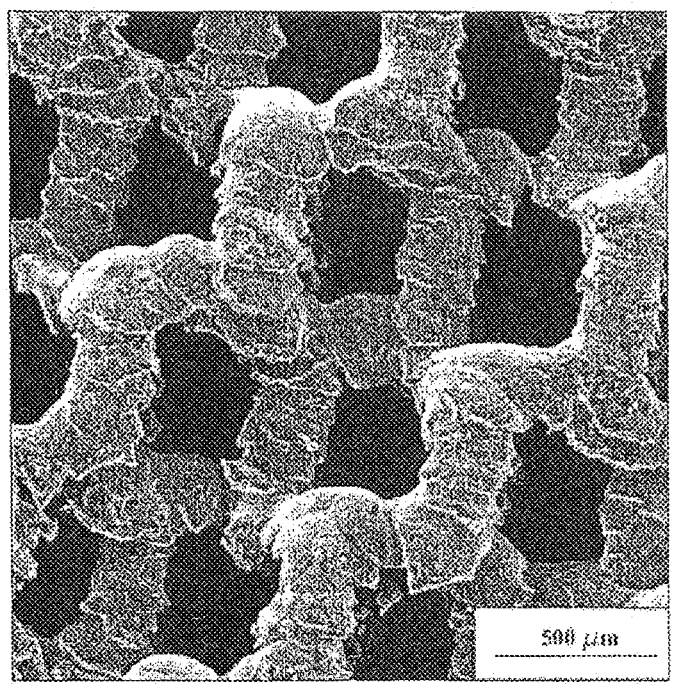
Figure 70:
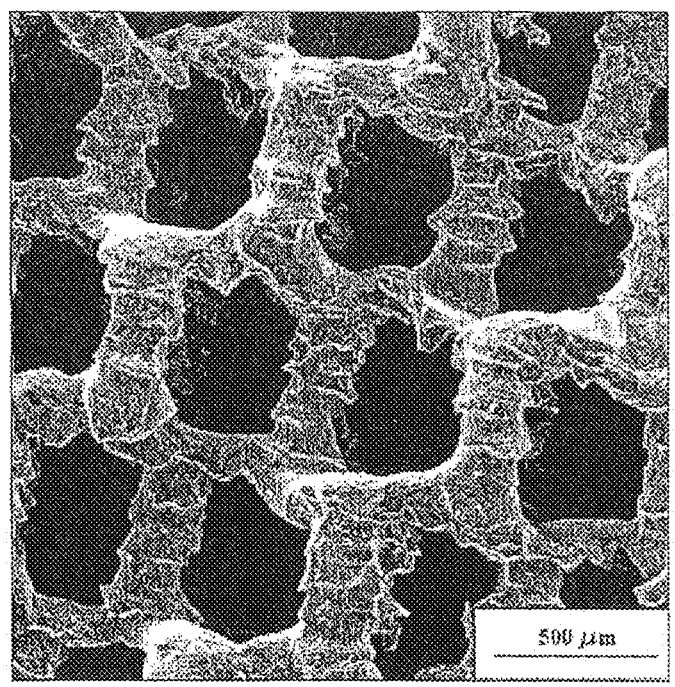
Figure 71:
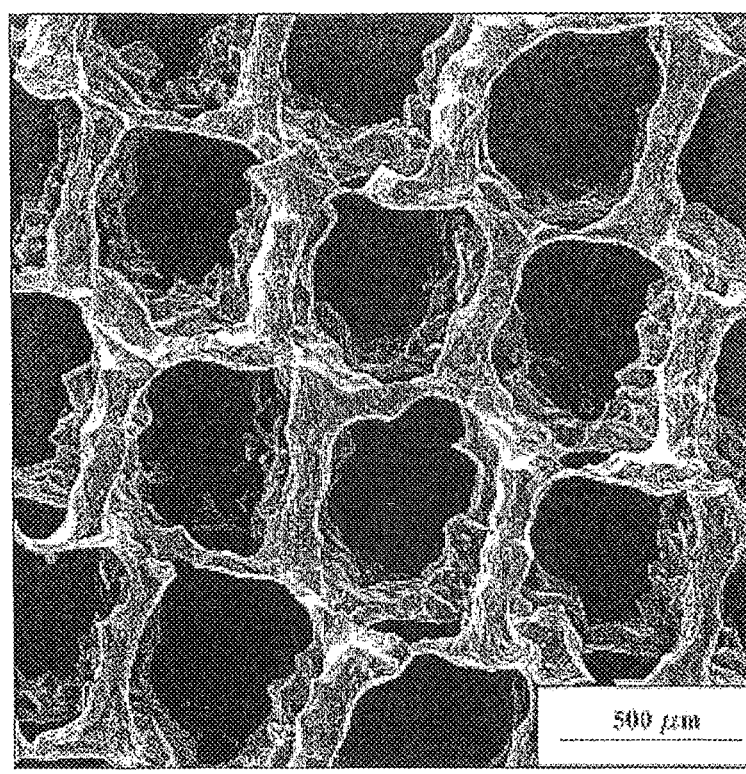

It is also possible to remove these satellites by an acid etching process and a strong acid. The acid may consist of a mixture of 10 milliliters of hydrogenfloride (HF), 5 milliliters of nitric acid ($HNO_3$) and 85 milliliters of $H_2O$. the HF and $HNO_3$ were respectively 48% and 69% concentrated. FIGS. 64 and 71 show the effects of such an acid's etch with respect to time with the relevant conditions being noted. It can be seen clearly that the solids are moved to give a pure melted lattice construct. It is also clearly evident that the overall openness within the lattice is increased by the removal of the satellites. Additionally, prolonged exposure to the acid etch mix does result in some reduction in strut thickness which may also increase the lattice size further. This enables the production of struts having a reduced thickness to be created by the STL method. Other acid types and combination may also be applied to obtain similar results.

It will be appreciated that this method can, therefore, be used to produce an article from the metals referred to which can be created to a desired shape and which may or may not require subsequent machining. Yet again, such an article can be produced so that it has a graded porosity of, e.g., non-porous through various degrees of porosity to the outer surface layer. Such articles could be surgical prostheses, parts or any other article to which this method of production would be advantageous.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fabrication of a medical implant comprising the steps of:
producing a medical implant by rapid manufacturing based on a file prepared by the steps of:
producing a computer-aided design model of the medical implant based on a micro CT scan of a bone; and
populating the design model with solid and porous digitized portions corresponding to respective solid and porous portions of the medical implant,
wherein the solid digitized portion and a plurality of the porous digitized portions together form a plurality of digitized pores.

2. The method of claim 1, wherein the porous digitized portions include porous geometries defining unit cells.

3. The method of claim 2, wherein the unit cells are in a shape of a tetrahedron, a dodecahedron, or an octahedron.

4. The method of claim 2, wherein the unit cells are formed of a plurality of struts, the method further comprising the step of varying either one or both of a cross-sectional area and a length of the struts between at least two unit cells by controlling parameters in the model.

5. The method of claim 2, wherein the step of populating the design model includes a step of forming a plurality of struts having a circular or rectangular cross-section, and wherein the plurality of struts form the unit cells.

6. A method of fabrication of a medical implant comprising the steps of:
producing a medical implant by rapid manufacturing based on a file including a computer-aided design model corresponding to a micro CT scan of a bone, the computer-aided design model having solid and porous digitized portions corresponding to respective solid and porous portions of the medical implant,
wherein the solid digitized portion and a plurality of the porous digitized portions together form a plurality of digitized pores.

7. The method of claim 6, wherein the porous digitized portions include porous geometries defining unit cells.

8. The method of claim 7, wherein the unit cells are in a shape of a tetrahedron, a dodecahedron, or an octahedron.

9. The method of claim 7, wherein the unit cells are formed of a plurality of struts, the method further comprising the step of varying either one or both of a cross-sectional area and a length of the struts between at least two of the unit cells by controlling parameters in the model.

10. The method of claim 7, wherein the step of populating the design model includes a step of forming a plurality of struts having a circular or rectangular cross-section, and wherein the plurality of struts form the unit cells.

11. A method of fabrication of a medical implant comprising the steps of:
producing a medical implant by rapid manufacturing based on a file indicating a computer-aided design model, the computer-aided design model having solid and porous digitized portions corresponding to respective solid and porous portions of the medical implant,
wherein the solid digitized portion and a plurality of the porous digitized portions together form a plurality of digitized pores.

12. The method of claim 11, wherein the porous digitized portions include porous geometries defining unit cells.

13. The method of claim 12, wherein the unit cells are any of a tetrahedron, a dodecahedron, and an octahedron.

14. The method of claim 12, wherein the unit cells are formed of a plurality of struts, the method further comprising the step of varying either one or both of a cross-sectional area and a length of the struts between at least two of the unit cells by controlling parameters in the model.

15. The method of claim 14, wherein the step of populating the design model includes a step of forming a plurality of struts having a circular or rectangular cross-section, and wherein the plurality of struts form the unit cells.

16. The method of claim 12, further comprising the step of populating the computer-aided design model with the solid and porous digitized portions.

* * * * *